United States Patent
Bruninghaus et al.

(10) Patent No.: US 10,570,367 B2
(45) Date of Patent: Feb. 25, 2020

(54) SEED TRAIN PROCESSES AND USES THEREOF

(71) Applicant: Genzyme Corporation, Cambridge, MA (US)

(72) Inventors: Michael Bruninghaus, Framingham, MA (US); Konstantin Konstantinov, Waban, MA (US); Benjamin Wright, Framingham, MA (US); Weichang Zhou, Framingham, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 14/733,630

(22) Filed: Jun. 8, 2015

(65) Prior Publication Data

US 2015/0353896 A1    Dec. 10, 2015

Related U.S. Application Data

(60) Provisional application No. 62/009,553, filed on Jun. 9, 2014.

(51) Int. Cl.
*C12N 5/071* (2010.01)
*C12N 5/00* (2006.01)

(52) U.S. Cl.
CPC ............ *C12N 5/0062* (2013.01); *C12N 5/00* (2013.01); *C12N 2510/02* (2013.01); *C12N 2511/00* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppestein et al. | |
| 6,455,298 B1 * | 9/2002 | Groner ............... | A61K 39/145 424/209.1 |
| 7,354,576 B2 | 4/2008 | Kakkis et al. | |
| 2003/0113915 A1 | 6/2003 | Heidemann et al. | |
| 2005/0186669 A1 | 8/2005 | Ho et al. | |
| 2008/0199958 A1 | 8/2008 | Hui | |
| 2008/0206819 A1 | 8/2008 | Tsao et al. | |
| 2009/0042253 A1 * | 2/2009 | Hiller ................... | C12M 29/16 435/70.3 |
| 2009/0233334 A1 | 9/2009 | Hildinger et al. | |
| 2010/0076380 A1 | 3/2010 | Hui | |
| 2011/0020929 A1 | 1/2011 | Schober et al. | |
| 2012/0164066 A1 | 6/2012 | Greene et al. | |
| 2013/0260419 A1 | 10/2013 | Randohoff et al. | |
| 2014/0154726 A1 | 6/2014 | Yang et al. | |
| 2014/0255994 A1 | 9/2014 | Konstantinov et al. | |
| 2014/0273206 A1 | 9/2014 | Jin et al. | |
| 2015/0158907 A1 | 6/2015 | Zhou et al. | |
| 2015/0183821 A1 | 7/2015 | Konstantinov et al. | |
| 2015/0202595 A1 | 7/2015 | Godawat et al. | |
| 2015/0203529 A1 | 7/2015 | Godawat et al. | |
| 2015/0203531 A1 | 7/2015 | Godawat et al. | |
| 2015/0203532 A1 | 7/2015 | Godawat et al. | |
| 2015/0232505 A1 | 8/2015 | Konstantinov et al. | |
| 2016/0002594 A1 | 1/2016 | Yang et al. | |
| 2016/0017280 A1 | 1/2016 | Villiger-Oberbek et al. | |
| 2016/0017291 A1 | 1/2016 | Yang et al. | |
| 2016/0177361 A1 | 6/2016 | Bae et al. | |

FOREIGN PATENT DOCUMENTS

| | | |
|---|---|---|
| CN | 1564863 | 1/2005 |
| CN | 104450597 | 3/2015 |
| RU | 2058992 | 4/1996 |
| RU | 2215748 | 11/2003 |
| WO | WO 02/050251 | 6/2002 |
| WO | WO 02/50251 | 6/2002 |
| WO | WO 2003/029442 | 4/2003 |
| WO | WO 2003/039459 | 5/2003 |
| WO | WO 2006/033935 | 3/2006 |
| WO | WO 2006/039588 | 4/2006 |
| WO | WO 2006/138143 | 12/2006 |
| WO | WO 2008/073620 | 6/2008 |
| WO | WO 2008/106515 | 9/2008 |
| WO | WO 2008/127087 | 10/2008 |
| WO | WO 2009/034186 | 3/2009 |
| WO | WO 2012/078677 | * 6/2012 |
| WO | WO 2012/078677 | 8/2012 |
| WO | WO 2012/152945 | 11/2012 |
| WO | WO 2013/116449 | 8/2013 |
| WO | WO 2013/151616 | 10/2013 |
| WO | WO 2014/066519 | 5/2014 |
| WO | WO 2014/130864 | 8/2014 |
| WO | WO 2014/130872 | 8/2014 |
| WO | WO 14/137903 | 9/2014 |
| WO | WO 14/143691 | 9/2014 |
| WO | WO 15/039115 | 3/2015 |
| WO | WO 15/109146 | 7/2015 |
| WO | WO 15/109151 | 7/2015 |

(Continued)

OTHER PUBLICATIONS

International Search Report and Written Opinion in International Application No. PCT/US2015034709, dated Oct. 30, 2015, 13 pages.

Clincke et al., "Very High density of CHO cells in perfusion by ATF or TFF in WAVE bioreactor. Part I. Effect of the cell density on the process," Biotechnol Prog. 29(3):754-767, May 2013.

Gargi et al., "Development of a new bioprocess scheme using frozen seed train intermediates to initiate CHO cell culture manufacturing campaigns," Biotech. Bioeng. 110(5):1376-1385, May 4, 2013.

Gebauer and Skerra, "Engineered protein scaffolds as next-generation antibody therapeutics," Current Opin. Chem. Biol. 13(3):245-255, Jun. 2009.

Pohlscheidt et al., "Optimizing capacity utilization by large scale 3000 L perfusion in seed train bioreactors," Biotech. Prog. 29(1):222-229, Jan. 1, 2012.

(Continued)

*Primary Examiner* — Laura Schuberg
(74) *Attorney, Agent, or Firm* — Fish & Richardson P.C.

(57) ABSTRACT

Provided herein are seed train processes and methods of producing a recombinant protein that include the use of these seed train processes.

18 Claims, 6 Drawing Sheets

(56) References Cited

FOREIGN PATENT DOCUMENTS

| WO | WO 2015/188009 | 12/2015 |
|---|---|---|
| WO | WO 2015/188106 | 12/2015 |
| WO | WO 2015/191462 | 12/2015 |
| WO | WO 2016/106192 | 6/2016 |

OTHER PUBLICATIONS

Smelko et al., "Performance of High Intensity Fed-Batch Mammalian Cell Cultures in Disposable Bioreactor Systems," *Biotechnol Prog.* 27(5):1358-1364, 2011.
Tao et al., "Development and Implementation of a Perfusion-Based High Cell Density Cell Banking Process," *Biotechnol Prog.* 27(3):824-829, 2011.
Wright et al., "A novel seed-train process: using high-density cell banking, a disposable bioreactor, and perfusion technologies," *BioProcess Int.* vol. Mar. 2015 Supplement, Mar. 10, 2015.
Yang et al., "Perfusion seed cultures improve biopharmaceutical fed-batch production capacity and product quality," *Biotech. Prog.* 30(3):616-625, May 1, 2014.
Singapore Written Opinion in Application No. 11201610216U, dated Oct. 11, 2017, 6 pages.
Israel Office Action in Application No. 249452, dated Nov. 15, 2018, 7 pages.
Russian Office Action in Application No. 2016151316, dated Nov. 14, 2018, 19 pages.
Barrett et al., "Microwell engineering characterization for mammalian cell culture process development," *Biotechnol Bioeng.*, Feb. 1, 2010, 105(2):260-275.
Chaturvedi et al., "Comparison of the behavior of CHO cells during cultivation in 24-square deep well microplates and conventional shake flask systems," Biotechnology Reports., May 2014, 1(2014): 22-26.
Chinese Office Action in Application No. 2013-80067513.8, dated Apr. 13, 2016, 23 pages.
Chinese Office Action in Application No. 2013-80067513.8, dated Dec. 29, 2016, 22 pages.
Chinese Office Action in Application No. 201480022766.8, dated May 4, 2017, 14 pages.
Chinese Office Action in Application No. 201480022715.5, dated May 15, 2017, 78 pages.
Chinese Office Action in Application No. 201380067513.8, dated Jun. 6, 2017, 15 pages.
Chinese Office Action in Application No. 201480022715.5, dated Jul. 5, 2017.
Chinese Office Action in Application No. 201480022766.8, dated Jan. 3, 2018, 7 pages.
Chinese Office Action in Application No. 201480022715.5, dated Feb. 13, 2018.
Communication in European Office Action in European Application No. 14709106.0, dated Oct. 17, 2017, 3 pages.
Communication in European Office Action in European Application No. 13786587.9, dated Nov. 28, 2017, 4 pages.
Corning-24, Corning Costar Ultra-low attachment multiwell plates, Sigma-Aldrich Catalog Webpage, Aug. 10, 2017.
Costa et al, "The impact of microcarrier culture optimization on the glycosylation profile of a monoclonal antibody," Springer Plus, Jan. 28, 2013, 2(25): 1-10.
Danielson et al., "Maximizing cell densities in miniprep-scale cultures with H15 medium and improved oxygen transfer," Biochemical Engineering J, Dec. 2004, 17:175-180.
De Jesus et al., "Tubespin satellites, A fast track approach for process development with animal cells using shaking technology," Biotechnology and Bioengineering Journal, Mar. 2004, 17(3): 217-223.
Domansky et al., "Perfused multiwell plate for 3D liver tissue engineering," Lab on a Chip, Jan. 1, 2010, 10(1):51-58.
European Office Action in European Application No. 13786587.9, dated Mar. 15, 2016.
European Office Action in European Application No. 14709829.7, dated Jun. 27, 2016, 5 pages.
European Office Action in European Application No. 13786587.9, dated Sep. 27, 2016, 11 pages.
European Office Action in European Application No. 13786587.9, dated Feb. 20, 2017, 6 pages.
European Office Action in European Application No. 14709829.7, dated Aug. 30, 2017, 3 pages.
European Office Action in European Application No. 15730933.7 dated Oct. 23, 2017, 2 pages.
Fernandes-Platzgummer et al., Scale-up of mouse embryonic stem cell expansion in stirred bioreactors, American Institute Chemical Engineers, dated Sep./Oct. 2011, 27(5): 1421-1432.
Final Office Action in U.S. Appl. No. 14/769,783, dated Mar. 28, 2017, 38 pages.
Final Office Action in U.S. Appl. No. 14/769,772, dated May 9, 2017, 23 pages.
Final Office Action issued in U.S. Appl. No. 14/061,657 dated Aug. 19, 2016, 13 pages.
Final Office Action in U.S. Appl. No. 14/769,783, dated Feb. 22, 2018, 19 pages.
Huang et al., "Maximizing productivity of CHO cell-based fed-batch culture using chemically defined media conditions and typical manufacturing equipment," American Institute of Chemical Engineers Biotechnol. Prog., Sep. 2010, 26: 1400-1410.
International Preliminary Report on Patentability for PCT/US2014/017785, dated Aug. 25, 2015, 7 pages.
International Preliminary Report on Patentability for PCT/US2014/017803, dated Aug. 25, 2015, 8 pages.
International Preliminary Report on Patentability in International Application No. PCT/US2013/066410, dated Apr. 28, 2015, 8 pages.
International Preliminary Report on Patentability in International Application No. PCT/US2015/034494, dated Dec. 6, 2016, 14 pages.
International Search Report and the Written Opinion issued in PCT/US2013/066410 dated Jan. 31, 2014 (12 pages).
International Search Report and Written Opinion for PCT/US2014/017785, dated May 20, 2014, 10 pages.
International Search Report and Written Opinion for PCT/US2014/017803, dated May 20, 2014, 10 pages.
International Search Report and Written Opinion in International Application No. PCT/US2015/034494, dated Nov. 30, 2015, 24 pages.
International Search Report and Written Opinion in International Application No. PCT/US2015/067040, dated Sep. 5, 2016, 19 pages.
Invitation to Pay for PCT/US2015/034494, dated Aug. 12, 2015, 6 pages.
Jayapal et al., "Recombinant Protein Therapeutics from CHO cells—20 years and counting", Chemical Engineering Progress, Oct. 2007, 103(10):40-47.
Katakam et al., "Effect of Surfactants on the physical stability of recombinant human growth hormone" Journal of Pharmaceutical Association, Jun. 1, 1995, 84(6): 713-716.
Kim et al., "Batch, Fed-Batch and Microcarrier Cultures with CHO cell lines in a pressure-cycle driven miniaturized bioreactor," Biotechnology and Bioengineering, Oct. 2011, 109(1): 137-145.
Nam et al., "The effects of microcarrier culture on recombinant CHO cells under biphasic hypothermic culture conditions," *Cytotechnology*, 59(2):81-91, Epub May 2, 2009.
Non-final Office Action issued in U.S. Appl. No. 14/061,657 dated Nov. 5, 2015, 12 pages.
Non-final Office Action Issued in U.S. Appl. No. 14/769,783, dated Nov. 3, 2016, 36 pages.
Non-final Office Action in U.S. Appl. No. 14/733,630, dated Nov. 15, 2016, 13 pages.
Non-final Office Action in U.S. Appl. No. 14/769,772, dated Dec. 6, 2016, 19 pages.
Non-Final Office Action issued in U.S. Appl. No. 14/732,325, dated Sep. 20, 2017, 10 pages.
Non-Final Office Action issued in U.S. Appl. No. 14/769,783, dated Oct. 10, 2017, 23 pages.

(56) References Cited

OTHER PUBLICATIONS

Non-final Office Action issued in U.S. Appl. No. 14/061,657 dated Nov. 24, 2017, 9 pages.
Notification of Transmittal of the International Search Report and the Written Opinion issued in PCT/US2013/066410 dated Jan. 31, 2014 (10 pages).
Rodrigues et al., "Technological progresses in monoclonal antibody production systems," *Biotechnol Prog.*, Mar.-Apr. 2010, 26(2):332-351.
Schirmer et al., "Primary clarification of very high density cell culture harvests by enhanced cell settling," BioProcress International, Jan. 2010, pp. 32-39.
Rosario and Scott, "Growth of mesenchymal stromal cells in automated microwell cultures: influence of the engineering environment on cell growth kinetics and non-directed differentiation," (Doctoral dissertation, UCL (University College London), Sep. 2008, 202 pages.
Senger et al., "Effect of shear stress on intrinsic CHO culture state and glycosylation of recombinant tissue-type plasminogen activator protein," Biotechnology Progress Jul.-Aug. 2003, 19(4): 1199-1209; Abstract only.
Shi et al., "Expansion of Mouse Sertoli Cells on Microcarriers, Cell Proliferation," Jun. 2010, 43(3): 275-286.
Silk et al., "Fed-batch operation of an industrial cell culture process in shaken microwells," Biotechnol Lett., 32(1):73-78, print Jan. 2010, Epub Sep. 17, 2009.
Singapore Written Opinion in Singaporean Patent Application No. 11201506343Q, dated Jun. 27, 2016, 5 pages.
Singapore Written Opinion in Singaporean Patent Application No. 11201506339R, dated Jul. 21, 2016, 5 pages.
Singapore Written Opinion in Singaporean Patent Application No. 11201503085V, dated Dec. 7, 2016, 9 pages.
Singapore Written Opinion in Singaporean Patent Application No. 11201506339R, dated Jul. 13, 2017, 4 pages.
Singapore Written Opinion in Singaporean Patent Application No. 11201506343Q, dated Jul. 13, 2017, 5 pages.
Singapore Written Opinion in Singaporean Patent Application No. 11201506339R, dated Jul. 20, 2017, 5 pages.
Singapore Written Opinion in Singaporean Patent Application No. 1120160167W, dated Oct. 17, 2017, 7 pages.
Singapore Written Opinion in Singaporean Patent Application No. 11201503085V, dated Feb. 19, 2018, 7 pages.
Soyer et al., "Introducing shear stress in the study of bacterial adhesion," J. Vis. Exp. Sep. 2011, (55):e3241.
Strnad et al., "Optimization of cultivation conditions in spin tubes for Chinese hamster ovary cells producing erythropoietin and the comparison of glycosylation patterns in different cultivation vessels," Biotechnology Progress, May-Jun. 2010, 26(3):653-663 (2010).
Tordahl et al., "Study of a perfusion process of Chinese hamster ovary cells by ATF filtration in bioreactor ovary cells by ATF filtration in bioreactor," Sep. 11, 2009.
Villiger-Oberbek, "Development and application of a high-throughout platform for perfustion-based cell culture processes," Journal of Biotechnology, Oct. 2015, 21: 21-29.
Written Opinion in Australian Patent Application No. 2013334602, dated May 23, 2017, 2 pages.
Yizheng et al., Oxygen transfer reaction characteristics, Chemical Industry Press, Bioreaction Engineering, dated Jul. 31, 2004, pp. 134-139.
Zhang et al., "A robust high-throughput sandwich cell-based drug screening platform," Biomaterials, Feb. 1, 2011, 32(4):1229-124.
Mexican Office Action in Application No. MX/a/2016/016301, dated Oct. 30, 2018, 8 pages.

* cited by examiner

Conventional seed train process:

Exemplary seed train process provided herein:

us 10,570,367 B2

SEED TRAIN PROCESSES AND USES THEREOF

CROSS REFERENCE TO RELATED APPLICATIONS

This application claims the benefit of U.S. provisional application 62/009,553, filed Jun. 9, 2014, the entire content of which is hereby incorporated by reference.

TECHNICAL FIELD

This invention relates to methods of biotechnology and the biomanufacturing of recombinant proteins.

BACKGROUND

Mammalian cells containing a nucleic acid that encodes a recombinant protein are often used to produce therapeutically or commercially important proteins. In the current environment of diverse product pipelines, biotechnology companies are increasingly driven to develop innovative solutions for highly flexible and cost-effective manufacturing of therapeutic agents.

Mammalian cells containing a nucleic acid that encodes a recombinant protein are often cultured in large production bioreactors to produce therapeutic proteins of interest. Seed train processes are used to generate a sufficient number of such mammalian cells to inoculate the large production bioreactors. Conventional seed train processes start with the thawing of a cryopreserved cell bank vial, followed by multiple culturing steps (e.g., 5 or more) in progressively larger culture vessels. Conventional seed train processes have several disadvantages including the requirement for multiple manual manipulations during each step, which makes the whole process vulnerable to contamination and operator error. In addition, conventional seed train processes are time-consuming due to the number of culturing steps, and due to the low cell densities achieved at the N−1 step (cell culture penultimate to the inoculation of the production bioreactor) that can only result in a starting cell density of less than $0.5 \times 10^6$ cells/mL in large-scale production bioreactors, which requires a 5-10 day growth phase in order to reach the steady state production cell density.

SUMMARY

The present invention is based, at least in part, on the development of a seed train processes that result in several advantages including, for example, less complexity, a reduced number of culturing steps, a reduction in the amount of time from a starting cell culture (e.g., a thawed cell bank) to inoculation of a production bioreactor, a reduced amount of manual manipulation, a reduced risk of contamination, a higher starting cell viable cell density in the production bioreactor, and a shorter growth phase in the production bioreactor (e.g., a short time period required to reach the steady state production cell density). The provided seed train processes include (a) disposing a plurality of recombinant mammalian cells into a first culture medium included within a vessel to provide a first cell culture; (b) batch culturing the first cell culture to a cell density range of about $1.0 \times 10^6$ cells/mL to about $5.0 \times 10^6$ cells/mL; (c) disposing a volume of the first cell culture of (b) into a second culture medium included within a perfusion bioreactor to provide a second cell culture with an initial cell density in a range of about $0.25 \times 10^6$ cells/mL to about $0.50 \times 10^6$ cells/mL; (d) perfusion culturing the second cell culture to a cell density range of between about $5.0 \times 10^6$ cells/mL to about $120 \times 10^6$ cells/mL; and (e) disposing a volume of the second cell culture of (d) into a third culture medium included within a production bioreactor to provide a production cell culture with an initial cell density in a range of about $0.20 \times 10^6$ cells/mL to about $8.0 \times 10^6$ cells/mL. Also provided herein are methods of producing a recombinant protein (e.g., a recombinant therapeutic protein) that include the use of one of the seed train processes described herein.

Provided herein are seed train processes that include: (a) disposing a plurality of recombinant mammalian cells into a first culture medium comprised within a vessel to provide a first cell culture; (b) batch culturing the first cell culture to a cell density range of about $1.0 \times 10^6$ cells/mL to about $5.0 \times 10^6$ cells/mL; (c) disposing a volume of the first cell culture of step (b) into a second culture medium comprised within a perfusion bioreactor to provide a second cell culture with an initial cell density in a range of about $0.25 \times 10^6$ cells/mL to about $0.5 \times 10^6$ cells/mL; (d) perfusion culturing the second cell culture to a cell density range of between about $5 \times 10^6$ cells/mL to about $120 \times 10^6$ cells/mL; and (e) disposing a volume of the second cell culture of step (d) into a third culture medium comprised within a production bioreactor to provide a production cell culture with an initial cell density in a range of about $0.25 \times 10^6$ cells/mL to about $8 \times 10^6$ cells/mL. In some embodiments of these methods, the disposing of the plurality of recombinant mammalian cells in (a) includes: thawing a frozen cell bank; and disposing a volume of the thawed cell bank into the first culture medium. In some embodiments of any of the methods described herein, the frozen cell bank contains a cell density range of about $10 \times 10^7$ cells/mL to about $50 \times 10^7$ cells/mL. In some embodiments of any of the methods described herein, the thawed cell bank contains a percentage of viable cells of at least 60% (e.g., at least 90%).

In some embodiments of any of the methods described herein, the disposing of the plurality of recombinant mammalian cells in (a) includes disposing a volume of a third cell culture containing the plurality of recombinant mammalian cells into the first culture medium. Some embodiments of any of the methods described herein further include (1) disposing a plurality of the recombinant mammalian cells into a fourth culture medium comprised within a vessel to provide the third cell culture; (2) batch culturing the third cell culture of (1) to a cell density range of about $1.0 \times 10^6$ cells/mL to about $5.0 \times 10^6$ cells/mL, where a volume of the third cell culture in (2) is disposed into the first culture medium in (a). In some embodiments of any of the methods provided herein, one or both of the vessel in (a) or the vessel in (1) is a disposable single-use bioreactor (e.g., a disposable single-use bioreactor including a plastic sterile bag).

In some embodiments of any of the methods described herein, the disposing of the plurality of the recombinant mammalian cells in (1) includes thawing a frozen cell bank, and disposing a volume of the thawed cell bank into the fourth culture medium. In some embodiments of any of the methods described herein, the frozen cell bank comprises a cell density range of about $10 \times 10^7$ cells/mL to about $50 \times 10^7$ cells/mL. In some embodiments of any of the methods described herein, the thawed cell bank contains a percentage of viable cells of at least 60% (e.g., at least 90%).

In some embodiments of any of the methods described herein, the first cell culture in (a) has a volume range of about 1.0 L to about 50 L (e.g., about 5.0 L to about 10. L). In some embodiments of any of the methods described herein, the second cell culture in (c) has a volume range of about 5 L to about 600 L (e.g., about 10 L to about 300 L). In some embodiments of any of the methods described herein, the production cell culture in (e) has a volume range of about 50 L to about 20,000 L (e.g., about 100 L to about 10,000 L). In some embodiments of any of the methods described herein, the fourth culture medium in (1) has a volume range of about 500 mL to about 20 L (e.g., about 500 mL to about 10 L).

In some embodiments of any of the methods described herein, the vessel in (a) has an internal volume range of about 1.5 L to about 100 L (e.g., about 1.5 L to about 50 L). In some embodiments of any of the methods described herein, the perfusion bioreactor in (c) has an internal volume range of about 7.5 L to about 1,000 L (e.g., about 50 L to about 1000 L). In some embodiments of any of the methods described herein, the production bioreactor in (e) has an internal volume range of about 150 L to about 25,000 L (e.g., about 150 L to about 10,000 L). In some embodiments of any of the methods described herein, the vessel in (1) has an internal volume range of about 1 L to about 40 L (e.g., about 1 L to about 20 L).

In some embodiments of any of the methods described herein, the perfusion culturing in (c) is performed using a perfusion bioreactor equipped with an alternating tangential flow filtration device. In some embodiments of any of the methods described herein, the initial cell density in (e) is in a range of about $2.0\times10^6$ cells/mL to about $8\times10^6$ cells/mL. In some embodiments of any of the methods described herein, the initial cell density in (e) is at least 10% (e.g., at least 20%) of the steady state production cell density.

Also provided are methods of producing a recombinant protein that include: (a) disposing a plurality of recombinant mammalian cells into a first culture medium comprised within a vessel to provide a first cell culture; (b) batch culturing the first cell culture to a cell density range of about $1.0\times10^6$ cells/mL to about $5.0\times10^6$ cells/mL; (c) disposing a volume of the first cell culture medium of (b) into a second culture medium comprised within a perfusion bioreactor to provide a second cell culture with an initial cell density in a range of about $0.25\times10^6$ cells/mL to about $0.5\times10^6$ cells/mL; (d) perfusion culturing the second cell culture to a cell density range of between about $5\times10^6$ cells/mL to about $60\times10^6$ cells/mL; (e) disposing a volume of the second cell culture of (d) into a third culture medium comprised within a production bioreactor to provide a production cell culture with an initial cell density in a range of about $0.25\times10^6$ cells/mL to about $8\times10^6$ cells/mL; (f) perfusion culturing the production cell culture under conditions that allow the recombinant mammalian cells to secrete a recombinant protein; and (g) harvesting the recombinant protein from the production cell culture. In some embodiments of any of the methods described herein, the disposing of the plurality of recombinant mammalian cells in (a) includes: thawing a frozen cell bank; and disposing a volume of the thawed cell bank into the first culture medium. In some embodiments of any of the methods described herein, the frozen cell bank has a cell density range of about $10\times10^7$ cells/mL to about $50\times10^7$ cells/mL. In some embodiments of any of the methods described herein, the thawed cell bank contains a percentage of viable cells of at least 60% (e.g., at least 90%).

In some embodiments of any of the methods described herein, the disposing of the plurality of recombinant mammalian cells in (a) includes disposing a volume of a third cell culture comprising the plurality of recombinant mammalian cells into the first culture medium. Some embodiments of any of the methods described herein further include: (1) disposing a plurality of the recombinant mammalian cells into a fourth culture medium comprised within a vessel to provide the third cell culture; and (2) batch culturing the third cell culture in (1) to a cell density range of about $1.0\times10^6$ cells/mL to about $5.0\times10^6$ cells/mL, where a volume of the third cell culture in (2) is disposed into the first culture medium in (a). In some embodiments of any of the methods described herein, one or both of the vessel in (a) or the vessel in (1) is a disposable single-use bioreactor (e.g., a disposable single-use bioreactor including a plastic sterile bag).

In some embodiments of any of the methods described herein, the disposing of the plurality of the recombinant mammalian cells in (1) includes: thawing a frozen cell bank; and disposing a volume of the thawed cell bank into the fourth culture medium. In some embodiments of any of the methods described herein, the frozen cell bank comprises a cell density range of about $1.0\times10^7$ cells/mL to about $50\times10^7$ cells/mL (e.g., between about $10\times10^7$ cells/mL to about $50\times10^7$ cells/mL). In some embodiments of any of the methods described herein, the thawed cell bank contains a percentage of viable cells of at least 60% (e.g., at least 90%).

In some embodiments of any of the methods described herein, the first cell culture in (a) has a volume range of about 1.0 L to about 50 L (e.g., between about 5.0 L and about 10.0 L). In some embodiments of any of the methods described herein, the second cell culture in (c) has a volume range of about 5 L to about 600 L (e.g., about 10 L to about 300 L). In some embodiments of any of the methods described herein, the production cell culture in (e) has a volume range of about 50 L to about 20,000 L (e.g., about 100 L to about 10,000 L). In some embodiments of any of the methods described herein, the fourth culture medium in (1) has a volume range of about 500 mL to about 20 L (e.g., about 500 mL to about 10 L).

In some embodiments of any of the methods described herein, the vessel in (a) has an internal volume range of about 1.5 L to about 100 L (e.g., about 1.5 L to about 50 L). In some embodiments of any of the methods described herein, the perfusion bioreactor in (c) has an internal volume range of about 7.5 L to about 1,000 L (e.g., about 50 L to about 1000 L). In some embodiments of any of the methods described herein, the production bioreactor in (e) has an internal volume range of about 150 L to about 25,000 L (e.g., 150 L to about 10,000 L). In some embodiments of any of the methods described herein, the vessel in (1) has an internal volume range of about 1 L to about 40 L (e.g., about 1 L to about 20 L).

In some embodiments of any of the methods described herein, the perfusion culturing in (c) is performed using a perfusion bioreactor equipped with an alternating tangential flow filtration device. In some embodiments of any of the methods described herein, the initial cell density in (e) is in a range of about $2.0\times10^6$ cells/mL to about $8\times10^6$ cells/mL. In some embodiments of any of the methods described herein, the initial cell density in (e) is at least 10% (e.g., at least 20%) of the steady state production cell density. In some embodiments of any of the methods described herein, the steady state production cell density is between $5\times10^6$ cells/mL to about $50\times10^6$ cells/mL (e.g., between about $15\times10^6$ cells/mL to about $50\times10^6$ cells/mL). In some embodiments of any of the methods described herein, the perfusion culturing in (f) results in the production cell culture reaching the steady state production cell density in a period of between about 1 day to about 10 days (e.g., between about 2 days to about 5 days).

In some embodiments of any of the methods described herein, the harvesting in (g) includes removing (e.g., continuously removing) culture medium from the production bioreactor. Some embodiments of any of the methods described herein further include isolating the recombinant protein from the removed culture medium. In some embodiments of any of the methods described herein, the isolating is performed using an integrated and continuous process. Some embodiments of any of the methods described herein further include formulating the isolated recombinant protein into a pharmaceutical agent.

As used herein, the word "a" before a noun represents one or more of the particular noun. For example, the phrase "a recombinant mammalian cell" represents "one or more recombinant mammalian cells."

The term "mammalian cell" means any cell from or derived from any mammal (e.g., a human, a hamster, a mouse, a green monkey, a rat, a pig, a cow, or a rabbit). For example, a mammalian cell can be an immortalized cell. In some embodiments, the mammalian cell is a differentiated cell. In some embodiments, the mammalian cell is an undifferentiated cell. Non-limiting examples of mammalian cells are described herein. Additional examples of mammalian cells are known in the art.

The term "seed train process" is art-known and means a multi-step method by which a starting number of cells (e.g., recombinant mammalian cells) in a first cell culture is expanded into an N−1 cell culture that contains a sufficient number of cells to inoculate a typical production bioreactor at an initial cell density of greater than $0.25 \times 10^6$ cells/mL.

The term "substantially free" means a composition (e.g., a liquid culture medium) that is at least or about 90% free (e.g., at least or about 95%, 96%, 97%, 98%, or at least or about 99% free, or about 100% free) of a specified substance (e.g., a mammalian cell).

The term "0.5× volume" means about 50% of the volume. The term "0.6× volume" means about 60% of the volume. Likewise, 0.7×, 0.8×, 0.9×, and 1.0× means about 70%, 80%, 90%, or 100% of the volume, respectively.

The term "culturing" or "cell culturing" means the maintenance or proliferation of a mammalian cell (e.g., a recombinant mammalian cell) under a controlled set of physical conditions.

The term "culture of mammalian cells" or "cell culture" means a liquid culture medium containing a plurality of mammalian cells that is maintained or proliferated under a controlled set of physical conditions.

The term "liquid culture medium" or "culture medium" means a fluid that contains sufficient nutrients to allow a cell (e.g., a mammalian cell) to grow or proliferate in vitro. For example, a liquid culture medium can contain one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, and sodium bicarbonate. In some embodiments, a liquid culture medium can contain serum from a mammal. In some embodiments, a liquid culture medium does not contain serum or another extract from a mammal (a defined liquid culture medium). In some embodiments, a liquid culture medium can contain trace metals, a mammalian growth hormone, and/or a mammalian growth factor. Another example of liquid culture medium is minimal medium (e.g., a medium containing only inorganic salts, a carbon source, and water). Non-limiting examples of liquid culture medium are described herein. Additional examples of liquid culture medium are known in the art and are commercially available. A liquid culture medium can contain any density of mammalian cells. For example, as used herein, a volume of liquid culture medium removed from a production bioreactor can be substantially free of mammalian cells.

The term "animal-derived component free liquid culture medium" means a liquid culture medium that does not contain any components (e.g., proteins or serum) derived from a mammal.

The term "serum-free liquid culture medium" means a liquid culture medium that does not contain a mammalian serum.

The term "serum-containing liquid culture medium" means a liquid culture medium that contains a mammalian serum.

The term "chemically-defined liquid culture medium" is a term of art and means a liquid culture medium in which all of the chemical components are known. For example, a chemically-defined liquid culture medium does not contain fetal bovine serum, bovine serum albumin, or human serum albumin, as these preparations typically contain a complex mix of albumins and lipids.

The term "protein-free liquid culture medium" means a liquid culture medium that does not contain any protein (e.g., any detectable protein).

The term "agitation" means stirring or otherwise moving a portion of liquid culture medium in a vessel (e.g., bioreactor). This is performed in order to, e.g., increase the dissolved $O_2$ concentration in the liquid culture medium in a vessel (e.g., bioreactor). Agitation can be performed using any art known method, e.g., an instrument or propellor. For example, agitation can be performed by placing a vessel on a platform that tilts and/or rotates. Exemplary devices and methods that can be used to perform agitation of a portion of the liquid culture medium in a vessel (e.g., a bioreactor) are known in the art.

The term "integrated process" means a process which is performed using structural elements that function cooperatively to achieve a specific result (e.g., the generation of an isolated recombinant protein from a liquid culture medium).

The term "continuous process" means a process which continuously feeds fluid through at least a part of the system.

The term "immunoglobulin" means a polypeptide containing an amino acid sequence of at least 15 amino acids (e.g., at least 20, 30, 40, 50, 60, 70, 80, 90, or 100 amino acids) of an immunoglobulin protein (e.g., a variable domain sequence, a framework sequence, or a constant domain sequence). The immunoglobulin may, for example, include at least 15 amino acids of a light chain immunoglobulin, e.g., at least 15 amino acids of a heavy chain immunoglobulin. The immunoglobulin may be an isolated antibody (e.g., an IgG, IgE, IgD, IgA, or IgM). The immunoglobulin may be a subclass of IgG (e.g., IgG1, IgG2, IgG3, or IgG4). The immunoglobulin may be an antibody fragment, e.g., a Fab fragment, a F(ab')$_2$ fragment, or an a scFv fragment. The immunoglobulin may also be a bi-specific antibody or a tri-specific antibody, or a dimer, trimer, or multimer antibody, or a diabody, an Affibody®, or a Nanobody®. The immunoglobulin can also be an engineered protein containing at least one immunoglobulin domain (e.g., a fusion protein). Non-limiting examples of immunoglobulins are described herein and additional examples of immunoglobulins are known in the art.

The term "protein fragment" or "polypeptide fragment" means a portion of a polypeptide sequence that is at least or about 4 amino acids, at least or about 5 amino acids, at least or about 6 amino acids, at least or about 7 amino acids, at least or about 8 amino acids, at least or about 9 amino acids, at least or about 10 amino acids, at least or about 11 amino acids, at least or about 12 amino acids, at least or about 13 amino acids, at least or about 14 amino acids, at least or about 15 amino acids, at least or about 16 amino acids, at least or about 17 amino acids, at least or about 18 amino acids, at least or about 19 amino acids, or at least or about 20 amino acids in length, or more than 20 amino acids in length. A recombinant protein fragment can be produced using any of the processes described herein.

The term "engineered protein" means a polypeptide that is not naturally encoded by an endogenous nucleic acid present within an organism (e.g., a mammal). Examples of engineered proteins include enzymes (e.g., with one or more amino acid substitutions, deletions, insertions, or additions that result in an increase in stability and/or catalytic activity of the engineered enzyme), fusion proteins, antibodies (e.g., divalent antibodies, trivalent antibodies, or a diabody), and antigen-binding proteins that contain at least one recombinant scaffolding sequence.

The term "multi-column chromatography system" or "MCCS" means a system of a total of two or more interconnected or switching chromatography columns and/or chromatographic membranes. A non-limiting example of a multi-column chromatography system is a periodic counter current chromatography system (PCC) containing a total of two or more interconnected or switching chromatography columns and/or chromatographic membranes. Additional examples of multi-column chromatography systems are described herein and are known in the art.

The term "capturing" means a step performed to partially purify or isolate (e.g., at least or about 5%, e.g., at least or about 10%, 15%, 20%, 25%, 30%, 40%, 45%, 50%, 55%, 60%, 65%, 70%, 75%, 80%, 85%, 90%, or at least or about 95% pure by weight), concentrate, and stabilize a recombinant protein (e.g., a recombinant therapeutic protein) from one or more other components present in a liquid culture medium or a diluted liquid culture medium (e.g., culture medium proteins or one or more other components (e.g., DNA, RNA, or other proteins) present in or secreted from a mammalian cell). Typically, capturing is performed using a resin that binds a recombinant protein (e.g., through the use of affinity chromatography). Non-limiting methods for capturing a recombinant protein from a liquid culture medium or diluted liquid culture medium are described herein and others are known in the art. A recombinant protein can be captured from a liquid culture medium using at least one chromatography column and/or chromatographic membrane (e.g., any of the chromatography columns and/or chromatographic membranes described herein).

The term "purifying" means a step performed to isolate a recombinant protein (e.g., a recombinant therapeutic protein) from one or more other impurities (e.g., bulk impurities) or components present in a fluid containing a recombinant protein (e.g., liquid culture medium proteins or one or more other components (e.g., DNA, RNA, other proteins, endotoxins, viruses, etc.) present in or secreted from a mammalian cell). For example, purifying can be performed during or after an initial capturing step. Purification can be performed using a resin, membrane, or any other solid support that binds either a recombinant protein or contaminants (e.g., through the use of affinity chromatography, hydrophobic interaction chromatography, anion or cation exchange chromatography, or molecular sieve chromatography). A recombinant protein can be purified from a fluid containing the recombinant protein using at least one chromatography column and/or chromatographic membrane (e.g., any of the chromatography columns or chromatographic membranes described herein).

The term "polishing" is a term of art and means a step performed to remove remaining trace or small amounts of contaminants or impurities from a fluid containing a recombinant protein (e.g., a recombinant therapeutic protein) that is close to a final desired purity. For example, polishing can be performed by passing a fluid containing the recombinant protein through a chromatographic column(s) or membrane absorber(s) that selectively binds to either the target recombinant protein or small amounts of contaminants or impurities present in a fluid containing a recombinant protein. In such an example, the eluate/filtrate of the chromatographic column(s) or membrane absorber(s) contains the recombinant protein.

The term "eluate/filtrate" is a term of art and means a fluid that is emitted from a chromatography column or chromatographic membrane that contains a detectable amount of a recombinant protein (e.g., recombinant therapeutic protein).

The term "filtering" means the removal of at least part of (e.g., at least 80%, 90%, 95%, 96%, 97%, 98%, or 99%) undesired biological contaminants (e.g., a mammalian cell, bacteria, yeast cells, viruses, or mycobacteria) and/or particulate matter (e.g., precipitated proteins) from a liquid (e.g., a liquid culture medium or fluid present in any of the systems or processes described herein).

The term "secreted protein" or "secreted recombinant protein" means a protein (e.g., a recombinant protein) that originally contained at least one secretion signal sequence when it is translated within a mammalian cell, and through, at least in part, enzymatic cleavage of the secretion signal sequence in the mammalian cell, is secreted at least partially into the extracellular space (e.g., a liquid culture medium). Skilled practitioners will appreciate that a "secreted" protein need not dissociate entirely from the cell to be considered a secreted protein.

The term "perfusion culturing" is a term of art and means the culturing of a cell culture in a vessel (e.g., a bioreactor), wherein the culturing of the cell culture in the vessel includes the periodic or continuous removal of liquid culture medium present in the vessel (e.g., liquid culture medium that is substantially fee of cells) and at the same time or shortly thereafter adding substantially the same volume of a replacement liquid culture medium to the vessel. In some examples, there is an incremental change (e.g., increase or decrease) in the volume of liquid culture medium removed and the volume of replacement culture medium added over incremental periods (e.g., an about 24-hour period, a period of between about 1 minute and about 24-hours, or a period of greater than 24 hours) during the culturing period (e.g., the culture medium refeed rate on a daily basis). The fraction of media removed and replaced each day can vary depending on the particular cells being cultured, the initial seeding density, and the cell density at a particular time. "RV" or "reactor volume" means the volume of the culture medium present at the beginning of the culturing process (e.g., the total volume of the culture medium present after seeding).

The term "vessel" is art known and means a device having an interior volume suitable for culturing a plurality of cells (e.g., recombinant mammalian cells) in a liquid culture medium under a controlled set of physical conditions that allow for the maintenance or proliferation of the cells. Non-limiting examples of vessels are bioreactors (e.g., any of the exemplary bioreactors described herein or known in the art).

The term "perfusion bioreactor" is art known and means a bioreactor having an interior volume for culturing a plurality of cells (e.g., recombinant mammalian cells) in a liquid culture medium, and having a means (e.g., an outlet, an inlet, a pump, or other such device) for periodically or continuously removing the liquid culture medium in the bioreactor and having a means (e.g., an outlet, an inlet, a pump, or other such device) for adding substantially the same volume of a replacement liquid culture medium to the bioreactor. The adding of the replacement liquid culture medium can performed at substantially the same time or shortly after the removing the liquid culture medium from the bioreactor. The means for removing the liquid culture medium from the bioreactor and the means for adding the replacement liquid culture medium can be a single device or system.

The term "production bioreactor" is a term of art and means a large-scale bioreactor (e.g., having an internal volume over 500 L, 1,000 L, 5,000 L, 10,000 L, 20,000 L, 50,000 L, or 100,000 L). For example, a production bioreactor can be a perfusion bioreactor.

The term "steady-state production cell density" is a term of art and means a target concentration of viable cells (e.g., viable recombinant mammalian cells) in a culture medium that is maintained during perfusion culturing over time.

The term "batch culturing" is a term of art and means a vessel (e.g., bioreactor) containing a plurality of cells (e.g., mammalian cells) in a liquid culture medium, wherein the culturing of the cells present in the vessel (e.g., bioreactor) does not include the addition of a substantial or significant amount of fresh liquid culture medium to the cell culture and does not include the removal of a substantial or significant amount of liquid culture medium from the cell culture during culturing.

The term "fed-batch culturing" is a term of art and means a vessel (e.g., a production bioreactor) including a plurality of cells (e.g., mammalian cells) in a liquid culture medium, wherein the culturing of the cells present in the vessel (e.g., production bioreactor) includes the periodic or continuous addition of fresh liquid culture medium to the vessel without substantial or significant removal of liquid culture medium from the vessel during culturing. The fresh liquid culture medium can be the same as the liquid culture medium present in the vessel at the start of the culturing. In some examples of fed-batch culturing, the fresh liquid culture medium is a concentrated form of the the liquid culture medium present in the vessel at the start of culturing. In some examples of fed-batch culture, the fresh culture medium is added as a dry powder.

The term "unit operation" is a term of art and means a functional step that can be performed in a process of isolating a recombinant protein (e.g., a recombinant therapeutic protein) from a liquid culture medium. For example, a unit of operation can be filtering (e.g., removal of contaminant bacteria, yeast viruses, or mycobacteria, and/or particular matter from a fluid containing a recombinant protein), capturing, epitope tag removal, purifying, holding or storing, polishing, viral inactivating, adjusting the ionic concentration and/or pH of a fluid containing the recombinant protein, and removing unwanted salts.

"Specific productivity rate" or "SPR" is a term of art and as used herein refers to the mass or enzymatic activity of a recombinant protein (e.g., recombinant therapeutic protein) produced per mammalian cell per day. The SPR for a recombinant antibody is usually measured as mass/cell/day. The SPR for a recombinant enzyme is usually measured as units/cell/day or (units/mass)/cell/day.

"Volume productivity rate" or "VPR" is a term of art and as used herein refers to the mass or enzymatic activity of recombinant protein (e.g., recombinant therapeutic protein) produced per volume of culture (e.g., per L of bioreactor, vessel, or tube volume) per day. The VPR for a recombinant antibody is usually measured as mass/L/day. The VPR for a recombinant enzyme is usually measured as units/L/day or mass/L/day.

"Skid" is a term of art and as used herein refers to a three-dimensional solid structure that can act as a platform or support for a system described herein. A skid can, if it comprises one or more structures that enable movement (e.g., wheels, rollers, or the like), confer mobility on the system or a portion thereof. Non-limiting examples of skids are described herein. Additional examples of skids are known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
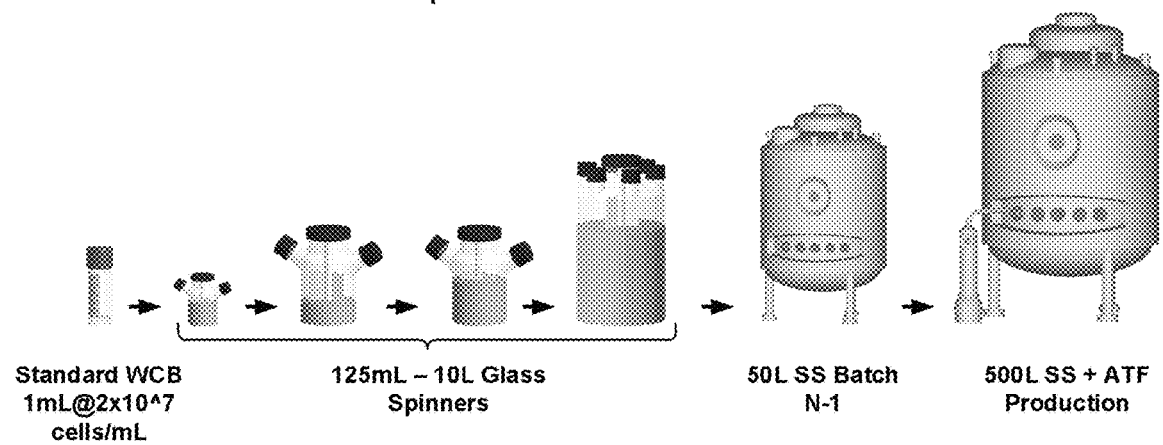
FIG. 1 is a schematic diagram showing a conventional seed train process that ends in the inoculation of a 500-L production perfusion bioreactor (top) and a schematic diagram of an exemplary seed train process provided herein that ends in the inoculation of a 500-L production perfusion bioreactor (bottom).
Figure 1:
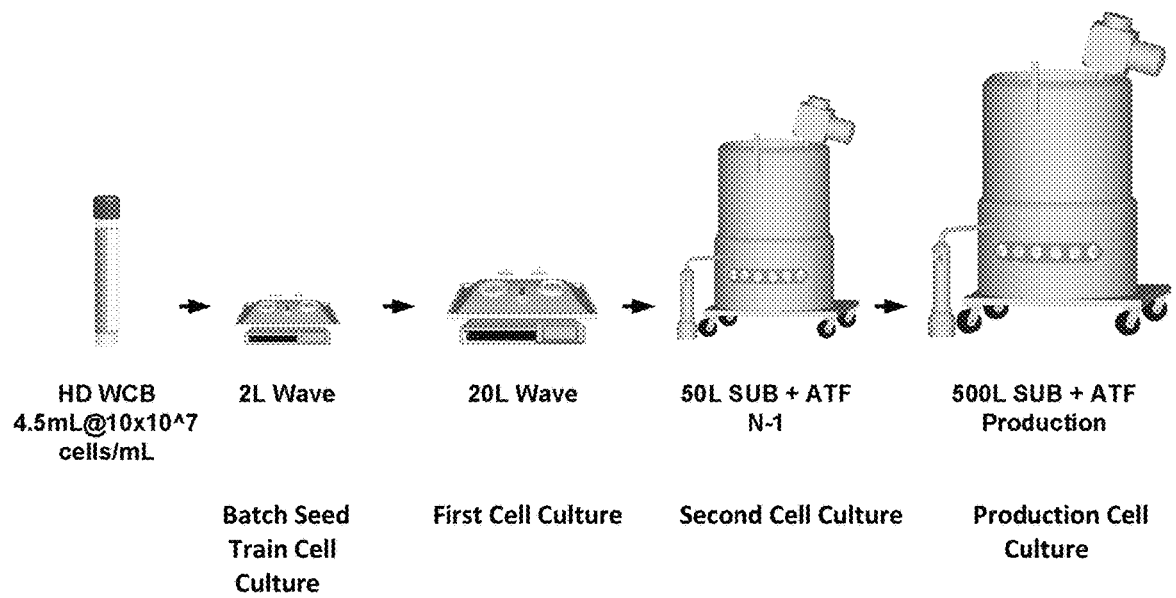

Provided herein are seed train processes that include the steps of (a) disposing a plurality of recombinant mammalian cells into a first culture medium included within a vessel to provide a first cell culture; (b) batch culturing the first cell culture to a cell density range of about 1.0×10⁶ cells/mL to about 5.0×10⁶ cells/mL; (c) disposing a volume of the first cell culture of step (b) into a second culture medium included within a perfusion bioreactor to provide a second cell culture with an initial cell density in a range of about 0.25×10⁶ cells/mL to about 0.50×10⁶ cells/mL; (d) perfusion culturing the second cell culture to a cell density range of between about 5.0×10⁶ cells/mL to about 120×10⁶ cells/mL; and (e) disposing a volume of the second cell culture of step (d) into a third culture medium included within a production bioreactor to provide a production cell culture with an initial cell density in a range of about 0.25×10⁶ cells/mL to about 8.0×10⁶ cells/mL.

The seed train processes described herein provide for many benefits. In a first aspect, the present seed train processes require less culturing steps (removal of 1 to 2 different culturing steps) prior to the provision of the production cell culture (e.g., decreasing the number of small-scale expansion stages) as compared to conventional seed train processes, which in turn provides for less manual manipulation of the cell culture and a decreased risk of contaminating the production cell culture. The seed train processes described herein can achieve an N-1 cell culture (second cell culture used to inoculate the production cell culture) with high viable cell densities, e.g., up to 100×10⁶ viable cells/mL, in 12 days without compromising culture growth characteristics in the production cell culture. The high viable cell densities achieved in the N-1 culture (second cell culture) using the seed train processes described herein allow for a higher initial cell density in the production cell culture in the production bioreactor. For example, the present seed train processes can be used to achieve an initial cell density of between about 0.50×10⁶ viable cells/mL and 10×10⁶ viable cells/mL, which in turn results in a decreased amount of time (e.g., reduction by 4-6 days) for the production cell culture to reach the steady state production cell density. This decrease in the amount of time for the production cell culture to reach the steady state production cell density can provide for a 10% increase in the overall productivity of a 50-day production culture run. The seed train processes provided herein can also result in a production cell culture that has a higher volumetric productivity rate and specific productivity rate than production cell cultures resulting from other seed train processes.

Seed Train Processes

Provided herein are seed train processes that that provide several advantages over other seed train processes. Non-limiting aspects of these seed train processes are described herein, and can be used in any combination.

Providing a First Cell Culture

The seed train processes described herein includes a step of (a) disposing a plurality of recombinant mammalian cells (e.g., any of the recombinant mammalian cells described herein or known in the art) into a first culture medium included within a vessel to provide a first cell culture. In some examples, the plurality of recombinant mammalian cells disposed into the first culture medium can be between about 4.5×10⁷ cells and about 450×10⁷ cells (e.g., between about 9.0×10⁷ cells and about 450×10⁷ cells, between about 22.5×10⁷ cells and about 450×10⁷ cells, between about 45×10⁷ cells and about 450×10⁷ cells, between about 67.5×10⁷ cells and about 450×10⁷ cells, between about 90×10⁷ cells and about 450×10⁷ cells, between about 112.5×10⁷ cells and about 450×10⁷ cells, between about 135×10⁷ cells and about 450×10⁷ cells, between about 157.5×10⁷ cells and about 450×10⁷ cells, between about 180×10⁷ and about 450×10⁷ cells, between about 4.5×10⁷ cells and about 405×10⁷ cells, between about 9.0×10⁷ cells and about 405×10⁷ cells, between about 22.5×10⁷ cells and about 405×10⁷ cells, between about 45×10⁷ and about 405×10⁷ cells, between about 67.5×10⁷ cells and about 405×10⁷ cells, between about 90×10⁷ and about 405×10⁷ cells, between about 112.5×10⁷ and about 405×10⁷ cells, between about 135×10⁷ cells and about 405×10⁷ cells, between about 157.5×10⁷ cells and about 405×10⁷ cells, between about 180×10⁷ cells and about 405×10⁷ cells, between about 4.5×10⁷ cells and about 360×10⁷ cells, between about 9.0×10⁷ cells and about 360×10⁷ cells, between about 22.5×10⁷ cells and about 360×10⁷ cells, between about 45×10⁷ cells and about 360×10⁷ cells, between about 67.5×10⁷ cells and about 360×10⁷ cells, between about 90×10⁷ cells and about 360×10⁷ cells, between about 112.5×10⁷ cells and about 360×10⁷ cells, between about 135×10⁷ cells and about 360×10⁷ cells, between about 157.5×10⁷ cells and about 360×10⁷ cells, between about 180×10⁷ cells and about 360×10⁷ cells, between about 4.5×10⁷ cells and about 315×10⁷ cells, between about 9.0×10⁷ cells and about 315×10⁷ cells/mL, between about 22.5×10⁷ cells and about 315×10⁷ cells, between about 45×10⁷ cells and about 315×10⁷ cells, between about 67.5×10⁷ cells and about 315×10⁷ cells, between about $90\times10^7$ cells and about $315\times10^7$ cells, between about $112.5\times10^7$ cells to about $315\times10^7$ cells, between about $135\times10^7$ cells and about $315\times10^7$ cells, between about $157.5\times10^7$ cells and about $315\times10^7$ cells, between about $180\times10^7$ cells and about $315\times10^7$ cells, between about $4.5\times10^7$ cells and about $270\times10^7$ cells, between about $9.0\times10^7$ cells and about $270\times10^7$ cells, between about $22.5\times10^7$ cells and about $270\times10^7$ cells, between about $45\times10^7$ cells and about $270\times10^7$ cells, between about $67.5\times10^7$ cells and about $270\times10^7$ cells, between about $90\times10^7$ cells and about $270\times10^7$ cells, between about $112.5\times10^7$ cells and about $270\times10^7$ cells, between about $135\times10^7$ cells and about $270\times10^7$ cells, between about $157.5\times10^7$ cells and about $270\times10^7$ cells, between about $180\times10^7$ cells and about $270\times10^7$ cells, between about $4.5\times10^7$ cells and about $225\times10^7$ cells, between about $9.0\times10^7$ cells and about $225\times10^7$ cells, between about $22.5\times10^7$ cells and about $225\times10^7$ cells, between about $45\times10^7$ cells and about $225\times10^7$ cells, between about $67.5\times10^7$ cells and about $225\times10^7$ cells, between about $90\times10^7$ cells and about $225\times10^7$ cells, between about $112.5\times10^7$ cells and about $225\times10^7$ cells, between $135\times10^7$ cells and about $225\times10^7$ cells, between about $4.5\times10^7$ cells and about $180\times10^7$ cells, between about $9.0\times10^7$ cells and about $180\times10^7$ cells, between about $22.5\times10^7$ and about $180\times10^7$ cells, between about $45\times10^7$ cells and about $180\times10^7$ cells, between about $67.5\times10^7$ and about $180\times10^7$ cells, between about $90\times10^7$ and about $180\times10^7$ cells, between about $4.5\times10^7$ cells and about $135\times10^7$ cells, between about $9.0\times10^7$ and about $135\times10^7$ cells, between about $22.5\times10^7$ cells and about $135\times10^7$ cells, between about $45\times10^7$ cells and about $135\times10^7$ cells, between about $4.5\times10^7$ cells and about $90\times10^7$ cells, between about $9.0\times10^7$ cells and about $90\times10^7$ cells, between about $22.5\times10^7$ cells and about $90\times10^7$ cells, or between about $45\times10^7$ and about $90\times10^7$ cells) and can vary depending on the volume of first culture medium contained within the vessel. For example, the plurality of cells disposed in the first liquid culture medium can be sufficient to result in an initial cell density of between about $0.10\times10^6$ cells/mL and about $0.80\times10^6$ cells/mL (e.g., between about $0.10\times10^6$ cells/mL and about $0.75\times10^6$ cells/mL, between about $0.10\times10^6$ cells/mL and $0.70\times10^6$ cells/mL, between about $0.10\times10^6$ cells/mL and about $0.65\times10^6$ cells/mL, between about $0.10\times10^6$ cells/mL and about $0.60\times10^6$ cells/mL, between about $0.10\times10^6$ cells/mL and about $0.55\times10^6$ cells/mL, between about $0.10\times10^6$ cells/mL and about $0.50\times10^6$ cells/mL, between about $0.10\times10^6$ cells/mL and about $0.45\times10^6$ cells/mL, between about $0.10\times10^6$ cells/mL and about $0.40\times10^6$ cells/mL, between about $0.10\times10^6$ cells/mL and about $0.35\times10^6$ cells/mL, between about $0.10\times10^6$ cells/mL and about $0.30\times10^6$ cells/mL, between about $0.15\times10^6$ cells/mL and about $0.80\times10^6$ cells/mL, between about $0.15\times10^6$ cells/mL and about $0.75\times10^6$ cells/mL, between about $0.15\times10^6$ cells/mL and about $0.70\times10^6$ cells/mL, between about $0.15\times10^6$ cells/mL and about $0.65\times10^6$ cells/mL, between about $0.15\times10^6$ cells/mL and about $0.60\times10^6$ cells/mL, between about $0.15\times10^6$ cells/mL and about $0.55\times10^6$ cells/mL, between about $0.15\times10^6$ cells/mL and about $0.50\times10^6$ cells/mL, between about $0.15\times10^6$ cells/mL and about $0.45\times10^6$ cells/mL, between about $0.15\times10^6$ cells/mL and about $0.40\times10^6$ cells/mL, between about $0.15\times10^6$ cells/mL and about $0.35\times10^6$ cells/mL, between about $0.20\times10^6$ cells/mL and about $0.80\times10^6$ cells/mL, between about $0.20\times10^6$ cells/mL and about $0.75\times10^6$ cells/mL, between about $0.20\times10^6$ cells/mL and about $0.70\times10^6$ cells/mL, between about $0.20\times10^6$ cells/mL and about $0.65\times10^6$ cells/mL, between about $0.20\times10^6$ cells/mL and about $0.60\times10^6$ cells/mL, between about $0.20\times10^6$ cells/mL and about $0.55\times10^6$ cells/mL, between about $0.20\times10^6$ cells/mL and about $0.50\times10^6$ cells/mL, between about $0.20\times10^6$ cells/mL and about $0.45\times10^6$ cells/mL, between about $0.20\times10^6$ cells/mL and about $0.40\times10^6$ cells/mL, between about $0.25\times10^6$ cells/mL and about $0.75\times10^6$ cells/mL, between about $0.25\times10^6$ cells/mL and about $0.70\times10^6$ cells/mL, between about $0.25\times10^6$ cells/mL and about $0.65\times10^6$ cells/mL, between about $0.25\times10^6$ cells/mL and about $0.60\times10^6$ cells/mL, between about $0.25\times10^6$ cells/mL and about $0.55\times10^6$ cells/mL, between about $0.25\times10^6$ cells/mL and about $0.50\times10^6$ cells/mL, between about $0.25\times10^6$ cells/mL and about $0.45\times10^6$ cells/mL, between about $0.25\times10^6$ cells/mL and about $0.40\times10^6$ cells/mL, between about $0.25\times10^6$ cells/mL and about $0.35\times10^6$ cells/mL, between about $0.30\times10^6$ cells/mL and about $0.80\times10^6$ cells/mL, between about $0.30\times10^6$ cells/mL and about $0.75\times10^6$ cells/mL, between about $0.30\times10^6$ cells/mL and about $0.70\times10^6$ cells/mL, between about $0.30\times10^6$ cells/mL and about $0.65\times10^6$ cells/mL, between about $0.30\times10^6$ cells/mL and about $0.60\times10^6$ cells/mL, between about $0.30\times10^6$ cells/mL and about $0.55\times10^6$ cells/mL, between about $0.30\times10^6$ cells/mL and about $0.50\times10^6$ cells/mL, between about $0.30\times10^6$ cells/mL and about $0.45\times10^6$ cells/mL, or between about $0.30\times10^6$ and about $0.40\times10^6$ cells/mL) in the first cell culture.

As can be appreciated in the art, the vessel in step (a) can have a variety of different volumes. For example, the vessel in step (a) including the first culture medium can have an internal volume of between about 0.50 L to about 200 L (e.g., between about 0.50 L and about 180 L, between about 0.50 L and about 160 L, between about 0.50 L and about 140 L, between about 0.50 L and about 120 L, between about 0.50 L and about 100 L, between about 0.50 L and about 90 L, between about 0.50 L and about 80 L, between about 0.50 L and about 70 L, between about 0.50 L and about 60 L, between about 0.50 L and about 50 L, between about 0.50 L and about 40 L, between about 0.50 L and about 30 L, between about 0.50 L and about 20 L, between about 0.50 L and about 10 L, between about 0.50 L and about 5.0 L, between about 1.0 L and about 200 L, between about 1.0 L and about 180 L, between about 1.0 L and about 160 L, between about 1.0 L and about 140 L, between about 1.0 L and about 120 L, between about 1.0 L and about 100 L, between about 1.0 L and about 90 L, between about 1.0 L and about 80 L, between about 1.0 L and about 70 L, between about 1.0 L and about 60 L, between about 1.0 L and about 50 L, between about 1.0 L and about 40 L, between about 1.0 L and about 30 L, between about 1.0 L and about 20 L, between about 1.0 L and about 10 L, between about 1.0 L and about 5.0 L, between about 1.5 L and about 200 L, between about 1.5 L and about 180 L, between about 1.5 L and about 160 L, between about 1.5 L and about 140 L, between about 1.5 L and about 120 L, between about 1.5 L and about 100 L, between about 1.5 L and about 90 L, between about 1.5 L and about 80 L, between about 1.5 L and about 70 L, between about 1.5 L and about 60 L, between about 1.5 L and about 50 L, between about 1.5 L and about 40 L, between about 1.5 L and about 30 L, between about 1.5 L and about 20 L, between about 1.5 L and about 10 L, between about 1.5 L and about 5.0 L, between about 2.0 L and about 200 L, between about 2.0 L and about 180 L, between about 2.0 L and about 160 L, between about 2.0 L and about 140 L, between about 2.0 L and about 120 L, between about 2.0 L and about 100 L, between about 2.0 L and about 90 L, between about 2.0 L and about 80 L, between about 2.0 L and about 70 L, between about 2.0 L and about 60 L, between about 2.0 L and about 50 L, between about 2.0 L and about 40 L, between about 2.0 L and about 30 L, between about 2.0 L and about 20 L, between about 2.0 L and about 10 L, between about 2.0 L and about 5.0 L, between about 2.5 L and about 200 L, between about 2.5 L and about 180 L, between about 2.5 L and about 160 L, between about 2.5 L and about 140 L, between about 2.5 L and about 120 L, between about 2.5 L and about 100 L, between about 2.5 L and about 90 L, between about 2.5 L and about 80 L, between about 2.5 L and about 70 L, between about 2.5 L and about 60 L, between about 2.5 L and about 50 L, between about 2.5 L and about 50 L, between about 2.5 L and about 40 L, between about 2.5 L and about 30 L, between about 2.5 L and about 20 L, between about 2.5 L and about 10 L, between about 2.5 L and about 5.0 L, between about 5.0 L and about 200 L, between about 5.0 L and about 180 L, between about 5.0 L and about 160 L, between about 5.0 L and about 140 L, between about 5.0 L and about 120 L, between about 5.0 L and about 100 L, between about 5.0 L and about 90 L, between about 5.0 L and about 80 L, between about 5.0 L and about 70 L, between about 5.0 L and about 60 L, between about 5.0 L and about 50 L, between about 5.0 L and about 40 L, between about 5.0 L and about 30 L, between about 5.0 L and about 20 L, or between about 5.0 L and about 10 L).

As can be appreciated in the art, the vessel that contains the first cell culture can be any apparatus used in the art for the purpose of culturing mammalian cells (e.g., a flask (e.g., a spin flask), a rolling tube, or a bioreactor). The vessel can include an internal means for agitation (e.g., an impeller) or the vessel can be agitated externally (e.g., through the use of a rotating and/or tilting platform). The vessel can be made of stainless steel or plastic (e.g., a plastic sterile bag). In some embodiments, the vessel can be a disposable single-use bioreactor (e.g., a Millipore™ Mobius® Cellready 3 L disposable bioreactor, Pierre Guerin ATM1 Nucleo™ 20 L disposable bioreactor, a Sartorius Cultibag STR™ 50 L disposable bioreactor, a Sartorius Cultibag RM™ 20 L, Sartorius Cultibag Orbital™ 50 L, GE Wave Bioreactor 2/10 System 5 L, GE Wave Bioreactor 20/50 System 25 L, GE Wave Bioreactor 200 System 200 L, or GE Wave Bioreactor 500/1000 System 500 L). The interior surface of the vessel may have at least one coating (e.g., at least one coating of gelatin, collagen, poly-L-ornithine, polystyrene, and laminin), and as is known in the art, one or more ports for the sparging of $O_2$, $CO_2$, and $N_2$ into the first liquid culture medium. The vessel can be equipped with one or more sensor probe(s). When the vessel is composed of a non-rigid plastic material (e.g., a plastic sterile bag), the vessel can be connected to an exterior support that surrounds and supports the vessel.

The first cell culture can have a variety of different volumes, for example first cell culture can have a volume of between about 0.30 L and about 100 L (e.g., between about 0.30 L and about 90 L, between about 0.30 L and about 80 L, between about 0.30 L and about 70 L, between about 0.30 L and about 60 L, between about 0.30 L and about 50 L, between about 0.30 L and about 40 L, between about 0.30 L and about 30 L, between about 0.30 L and about 20 L, between about 0.30 L and about 10 L, between about 0.30 L and about 5.0 L, between about 0.50 L and about 100 L, between about 0.50 L and about 90 L, between about 0.50 L and about 80 L, between about 0.50 L and about 70 L, between about 0.50 L and about 60 L, between about 0.50 L and about 50 L, between about 0.50 L and about 40 L, between about 0.50 L and about 30 L, between about 0.50 L and about 20 L, between about 0.50 L and about 10 L, between about 0.50 L and about 5.0 L, between about 1.0 L and about 100 L, between about 1.0 L and about 90 L, between about 1.0 L and about 80 L, between about 1.0 L and about 70 L, between about 1.0 L and about 60 L, between about 1.0 L and about 50 L, between about 1.0 L and about 40 L, between about 1.0 L and about 30 L, between about 1.0 L and about 20 L, between about 1.0 L and about 10 L, between about 1.0 L and about 5.0 L, between about 1.5 L and about 100 L, between about 1.5 L and about 90 L, between about 1.5 L and about 80 L, between about 1.5 L and about 70 L, between about 1.5 L and about 60 L, between about 1.5 L and about 50 L, between about 1.5 L and about 40 L, between about 1.5 L and about 30 L, between about 1.5 L and about 20 L, between about 1.5 L and about 10 L, between about 1.5 L and about 5.0 L, between about 2.0 L and about 100 L, between about 2.0 L and about 90 L, between about 2.0 L and about 80 L, between about 2.0 L and about 70 L, between about 2.0 L and about 60 L, between about 2.0 L and about 50 L, between about 2.0 L and about 40 L, between about 2.0 L and about 30 L, between about 2.0 L and about 20 L, between about 2.0 L and about 10 L, between about 2.0 L and about 5.0 L, between about 2.5 L and about 100 L, between about 2.5 L and about 90 L, between about 2.5 L and about 80 L, between about 2.5 L and about 70 L, between about 2.5 L and about 60 L, between about 2.5 L and about 50 L, between about 2.5 L and about 40 L, between about 2.5 L and about 30 L, between about 2.5 L and about 20 L, between about 2.5 L and about 10 L, between about 2.5 L and about 5.0 L, between about 5.0 L and about 100 L, between about 5.0 L and about 90 L, between about 5.0 L and about 80 L, between about 5.0 L and about 70 L, between about 5.0 L and about 60 L, between about 5.0 L and about 50 L, between about 5.0 L and about 40 L, between about 5.0 L and about 30 L, between about 5.0 L and about 20 L, or between about 5.0 L and about 10 L).

As can be appreciated in the art, there are many ways that a plurality of cells can be disposed into a first culture medium contained with a vessel. For example, disposing the plurality of recombinant mammalian cells can include the steps of thawing a frozen cell bank (e.g., any of the exemplary frozen cell banks described herein or known in the art) and disposing (e.g., sterile pipetting) a volume of the thawed cell bank into the first culture medium. A frozen cell bank can have a cell density range, e.g., of between about $1.0 \times 10^7$ cells/mL and about $100 \times 10^7$ cells/mL (e.g., between about $2.0 \times 10^7$ cells/mL and about $100 \times 10^7$ cells/mL, between about $5.0 \times 10^7$ cells/mL and about $100 \times 10^7$ cells/mL, between about $10 \times 10^7$ cells/mL and about $100 \times 10^7$ cells/mL, between about $15 \times 10^7$ cells/mL and about $100 \times 10^7$ cells/mL, between about $20 \times 10^7$ cells/mL and about $100 \times 10^7$ cells/mL, between about $25 \times 10^7$ cells/mL and about $100 \times 10^7$ cells/mL, between about $30 \times 10^7$ cells/mL and about $100 \times 10^7$ cells/mL, between about $35 \times 10^7$ cells/mL and about $100 \times 10^7$ cells/mL, between about $40 \times 10^7$ cells/mL and about $100 \times 10^7$ cells/mL, between about $1.0 \times 10^7$ cells/mL and about $90 \times 10^7$ cells/mL, between about $2.0 \times 10^7$ cells/mL and about $90 \times 10^7$ cells/mL, between about $5.0 \times 10^7$ cells/mL and about $90 \times 10^7$ cells/mL, between about $10 \times 10^7$ cells/mL and about $90 \times 10^7$ cells/mL, between about $15 \times 10^7$ cells/mL and about $90 \times 10^7$ cells/mL, between about $20 \times 10^7$ cells/mL and about $90 \times 10^7$ cells/mL, between about $25 \times 10^7$ cells/mL and about $90 \times 10^7$ cells/mL, between about $30 \times 10^7$ cells/mL and about $90 \times 10^7$ cells/mL, between about $35 \times 10^7$ cells/mL and about $90 \times 10^7$ cells/mL, between about $40 \times 10^7$ cells/mL and about 90×10$^7$ cells/mL, between about 1.0×10$^7$ cells/mL and about 80×10$^7$ cells/mL, between about 2.0×10$^7$ cells/mL and about 80×10$^7$ cells/mL, between about 5.0×10$^7$ cells/mL and about 80×10$^7$ cells/mL, between about 10×10$^7$ and about 80×10$^7$ cells/mL, between about 15×10$^7$ cells/mL and about 80×10$^7$ cells/mL, between about 20×10$^7$ cells/mL and about 80×10$^7$ cells/mL, between about 25×10$^7$ cells/mL and about 80×10$^7$ cells/mL, between about 30×10$^7$ cells/mL and about 80×10$^7$ cells/mL, between about 35×10$^7$ cells/mL and about 80×10$^7$ cells/mL, between about 40×10$^7$ cells/mL and about 80×10$^7$ cells/mL, between about 1.0×10$^7$ cells/mL and about 70×10$^7$ cells/mL, between about 2.0×10$^7$ cells/mL and about 70×10$^7$ cells/mL, between about 5.0×10$^7$ cells/mL and about 70×10$^7$ cells/mL, between about 10×10$^7$ cells/mL and about 70×10$^7$ cells/mL, between about 15×10$^7$ cells/mL and about 70×10$^7$ cells/mL, between about 20×10$^7$ cells/mL and about 70×10$^7$ cells/mL, between about 25×10$^7$ cells/mL and about 70×10$^7$ cells/mL, between about 30×10$^7$ cells/mL and about 70×10$^7$ cells/mL, between about 35×10$^7$ cells/mL and about 70×10$^7$ cells/mL, between about 40×10$^7$ cells/mL and about 70×10$^7$ cells/mL, between about 1.0×10$^7$ cells/mL and about 60×10$^7$ cells/mL, between about 2.0×10$^7$ cells/mL and about 60×10$^7$ cells/mL, between about 5.0×10$^7$ and about 60×10$^7$ cells/mL, between about 10×10$^7$ cells/mL and about 60×10$^7$ cells/mL, between about 15×10$^7$ cells/mL and about 60×10$^7$ cells/mL, between about 20×10$^7$ cells/mL and about 60×10$^7$ cells/mL, between about 25×10$^7$ cells/mL and about 60×10$^7$ cells/mL, between about 30×10$^7$ and about 60×10$^7$ cells/mL, between about 35×10$^7$ cells/mL and about 60×10$^7$ cells/mL, between about 40×10$^7$ cells/mL and about 60×10$^7$ cells/mL, between about 1.0×10$^7$ cells/mL and about 50×10$^7$ cells/mL, between about 2.0×10$^7$ cells/mL and about 50×10$^7$ cells/mL, between about 5.0×10$^7$ cells/mL and about 50×10$^7$ cells/mL, between about 10×10$^7$ cells/mL and about 50×10$^7$ cells/mL, between about 15×10$^7$ cells/mL and about 50×10$^7$ cells/mL, between about 20×10$^7$ cells/mL and about 50×10$^7$ cells/mL, between about 25×10$^7$ cells/mL and about 50×10$^7$ cells/mL, or between about 30×10$^7$ cells/mL and about 50×10$^7$ cells/mL). Methods for generating such frozen cell banks are known in the art (see, e.g., U.S. Provisional Patent Application Ser. No. 61/793,021, filed Mar. 15, 2013; U.S. patent application Ser. No. 14/212,607, filed Mar. 14, 2014; and International Application No. PCT/US2014/027757, filed Mar. 14, 2014). As is well known in the art, thawing a frozen cell bank can be performed, e.g., by exposing the frozen cell bank to a heating element (other than exposure to room temperature), e.g., a water bath or block heater (e.g., set at 30° C. or 37° C.). In some examples, the thawing can be performed over a period of between 1 second and 1 minute, between 1 second and 55 seconds, between 1 second and 50 seconds, between 1 second and 45 seconds, between 1 second and 40 seconds, between 1 second and 35 seconds, between 1 second and 30 seconds, between 1 second and 25 seconds, or between 1 second and 20 seconds). A frozen cell bank can also be thawed by exposing the frozen cell bank to room temperature (e.g., about 25° C.). The thawed cell bank can contain a percentage of viable cells, e.g., of at least 60% (e.g., at least 65%, at least 70%, at least 75%, at least 80%, at least 85%, at least 90%, at least 95%, or at least 98%). For example, a thawed cell bank can contain a percentage of viable cells between 60% and about 98% (e.g., between about 60% and about 95%, between about 60% and about 90%, between about 60% and about 85%, between about 60% and about 80%, between about 60% and about 75%, between about 60% and about 70%, between about 65% and about 98%, between about 65% and about 95%, between about 65% and about 90%, between about 65% and about 85%, between about 65% and about 80%, between about 65% and about 75%, between about 70% and about 98%, between about 70% and about 95%, between about 70% and about 90%, between about 70% and about 85%, between about 70% and about 80%, between about 80% and about 98%, between about 80% and about 95%, between about 80% and about 90%, between about 85% and about 98%, between about 85% and about 95%, between about 90% and about 98%, or between about 90% and about 95%).

In some examples, the disposing of a plurality of recombinant mammalian cells into the first culture medium to generate the first cell culture can include the step of disposing a volume of a third cell culture comprising the plurality of recombinant mammalian cells into the first culture medium. For example, the volume of the third cell culture that is disposed into the first culture medium can be, e.g., between 0.10 mL and about 10 L (e.g., between about 0.10 mL and about 8.0 L, between about 0.10 mL and about 6.0 L, between about 0.10 mL and about 4.0 L, between about 0.10 mL and about 2.0 L, between about 0.10 mL and about 1.0 L, between about 0.10 mL and about 800 mL, between about 0.10 mL and about 600 mL, between about 0.10 mL and about 400 mL, between about 0.10 mL and about 200 mL, between about 0.10 mL and about 100 mL, between about 0.10 mL and about 50 mL, between about 0.10 mL and about 25 mL, between about 0.10 mL and about 10 mL, between about 0.50 mL and about 10 L, between about 0.50 mL and about 8.0 L, between about 0.50 mL and about 6.0 L, between about 0.50 mL and about 4.0 L, between about 0.50 mL and about 2.0 L, between about 0.50 mL and about 1.0 L, between about 0.50 mL and about 1.0 L, between about 0.50 mL and about 800 mL, between about 0.50 mL and about 600 mL, between about 0.50 mL and about 400 mL, between about 0.50 mL and about 200 mL, between about 0.50 mL and about 100 mL, between about 0.50 mL and about 50 mL, between about 0.50 mL and about 50 mL, between about 0.50 mL and about 25 mL, between about 1.0 mL and about 10 L, between about 1.0 mL and about 8.0 L, between about 1.0 mL and about 6.0 L, between about 1.0 mL and about 4.0 L, between about 1.0 mL and about 2.0 L, between about 1.0 mL and about 1.0 L, between about 1.0 mL and about 800 mL, between about 1.0 mL and about 600 mL, between about 1.0 mL and about 400 mL, between about 1.0 mL and about 200 mL, between about 0.10 mL and about 100 mL, between about 1.0 mL and about 50 mL, between about 1.0 mL and about 25 mL, between about 2.0 mL and about 10 L, between about 2.0 mL and about 8.0 L, between about 2.0 mL and about 6.0 L, between about 2.0 mL and about 4.0 L, between about 2.0 mL and about 2.0 L, between about 2.0 mL and about 1.0 L, between about 2.0 mL and about 800 mL, between about 2.0 mL and about 600 mL, between about 2.0 mL and about 400 mL, between about 2.0 mL and about 200 mL, between about 2.0 mL and about 100 mL, between about 2.0 mL and about 50 mL, between about 2.0 mL and about 25 mL, between about 5.0 mL and about 10 L, between about 5.0 mL and about 8.0 L, between about 5.0 mL and about 6.0 L, between about 5.0 mL and about 4.0 L, between about 5.0 mL and about 2.0 L, between about 5.0 mL and about 1.0 L, between about 5.0 mL and about 800 mL, between about 5.0 mL and about 600 mL, between about 5.0 mL and about 400 mL, between about 5.0 mL and about 200 mL, between about 5.0 mL and about 100 mL, between about 5.0 mL and about 50 mL, between about 5.0 mL and about 25.0 mL, between about 10.0 mL and about 10 L, between about 10.0 mL and about 8.0 L, between about 10.0 mL and about 6.0 L, between about 10.0 mL and about 4.0 L, between about 10.0 mL and about 2.0 L, between about 10.0 mL and about 1.0 L, between about 10.0 mL and about 800 mL, between about 10.0 mL and about 600 mL, between about 10.0 mL and about 400 mL, between about 10.0 mL and about 200 mL, between about 10.0 mL and about 100 mL, between about 10.0 mL and about 50 mL, or between about 10.0 mL and about 25.0 mL). The cell density of the third cell culture disposed into the first culture medium can be any of the exemplary cell densities or cell density ranges described herein. As can be appreciated by one in the art, the volume of third cell culture sufficient to generate a first cell culture with an initial cell density of between about $0.10 \times 10^6$ cells/mL to about $0.80 \times 10^6$ cells/mL (or any of the other exemplary ranges of initial cell densities listed for the first cell culture above) can be determined from the cell density of the third cell culture and the volume of the first liquid culture medium present in the vessel (prior to disposing the third cell culture into the first culture medium).

Some embodiments that use a third cell culture can include the steps of (1) disposing a plurality of the recombinant mammalian cells into a fourth culture medium included within a vessel to provide a third cell culture, and (2) batch culturing the third cell culture of (1) to a cell density range of between about $1.0 \times 10^6$ cells/mL and about $15.0 \times 10^6$ cells/mL (e.g., between about $1.0 \times 10^6$ cells/mL and about $12.5 \times 10^6$ cells/mL, between about $1.0 \times 10^6$ cells/mL and about $10.0 \times 10^6$ cells/mL, between about $1.0 \times 10^6$ cells/mL and about $7.5 \times 10^6$ cells/mL, between about $1.0 \times 10^6$ cells/mL and about $5.0 \times 10^6$ cells/mL, between about $1.0 \times 10^6$ cells/mL and about $2.5 \times 10^6$ cells/mL, between about $1.5 \times 10^6$ cells/mL and about $15.0 \times 10^6$ cells/mL, between about $1.5 \times 10^6$ cells/mL and about $12.5 \times 10^6$ cells/mL, between about $1.5 \times 10^6$ cells/mL and about $10 \times 10^6$ cells/mL, between about $1.5 \times 10^6$ cells/mL and about $7.5 \times 10^6$ cells/mL, between about $1.5 \times 10^6$ cells/mL and about $5.0 \times 10^6$ cells/mL, between about $1.5 \times 10^6$ cells/mL and about $2.5 \times 10^6$ cells/mL, between about $2.0 \times 10^6$ cells/mL and about $15 \times 10^6$ cells/mL, between about $2.0 \times 10^6$ cells/mL and about $12.5 \times 10^6$ cells/mL, between about $2.0 \times 10^6$ cells/mL and about $10 \times 10^6$ cells/mL, between about $2.0 \times 10^6$ cells/mL and about $7.5 \times 10^6$ cells/mL, between about $2.0 \times 10^6$ cells/mL and about $5.0 \times 10^6$ cells/mL, between about $2.0 \times 10^6$ cells/mL and about $2.5 \times 10^6$ cells/mL, between about $2.5 \times 10^6$ cells/mL and about $15 \times 10^6$ cells/mL, between about $2.5 \times 10^6$ cells/mL and about $12.5 \times 10^6$ cells/mL, between about $2.5 \times 10^6$ cells/mL and about $10 \times 10^6$ cells/mL, between about $2.5 \times 10^6$ cells/mL and about $7.5 \times 10^6$ cells/mL, between about $2.5 \times 10^6$ cells/mL and about $5.0 \times 10^6$ cells/mL, between about $5.0 \times 10^6$ cells/mL and about $15 \times 10^6$ cells/mL, between about $5.0 \times 10^6$ cells/mL and about $12.5 \times 10^6$ cells/mL, between about $5.0 \times 10^6$ cells/mL and about $10 \times 10^6$ cells/mL, between about $5.0 \times 10^6$ cells/mL and about $7.5 \times 10^6$ cells/mL, between about $7.5 \times 10^6$ cells/mL and about $15 \times 10^6$ cells/mL, between about $7.5 \times 10^6$ cells/mL and about $12.5 \times 10^6$ cells/mL, between about $7.5 \times 10^6$ cells/mL and about $10 \times 10^6$ cells/mL, between about $10 \times 10^6$ cells/mL and about $15 \times 10^6$ cells/mL, or between about $10 \times 10^6$ cells/mL and about $12.5 \times 10^6$ cells/mL), where a volume of the third cell culture in (2) is then disposed into the first culture medium to generate the first cell culture. The plurality of cells disposed into the fourth culture medium can be, e.g., between about $0.10 \times 10^7$ cells and about $20 \times 10^7$ cells (e.g., between about $0.10 \times 10^7$ cells and about $15 \times 10^7$ cells, between about $0.10 \times 10^7$ cells and about $10 \times 10^7$ cells, between about $0.10 \times 10^7$ cells and about $5.0 \times 10^7$ cells, between about $0.10 \times 10^7$ cells and about $2.0 \times 10^7$ cells, between about $0.10 \times 10^7$ cells and about $1.0 \times 10^7$ cells, between about $0.10 \times 10^7$ cells and about $0.50 \times 10^7$ cells, between about $0.20 \times 10^7$ cells and about $20 \times 10^7$ cells, between about $0.20 \times 10^7$ cells and about $15 \times 10^7$ cells, between about $0.20 \times 10^7$ cells and about $10 \times 10^7$ cells, between about $0.20 \times 10^7$ cells and about $5.0 \times 10^7$ cells, between about $0.20 \times 10^7$ cells and about $2.0 \times 10^7$ cells, between about $0.20 \times 10^7$ cells to about $1.0 \times 10^7$ cells, between about $0.20 \times 10^7$ cells and about $0.50 \times 10^7$ cells, between about $0.40 \times 10^7$ cells and about $20 \times 10^7$ cells, between about $0.40 \times 10^7$ cells and about $15 \times 10^7$ cells, between about $0.40 \times 10^7$ cells to about $10 \times 10^7$ cells, between about $0.40 \times 10^7$ cells and about $5.0 \times 10^7$ cells, between about $0.40 \times 10^7$ cells and about $2.0 \times 10^7$ cells, between about $0.40 \times 10^7$ cells and about $1.0 \times 10^7$ cells, between about $0.60 \times 10^7$ cells and about $20 \times 10^7$ cells, between about $0.60 \times 10^7$ cells and about $15 \times 10^7$ cells, between about $0.60 \times 10^7$ cells and about $10 \times 10^7$ cells, between about $0.60 \times 10^7$ cells and about $5 \times 10^7$ cells, between about $0.60 \times 10^7$ cells and about $2 \times 10^7$ cells, between about $0.60 \times 10^7$ cells and about $1 \times 10^7$ cells, between about $0.80 \times 10^7$ cells and about $1.0 \times 10^7$ cells, between about $1.0 \times 10^7$ cells and about $20 \times 10^7$ cells, between about $1.0 \times 10^7$ cells and about $15 \times 10^7$ cells, between about $1.0 \times 10^7$ cells and about $10 \times 10^7$ cells, between about $1.0 \times 10^7$ cells and about $5.0 \times 10^7$ cells, between about $1.0 \times 10^7$ cells and about $2.0 \times 10^7$ cells, between about $5.0 \times 10^7$ cells and about $20 \times 10^7$ cells, between about $5.0 \times 10^7$ cells and about $15 \times 10^7$ cells, or between about $5.0 \times 10^7$ cells and about $10 \times 10^7$ cells) and can vary depending on the volume of fourth culture medium contained within the vessel. For example, the plurality of cells disposed in the fourth culture medium can be sufficient to result in an initial cell density of between about $0.10 \times 10^6$ cells/mL to about $0.80 \times 10^6$ cells/mL in the third cell culture (e.g., any of the exemplary initial cell densities or ranges of initial cell densities listed above for the first cell culture).

In some embodiments, the step of disposing the plurality of recombinant mammalian cells into the fourth culture medium to generate the third cell culture can include the steps of thawing a frozen cell bank and disposing a volume of the thawed cell bank into the fourth culture medium. In such embodiments, the frozen cell bank can have any of the cell densities or ranges of cell densities for frozen cell banks described herein. The frozen cell bank can be thawed using any of the methods described herein or known in the art. The resulting thawed cell bank can have any of the percentages of viable cells or any of the ranges of percentages of viable cells for a thawed cell bank described herein.

The internal volume of the vessel containing the third cell culture can be, e.g., between about 0.20 L and about 30 L (e.g., between about 0.20 L and about 20 L, between about 0.20 L and about 10 L, between about 0.20 L and about 5.0 L, between about 0.20 L and about 2.5 L, between about 0.50 L and about 30 L, between about 0.50 L and about 20 L, between about 0.50 L and about 10 L, between about 0.50 L and about 5.0 L, between about 0.50 L and about 2.5 L, between about 1.0 L and about 30 L, between about 1.0 L and about 20 L, between about 1.0 L and about 10 L, between about 1.0 L and about 5.0 L, between about 1.0 L and about 2.5 L, between about 2.0 L and about 30 L, between about 2.0 L and about 20 L, between about 2.0 L and about 10 L, between about 2.0 L and about 5.0 L, between about 5.0 L and about 30 L, between about 5.0 L and about 20 L, between about 5.0 L and about 10 L, between about 10 L and about 30 L, or between about 10 L and about 20 L). The fourth culture medium can have a volume of, e.g., between about 0.10 L to about 20 L (e.g., between about 0.10 L and about 20 L, between about 0.10 L and about 15 L, between about 0.10 L and about 10 L, between about 0.10 L and about 5.0 L, between about 0.20 L and about 20 L, between about 0.20 L and about 15 L, between about 0.20 L and about 10 L, between about 0.20 L and about 5.0 L, between about 0.50 L and about 20 L, between about 0.50 L and about 15 L, between about 0.50 L and about 10 L, between about 0.50 L and about 5.0 L, between about 1.0 L and about 20 L, between about 1.0 L and about 15 L, between about 1.0 L and about 10 L, between about 1.0 L and about 5.0 L, between about 1.5 L and about 20 L, between about 1.5 L and about 15 L, between about 1.5 L and about 10 L, between about 1.5 L and about 5.0 L, between about 2.0 L and about 25 L, between about 2.0 L and about 20 L, between about 2.0 L and about 15 L, between about 2.0 L and about 10 L, between about 2.0 L and about 5.0 L, between about 5.0 L and about 20 L, between about 5.0 L and about 15 L, between about 5.0 L and about 10 L, between about 10 L and about 20 L, or between about 10 L and about 15 L).

As can be appreciated in the art, the vessel that contains the third cell culture can be any apparatus used in the art for the purpose of culturing mammalian cells (e.g., a flask (e.g., a spin flask), a rolling tube, or a bioreactor). The vessel can include an internal means for agitation (e.g., an impeller) or the vessel can be agitated externally (e.g., through the use of a rotating and/or tilting platform). The vessel can be made of stainless steel or plastic (e.g., a plastic sterile bag). In some embodiments, the vessel can be a disposable single-use bioreactor (e.g., any of the disposable single-use bioreactors described herein). The interior surface of a perfusion bioreactor may have at least one coating (e.g., at least one coating of gelatin, collagen, poly-L-ornithine, polystyrene, and laminin), and as is known in the art, one or more ports for the sparging of $O_2$, $CO_2$, and $N_2$ into the fourth culture medium. The vessel can be equipped with one or more sensor probe(s). When the vessel is composed of a non-rigid plastic material (e.g., a plastic sterile bag), the vessel can be surrounded and supported by an exterior structure.

Each of the disposing steps described herein can be performed using a sterile pipette (e.g., sterile pipetting in a tissue culture hood).

Batch Culturing of the First Cell Culture

After the provision of the first cell culture in step (a), seed train processes described herein include a step of (b) batch culturing the first cell culture to a cell density range of between about $1.0\times10^6$ cells/mL and about $20.0\times10^6$ cells/mL (e.g., between about $1.0\times10^6$ cells/mL and about $17.5\times10^6$ cells/mL, between about $1.0\times10^6$ cells/mL and about $15.0\times10^6$ cells/mL, between about $1.0\times10^6$ cells/mL and about $12.5\times10^6$ cells/mL, between about $1.0\times10^6$ cells/mL and about $10.0\times10^6$ cells/mL, between about $1.0\times10^6$ cells/mL and about $7.5\times10^6$ cells/mL, between about $1.0\times10^6$ cells/mL and about $5.0\times10^6$ cells/mL, between about $1.0\times10^6$ cells/mL and about $2.5\times10^6$ cells/mL, between about $2.0\times10^6$ cells/mL and about $20.0\times10^6$ cells/mL, between about $2.0\times10^6$ cells/mL and about $17.5\times10^6$ cells/mL, between about $2.0\times10^6$ cells/mL and about $15.0\times10^6$ cells/mL, between about $2.0\times10^6$ cells/mL and about $12.5\times10^6$ cells/mL, between about $2.0\times10^6$ cells/mL and about $10.0\times10^6$ cells/mL, between about $2.0\times10^6$ cells/mL and about $7.5\times10^6$ cells/mL, between about $2.0\times10^6$ cells/mL and about $5.0\times10^6$ cells/mL, between about $5.0\times10^6$ cells/mL and about $20.0\times10^6$ cells/mL, between about $5.0\times10^6$ cells/mL and about $17.5\times10^6$ cells/mL, between about $5.0\times10^6$ cells/mL and about $15.0\times10^6$ cells/mL, between about $5.0\times10^6$ cells/mL and about $12.5\times10^6$ cells/mL, between about $5.0\times10^6$ cells/mL and about $10.0\times10^6$ cells/mL, between about $5.0\times10^6$ cells/mL and about $7.5\times10^6$ cells/mL, between about $7.5\times10^6$ cells/mL and about $20.0\times10^6$ cells/mL, between about $7.5\times10^6$ cells/mL and about $17.5\times10^6$ cells/mL, between about $7.5\times10^6$ cells/mL and about $15.0\times10^6$ cells/mL, between about $7.5\times10^6$ cells/mL and about $12.5\times10^6$ cells/mL, between about $7.5\times10^6$ cells/mL and about $10.0\times10^6$ cells/mL, $10.0\times10^6$ cells/mL and about $20.0\times10^6$ cells/mL, between about $10.0\times10^6$ cells/mL and about $17.5\times10^6$ cells/mL, between about $10.0\times10^6$ cells/mL and about $15.0\times10^6$ cells/mL, between about $10.0\times10^6$ cells/mL and about $12.5\times10^6$ cells/mL, between about $12.5\times10^6$ cells/mL and about $20.0\times10^6$ cells/mL, between about $12.5\times10^6$ cells/mL and about $17.5\times10^6$ cells/mL, or between about $12.5\times10^6$ cells/mL and about $15.0\times10^6$ cells/mL). A variety of different methods for determining cell density are known in the art (e.g., use of a light microscope and a hemocytometer or use of an automated cell counter, such as, e.g., Countess® automated cell counter (Life Technologies), Cellometer® (Nexcelom Bioscience), Luna™ automated cell counter (Logos Biosystems), or Vi-Cell® Cell Viability Analyzer).

The batch culturing of the first cell culture does not include the addition of a substantial or significant amount of a liquid culture medium to the first cell culture and does not include the removal of a substantial or significant amount of the first cell culture medium during culturing. The batch culturing can be performed using any of the exemplary temperatures and/or $CO_2$ gas exposures described herein. The batch culturing can be performed using any of the $O_2$ and/or $N_2$ gas exposures known in the art. The batch culturing can also include any of the types of agitation described herein. As one of skill in the art would appreciate, the length of time of batch culturing the first cell culture to achieve the target cell density of between about $1.0\times10^6$ cells/mL to about $20.0\times10^6$ cells/mL (or any of the other cell densities or ranges of cell densities described herein) will depend on the growth rate of the recombinant mammalian cells and the initial cell density of the first cell culture. For example, the first cell culture may be cultured for a period of between about 1 day and about 9 days (e.g., between about 1 day and about 8 days, between about 1 day and about 7 days, between about 1 day and about 6 days, between about 1 day and about 5 days, between about 1 day and about 4 days, between about 1 day and about 3 days, between about 2 days and about 9 days, between about 2 days and about 8 days, between about 2 days and about 7 days, between about 2 days and about 6 days, between about 2 days and about 5 days, between about 2 days and about 4 days, between about 3 days and about 9 days, between about 3 days and about 8 days, between about 3 days and about 7 days, between about 3 days and about 6 days, between about 3 days and about 5 days, between about 4 days and about 9 days, between about 4 days and about 8 days, between about 4 days and about 7 days, between about 4 days and about 6 days, between about 5 days and about 9 days, between about 5 days and about 8 days, between about 5 days and about 7 days, between about 6 days and about 9 days, between about 6 days and about 8 days, or between about 7 days and about 9 days). Other exemplary parameters of batch culturing that can be used in the present methods are described herein.

Providing a Second Cell Culture

The seed train processes described herein further include a step of (c) disposing a volume of the first cell culture of step (b) into a second culture medium included within a perfusion bioreactor to provide a second cell culture with an initial cell density in a range of between about $0.10\times10^6$ cells/mL and about 0.8×10⁶ cells/mL (e.g., any of the initial cell densities or ranges of initial cell densities described for the first cell culture above). As one skilled in the art can appreciate, the appropriate volume of first cell culture to dispose into the second culture medium to arrive at an initial cell density in the range of between about $0.10 \times 10^6$ cells/mL and about $0.80 \times 10^6$ cells/mL for the second cell culture can be determined from the cell density of the first cell culture and the volume of second culture medium. The volume of first cell culture disposed into the second culture medium can be, e.g., between 0.30 L and about 100 L (e.g., between about 0.30 L and about 90 L, between about 0.30 L and about 80 L, between about 0.30 L and about 70 L, between about 0.30 L and about 60 L, between about 0.30 L and about 50 L, between about 0.30 L and about 40 L, between about 0.30 L and about 30 L, between about 0.30 L and about 20 L, between about 0.30 L and about 10 L, between about 1.0 L and about 100 L, between about 1.0 L and about 90 L, between about 1.0 L and about 80 L, between about 1.0 L and about 70 L, between about 1.0 L and about 60 L, between about 1.0 L and about 50 L, between about 1.0 L and about 40 L, between about 1.0 L and about 30 L, between about 1.0 L and about 20 L, between about 1.0 L and about 10 L, between about 2.5 L and about 100 L, between about 2.5 L and about 90 L, between about 2.5 L and about 80 L, between about 2.5 L and about 70 L, between about 2.5 L and about 60 L, between about 2.5 L and about 50 L, between about 2.5 L and about 40 L, between about 2.5 L and about 30 L, between about 2.5 L and about 20 L, between about 2.5 L and about 10 L, between about 5.0 L and about 100 L, between about 5.0 L and about 90 L, between about 5.0 L and about 80 L, between about 5.0 L and about 70 L, between about 5.0 L and about 60 L, between about 5.0 L and about 50 L, between about 5.0 L and about 40 L, between about 5.0 L and about 30 L, between about 5.0 L and about 20 L, between about 5.0 L and about 10 L, between about 15 L and about 100 L, between about 15 L and about 90 L, between about 15 L and about 80 L, between about 15 L and about 70 L, between about 15 L and about 70 L, between about 15 L and about 60 L, between about 15 L and about 50 L, between about 15 L and about 40 L, between about 15 L and about 30 L, between about 15 L and about 20 L, between about 20 L and about 100 L, between about 20 L and about 90 L, between about 20 L and about 80 L, between about 20 L and about 70 L, between about 20 L and about 60 L, between about 20 L and about 50 L, between about 20 L and about 40 L, between about 30 L and about 100 L, between about 30 L and about 90 L, between about 30 L and about 80 L, between about 30 L and about 70 L, between about 30 L and about 60 L, between about 30 L and about 50 L, between about 40 L and about 100 L, between about 40 L and about 90 L, between about 40 L and about 80 L, between about 40 L and about 70 L, between about 40 L and about 60 L, between about 50 L and about 100 L, between about 50 L and about 90 L, between about 50 L and about 80 L, between about 50 L and about 70 L, between about 60 L and about 100 L, between about 60 L and about 90 L, between about 60 L and about 80 L, between about 70 L and about 100 L, between about 70 L and about 90 L, or between about 80 L and about 100 L).

The volume of second cell culture can be, e.g., between 2.0 L and 800 L (e.g., between about 2.0 L and about 750 L, between about 2.0 L and about 700 L, between about 2.0 L and about 650 L, between about 2.0 L and about 600 L, between about 2.0 L and about 550 L, between about 2.0 L and about 550 L, between about 2.0 L and about 500 L, between about 2.0 L and about 450 L, between about 2.0 L and about 400 L, between about 2.0 L and about 350 L, between about 2.0 L and about 300 L, between about 2.0 L and about 250 L, between about 2.0 L and about 200 L, between about 2.0 L and about 150 L, between about 2.0 L and about 100 L, between about 2.0 L and about 50 L, between about 2.0 L and about 25 L, between about 5.0 L and about 800 L, between about 5.0 L and about 750 L, between about 5.0 L and about 700 L, between about 5.0 L and about 650 L, between about 5.0 L and about 600 L, between about 5.0 L and about 550 L, between about 5.0 L and about 500 L, between about 5.0 L and about 450 L, between about 5.0 L and about 400 L, between about 5.0 L and about 350 L, between about 5.0 L and about 300 L, between about 5.0 L and about 250 L, between about 5.0 L and about 200 L, between about 5.0 L and about 150 L, between about 5.0 L and about 100 L, between about 5.0 L and about 50 L, between about 5.0 L and about 25 L, between about 10 L and about 800 L, between about 10 L and about 750 L, between about 10 L and about 700 L, between about 10 L and about 650 L, between about 10 L and about 600 L, between about 10 L and about 550 L, between about 10 L and about 500 L, between about 10 L and about 450 L, between about 10 L and about 400 L, between about 10 L and about 350 L, between about 10 L and about 300 L, between about 10 L and about 300 L, between about 10 L and about 250 L, between about 10 L and about 200 L, between about 10 L and about 150 L, between about 10 L and about 100 L, between about 10 L and about 50 L, between about 10 L and about 25 L, between about 15 L and about 800 L, between about 15 L and about 750 L, between about 15 L and about 700 L, between about 15 L and about 600 L, between about 15 L and about 550 L, between about 15 L and about 500 L, between about 15 L and about 450 L, between about 15 L and about 400 L, between about 15 L and about 350 L, between about 15 L and about 300 L, between about 15 L and about 250 L, between about 15 L and about 200 L, between about 15 L and about 150 L, between about 15 L and about 100 L, between about 15 L and about 50 L, between about 15 L and about 25 L, between about 20 L and about 800 L, between about 20 L and about 750 L, between about 20 L and about 700 L, between about 20 L and about 650 L, between about 20 L and about 600 L, between about 20 L and about 550 L, between about 20 L and about 500 L, between about 20 L and about 450 L, between about 20 L and about 400 L, between about 20 L and about 350 L, between about 20 L and about 300 L, between about 20 L and about 250 L, between about 20 L and about 200 L, between about 20 L and about 150 L, between about 20 L and about 100 L, between about 20 L and about 50 L, between about 25 L and about 800 L, between about 25 L and about 750 L, between about 25 L and about 700 L, between about 25 L and about 650 L, between about 25 L and about 600 L, between about 25 L and about 550 L, between about 25 L and about 500 L, between about 25 L and about 450 L, between about 25 L and about 400 L, between about 25 L and about 350 L, between about 25 L and about 300 L, between about 25 L and about 250 L, between about 25 L and about 200 L, between about 25 L and about 150 L, between about 25 L and about 100 L, between about 25 L and about 50 L, between about 50 L and about 800 L, between about 50 L and about 750 L, between about 50 L and about 700 L, between about 50 L and about 650 L, between about 50 L and about 600 L, between about 50 L and about 550 L, between about 50 L and about 500 L, between about 50 L and about 450 L, between about 50 L and about 400 L, between about 50 L and about 350 L, between about 50 L and about 300 L, between about 50 L and about 250 L, between about 50 L and about 200 L, between about 50 L and about 150 L, between about 50 L and about 100 L, between about 75 L and about 800 L, between about 75 L and about 750 L, between about 75 L and about 700 L, between about 75 L and about 650 L, between about 75 L and about 600 L, between about 75 L and about 550 L, between about 75 L and about 500 L, between about 75 L and about 450 L, between about 75 L and about 400 L, between about 75 L and about 350 L, between about 75 L and about 300 L, between about 75 L and about 250 L, between about 75 L and about 200 L, between about 75 L and about 150 L, between about 75 L and about 100 L, between about 100 L and about 800 L, between about 100 L and about 750 L, between about 100 L and about 700 L, between about 100 L and about 650 L, between about 100 L and about 600 L, between about 100 L and about 550 L, between about 100 L and about 500 L, between about 100 L and about 450 L, between about 100 L and about 400 L, between about 100 L and about 350 L, between about 100 L and about 300 L, between about 100 L and about 250 L, between about 100 L and about 200 L, between about 100 L and about 150 L, between about 150 L and about 800 L, between about 150 L and about 750 L, between about 150 L and about 700 L, between about 150 L and about 650 L, between about 150 L and about 600 L, between about 150 L and about 550 L, between about 150 L and about 500 L, between about 150 L and about 450 L, between about 150 L and about 400 L, between about 150 L and about 350 L, between about 150 L and about 300 L, between about 150 L and about 250 L, between about 150 L and about 200 L, between about 200 L and about 800 L, between about 200 L and about 750 L, between about 200 L and about 700 L, between about 200 L and about 650 L, between about 200 L and about 600 L, between about 200 L and about 550 L, between about 200 L and about 500 L, between about 200 L and about 450 L, between about 200 L and about 400 L, between about 200 L and about 350 L, between about 200 L and about 300 L, between about 200 L and about 250 L, between about 250 L and about 800 L, between about 250 L and about 750 L, between about 250 L and about 700 L, between about 250 L and about 650 L, between about 250 L and about 600 L, between about 250 L and about 550 L, between about 250 L and about 500 L, between about 250 L and about 450 L, between about 250 L and about 400 L, between about 250 L and about 350 L, between about 300 L and about 800 L, between about 300 L and about 750 L, between about 300 L and about 700 L, between about 300 L and about 650 L, between about 300 L and about 600 L, between about 300 L and about 550 L, between about 300 L and about 500 L, between about 300 L and about 450 L, between about 300 L and about 400 L, between about 300 L and about 350 L, between about 350 L and about 800 L, between about 350 L and about 750 L, between about 350 L and about 700 L, between about 350 L and about 650 L, between about 350 L and about 600 L, between about 350 L and about 550 L, between about 350 L and about 500 L, between about 350 L and about 450 L, between about 350 L and about 400 L, between about 400 L and about 800 L, between about 400 L and about 750 L, between about 400 L and about 700 L, between about 400 L and about 650 L, between about 400 L and about 600 L, between about 400 L and about 550 L, between about 400 L and about 500 L, between about 400 L and about 450 L, between about 450 L and about 800 L, between about 450 L and about 750 L, between about 450 L and about 700 L, between about 450 L and about 650 L, between about 450 L and about 600 L, between about 450 L and about 550 L, between about 450 L and about 500 L, between about 500 L and about 800 L, between about 500 L and about 750 L, between about 500 L and about 700 L, between about 500 L and about 650 L, between about 500 L and about 600 L, between about 500 L and about 650 L, between about 550 L and about 800 L, between about 550 L and about 750 L, between about 550 L and about 700 L, between about 550 L and about 650 L, between about 550 L and about 600 L, between about 600 L and about 800 L, between about 600 L and about 750 L, between about 600 L and about 700 L, between about 600 L and about 650 L, between about 650 L and about 800 L, between about 650 L and about 750 L, between about 650 L and about 700 L, between about 700 L and about 800 L, between about 700 L and about 750 L, or between about 750 L and about 800 L).

The perfusion bioreactor can be any of the exemplary perfusion bioreactors described herein or known in the art. For example, a perfusion bioreactor can be made of stainless steel or plastic (e.g., a plastic sterile bag). The interior surface of a perfusion bioreactor may have at least one coating (e.g., at least one coating of gelatin, collagen, poly-L-ornithine, polystyrene, and laminin), and as is known in the art, one or more ports for the sparging of $O_2$, $CO_2$, and $N_2$ into the liquid culture medium, and a stir mechanism for agitating the liquid culture medium. The perfusion bioreactor can also be equipped with a mechanical device that is capable of removing a volume of the second liquid culture medium from the bioreactor and optionally, a filter within the mechanical device that removes the cells from the second liquid culture medium during the process of transfer of the second liquid culture medium out of the bioreactor (e.g., an alternating tangential flow (ATF), a tangential flow filtration (TFF) system, or a filtering system described in U.S. Provisional Patent Application No. 61/878,502). The bioreactor can also be equipped with one or more pumps, and one or more reservoirs to hold the removed second culture medium and the new culture medium to be perfused into the perfusion bioreactor.

The perfusion bioreactor can have an internal volume that is, e.g., between about 5.0 L and about 2,000 (e.g., between about 5.0 L and about 1,900 L, between about 5.0 L and about 1,800 L, between about 5.0 L and about 1,700 L, between about 5.0 L and about 1,600 L, between about 5.0 L and about 1,500 L, between about 5.0 L and about 1,400 L, between about 5.0 L and about 1,300 L, between about 5.0 L and about 1,200 L, between about 5.0 L and about 1,100 L, between about 5.0 L and about 1,000 L, between about 5.0 L and about 900 L, between about 5.0 L and about 800 L, between about 5.0 L and about 700 L, between about 5.0 L and about 600 L, between about 5.0 L and about 500 L, between about 5.0 L and about 400 L, between about 5.0 L and about 300 L, between about 5.0 L and about 200 L, between about 5.0 L and about 100 L, between about 5.0 L and about 50 L, between about 100 L and about 2,000 L, between about 100 L and about 1,900 L, between about 100 L and about 1,800 L, between about 100 L and about 1,700 L, between about 100 L and about 1,600 L, between about 100 L and about 1,500 L, between about 100 L and about 1,400 L, between about 100 L and about 1,300 L, between about 100 L and about 1,200 L, between about 100 L and about 1,100 L, between about 100 L and about 1,000 L, between about 100 L and about 900 L, between about 100 L and about 800 L, between about 100 L and about 700 L, between about 100 L and about 600 L, between about 100

L and about 500 L, between about 100 L and about 400 L, between about 100 L and about 300 L, between about 100 L and about 200 L, between about 150 L and about 2,000 L, between about 150 L and about 1,900 L, between about 150 L and about 1,800 L, between about 150 L and about 1,700 L, between about 150 L and about 1,600 L, between about 150 L and about 1,500 L, between about 150 L and about 1,400 L, between about 150 L and about 1,300 L, between about 150 L and about 1,300 L, between about 150 L and about 1,200 L, between about 150 L and about 1,100 L, between about 150 L and about 1,000 L, between about 150 L and about 900 L, between about 150 L and about 800 L, between about 150 L and about 700 L, between about 150 L and about 600 L, between about 150 L and about 500 L, between about 150 L and about 400 L, between about 150 L and about 300 L, between about 150 L and about 200 L, between about 200 L and about 2,000 L, between about 200 L and about 1,900 L, between about 200 L and about 1,800 L, between about 200 L and about 1,700 L, between about 200 L and about 1,600 L, between about 200 L and about 1,500 L, between about 200 L and about 1,400 L, between about 200 L and about 1,300 L, between about 200 L and about 1,200 L, between about 200 L and about 1,100 L, between about 200 L and about 1,000 L, between about 200 L and about 900 L, between about 200 L and about 800 L, between about 200 L and about 700 L, between about 200 L and about 600 L, between about 200 L and about 500 L, between about 200 L and about 400 L, between about 200 L and about 300 L, between about 300 L and about 2,000 L, between about 300 L and about 1,900 L, between about 300 L and about 1,800 L, between about 300 L and about 1,700 L, between about 300 L and about 1,600 L, between about 300 L and about 1,500 L, between about 300 L and about 1,400 L, between about 300 L and about 1,300 L, between about 300 L and about 1,200 L, between about 300 L and about 1,100 L, between about 300 L and about 1,000 L, between about 300 L and about 900 L, between about 300 L and about 800 L, between about 300 L and about 700 L, between about 300 L and about 600 L, between about 300 L and about 500 L, between about 300 L and about 400 L, between about 400 L and about 2,000 L, between about 400 L and about 1,900 L, between about 400 L and about 1,800 L, between about 400 L and about 1,700 L, between about 400 L and about 1,600 L, between about 400 L and about 1,500 L, between about 400 L and about 1,400 L, between about 400 L and about 1,300 L, between about 400 L and about 1,200 L, between about 400 L and about 1,100 L, between about 400 L and about 1,000 L, between about 400 L and about 900 L, between about 400 L and about 800 L, between about 400 L and about 700 L, between about 400 L and about 600 L, between about 400 L and about 500 L, between about 500 L and about 2,000 L, between about 500 L and about 1,900 L, between about 500 L and about 1,800 L, between about 500 L and about 1,700 L, between about 500 L and about 1,600 L, between about 500 L and about 1,500 L, between about 500 L and about 1,400 L, between about 500 L and about 1,300 L, between about 500 L and about 1,200 L, between about 500 L and about 1,100 L, between about 500 L and about 1,000 L, between about 500 L and about 900 L, between about 500 L and about 800 L, between about 500 L and about 700 L, between about 500 L and about 600 L, between about 600 L and about 2,000 L, between about 600 L and about 1,900 L, between about 600 L and about 1,800 L, between about 600 L and about 1,700 L, between about 600 L and about 1,600 L, between about 600 L and about 1,500 L, between about 600 L and about 1,400 L, between about 600 L and about 1,300 L, between about 600 L and about 1,200 L, between about 600 L and about 1,100 L, between about 600 L and about 1,000 L, between about 600 L and about 900 L, between about 600 L and about 800 L, between about 600 L and about 700 L, between about 700 L and about 2,000 L, between about 700 L and about 1,900 L, between 700 L and about 1,800 L, between about 700 L and about 1,700 L, between about 700 L and about 1,600 L, between about 700 L and about 1,500 L, between about 700 L and about 1,400 L, between about 700 L and about 1,300 L, between about 700 L and about 1,200 L, between about 700 L and about 1,100 L, between about 700 L and about 1,000 L, between about 700 L and about 900 L, between about 700 L and about 800 L, between 800 L and about 2,000 L, between about 800 L and about 1,900 L, between about 800 L and about 1,800 L, between about 800 L and about 1,700 L, between about 800 L and about 1,600 L, between about 800 L and about 1,500 L, between about 800 L and about 1,400 L, between about 800 L and about 1,300 L, between about 800 L and about 1,200 L, between about 800 L and about 1,100 L, between about 800 L and about 1,000 L, between about 800 L and about 900 L, between about 1,000 L to about 2,000 L, between about 1,000 L to about 1,750 L, between about 1,000 L to about 1,500 L, between about 1,000 L to about 1,250 L, between about 1,250 L to about 2,000 L, between about 1,250 L to about 1,750 L, between about 1,250 L to about 1,500 L, between about 1,500 L to about 2,000 L, between about 1,500 L to about 1,750 L, or between about 1,750 L to about 2,000 L).

Perfusion Culturing of the Second Cell Culture

The seed train processes described herein further include a step of (d) perfusion culturing the second cell culture to a cell density of between about $5.0\times10^6$ cells/mL and about $140\times10^6$ cells/mL (e.g., between about $5.0\times10^6$ cells/mL and about $130\times10^6$ cells/mL, between about $5.0\times10^6$ cells/mL and about $120\times10^6$ cells/mL, between about $5.0\times10^6$ cells/mL and about $110\times10^6$ cells/mL, between about $5.0\times10^6$ cells/mL and about $100\times10^6$ cells/mL, between about $5.0\times10^6$ cells/mL and about $90\times10^6$ cells/mL, between about $5.0\times10^6$ cells/mL and about $80\times10^6$ cells/mL, between about $5.0\times10^6$ cells/mL and about $70\times10^6$ cells/mL, between about $5.0\times10^6$ cells/mL and about $60\times10^6$ cells/mL, between about $5.0\times10^6$ cells/mL and about $50\times10^6$ cells/mL, between about $5.0\times10^6$ cells/mL and about $40\times10^6$ cells/mL, between about $5.0\times10^6$ cells/mL and about $30\times10^6$ cells/mL, between about $5.0\times10^6$ cells/mL and about $20\times10^6$ cells/mL, between about $5.0\times10^6$ cells/mL and about $10\times10^6$ cells/mL, between about $10\times10^6$ cells/mL and about $140\times10^6$ cells/mL, between about $10\times10^6$ cells/mL and about $130\times10^6$ cells/mL, between about $10\times10^6$ cells/mL and about $120\times10^6$ cells/mL, between about $10\times10^6$ cells/mL and about $110\times10^6$ cells/mL, between about $10\times10^6$ cells/mL and about $100\times10^6$ cells/mL, between about $10\times10^6$ cells/mL and about $90\times10^6$ cells/mL, between about $10\times10^6$ cells/mL and about $80\times10^6$ cells/mL, between about $10\times10^6$ and about $70\times10^6$ cells/mL, between about $10\times10^6$ cells/mL and about $60\times10^6$ cells/mL, between about $10\times10^6$ cells/mL and about $50\times10^6$ cells/mL, between about $10\times10^6$ cells/mL and about $40\times10^6$ cells/mL, between about $10\times10^6$ cells/mL and about $30\times10^6$ cells/mL, between about $10\times10^6$ cells/mL and about $20\times10^6$ cells/mL, between about $15\times10^6$ cells/mL and about $140\times10^6$ cells/mL, between about $15\times10^6$ cells/mL and about $130\times10^6$ cells/mL, between about $15\times10^6$ cells/mL and about $120\times10^6$ cells/mL, between about $15\times10^6$ cells/mL and about $110\times10^6$ cells/mL, between about $15\times10^6$ cells/mL and about $100\times10^6$ cells/mL, between about $15\times10^6$ cells/mL and about $90\times10^6$ cells/mL, between about $15\times10^6$ cells/mL and about 80×10$^6$ cells/mL, between about 15×10$^6$ cells/mL and about 70×10$^6$ cells/mL, between about 15×10$^6$ cells/mL and about 60×10$^6$ cells/mL, between about 15×10$^6$ cells/mL and about 50×10$^6$ cells/mL, between about 15×10$^6$ cells/mL and about 40×10$^6$ cells/mL, between about 15×10$^6$ cells/mL and about 30×10$^6$ cells/mL, between about 15×10$^6$ cells/mL and about 20×10$^6$ cells/mL, between about 20×10$^6$ cells/mL and about 140×10$^6$ cells/mL, between about 20×10$^6$ cells/mL and about 130×10$^6$ cells/mL, between about 20×10$^6$ cells/mL and about 120×10$^6$ cells/mL, between about 20×10$^6$ cells/mL and about 110×10$^6$ cells/mL, between about 20×10$^6$ cells/mL and about 100×10$^6$ cells/mL, between about 20×10$^6$ cells/mL and about 90×10$^6$ cells/mL, between about 20×10$^6$ cells/mL and about 80×10$^6$ cells/mL, between about 20×10$^6$ cells/mL and about 70×10$^6$ cells/mL, between about 20×10$^6$ cells/mL and about 60×10$^6$ cells/mL, between about 20×10$^6$ cells/mL and about 50×10$^6$ cells/mL, between about 20×10$^6$ cells/mL and about 40×10$^6$ cells/mL, between about 20×10$^6$ cells/mL and about 30×10$^6$ cells/mL, between about 25×10$^6$ cells/mL and about 140×10$^6$ cells/mL, between about 25×10$^6$ cells/mL and about 130×10$^6$ cells/mL, between about 25×10$^6$ cells/mL and about 120×10$^6$ cells/mL, between about 25×10$^6$ cells/mL and about 110×10$^6$ cells/mL, between about 25×10$^6$ cells/mL and about 100×10$^6$ cells/mL, between about 25×10$^6$ cells/mL and about 90×10$^6$ cells/mL, between about 25×10$^6$ cells/mL and about 80×10$^6$ cells/mL, between about 25×10$^6$ cells/mL and about 70×10$^6$ cells/mL, between about 25×10$^6$ cells/mL and about 60×10$^6$ cells/mL, between about 25×10$^6$ cells/mL and about 50×10$^6$ cells/mL, between about 25×10$^6$ cells/mL and about 40×10$^6$ cells/mL, between about 25×10$^6$ cells/mL and about 30×10$^6$ cells/mL, between about 30×10$^6$ cells/mL and about 140×10$^6$ cells/mL, between about 30×10$^6$ cells/mL and about 130×10$^6$ cells/mL, between about 30×10$^6$ cells/mL and about 120×10$^6$ cells/mL, between about 30×10$^6$ cells/mL and about 110×10$^6$ cells/mL, between about 30×10$^6$ cells/mL and about 100×10$^6$ cells/mL, between about 30×10$^6$ cells/mL and about 90×10$^6$ cells/mL, between about 30×10$^6$ cells/mL and about 80×10$^6$ cells/mL, between about 30×10$^6$ cells/mL and about 70×10$^6$ cells/mL, between about 30×10$^6$ cells/mL and about 60×10$^6$ cells/mL, between about 30×10$^6$ cells/mL and about 50×10$^6$ cells/mL, between about 30×10$^6$ cells/mL and about 40×10$^6$ cells/mL, between about 40×10$^6$ cells/mL and about 140×10$^6$ cells/mL, between about 40×10$^6$ cells/mL and about 130×10$^6$ cells/mL, between about 40×10$^6$ cells/mL and about 120×10$^6$ cells/mL, between about 40×10$^6$ cells/mL and about 110×10$^6$ cells/mL, between about 40×10$^6$ cells/mL and about 100×10$^6$ cells/mL, between about 40×10$^6$ cells/mL and about 90×10$^6$ cells/mL, between about 40×10$^6$ cells/mL to about 80×10$^6$ cells/mL, between about 40×10$^6$ cells/mL and about 70×10$^6$ cells/mL, between about 40×10$^6$ cells/mL and about 60×10$^6$ cells/mL, between about 40×10$^6$ cells/mL and about 50×10$^6$ cells/mL, between about 50×10$^6$ cells/mL and about 140×10$^6$ cells/mL, between about 50×10$^6$ cells/mL and about 130×10$^6$ cells/mL, between about 50×10$^6$ cells/mL and about 120×10$^6$ cells/mL, between about 50×10$^6$ cells/mL and about 110×10$^6$ cells/mL, between about 50×10$^6$ cells/mL and about 100×10$^6$ cells/mL, between about 50×10$^6$ cells/mL and about 90×10$^6$ cells/mL, between about 50×10$^6$ cells/mL and about 80×10$^6$ cells/mL, between about 50×10$^6$ cells/mL and about 70×10$^6$ cells/mL, between about 50×10$^6$ cells/mL and about 60×10$^6$ cells/mL, between about 60×10$^6$ cells/mL and about 140×10$^6$ cells/mL, between about 60×10$^6$ cells/mL and about 130×10$^6$ cells/mL, between about 60×10$^6$ cells/mL and about 120×10$^6$ cells/mL, between about 60×10$^6$ cells/mL and about 110×10$^6$ cells/mL, between about 60×10$^6$ cells/mL and about 100×10$^6$ cells/mL, between about 60×10$^6$ cells/mL and about 90×10$^6$ cells/mL, between about 60×10$^6$ cells/mL and about 80×10$^6$ cells/mL, between about 60×10$^6$ cells/mL and about 70×10$^6$ cells/mL, between about 70×10$^6$ cells/mL and about 140×10$^6$ cells/mL, between about 70×10$^6$ cells/mL and about 130×10$^6$ cells/mL, between about 70×10$^6$ cells/mL and about 120×10$^6$ cells/mL, between about 70×10$^6$ cells/mL and about 110×10$^6$ cells/mL, between about 70×10$^6$ cells/mL and about 100×10$^6$ cells/mL, between about 70×10$^6$ cells/mL and about 90×10$^6$ cells/mL, between about 70×10$^6$ cells/mL and about 80×10$^6$ cells/mL, between about 80×10$^6$ cells/mL and about 140×10$^6$ cells/mL, between about 80×10$^6$ cells/mL and about 130×10$^6$ cells/mL, between about 80×10$^6$ cells/mL and about 120×10$^6$ cells/mL, between about 80×10$^6$ cells/mL and about 110×10$^6$ cells/mL, between about 80×10$^6$ cells/mL and about 100×10$^6$ cells/mL, between about 80×10$^6$ cells/mL and about 90×10$^6$ cells/mL, between about 90×10$^6$ cells/mL and about 140×10$^6$ cells/mL, between about 90×10$^6$ cells/mL and about 130×10$^6$ cells/mL, between about 90×10$^6$ cells/mL and about 120×10$^6$ cells/mL, between about 90×10$^6$ cells/mL and about 110×10$^6$ cells/mL, between about 90×10$^6$ cells/mL and about 100×10$^6$ cells/mL, between about 100×10$^6$ cells/mL and about 140×10$^6$ cells/mL, between about 100×10$^6$ cells/mL and about 130×10$^6$ cells/mL, between about 100×10$^6$ cells/mL and about 120×10$^6$ cells/mL, between about 100×10$^6$ cells/mL and about 110×10$^6$ cells/mL, between about 110×10$^6$ cells/mL and about 140×10$^6$ cells/mL, between about 110×10$^6$ cells/mL and about 140×10$^6$ cells/mL, between about 110×10$^6$ cells/mL and about 130×10$^6$ cells/mL, between about 110×10$^6$ cells/mL and about 120×10$^6$ cells/mL, between about 120×10$^6$ cells/mL and about 140×10$^6$ cells/mL, between about 120×10$^6$ cells/mL and about 130×10$^6$ cells/mL, or between about 130×10$^6$ cells/mL and about 140×10$^6$ cells/mL).

Perfusion culturing is well-known in the art and in this step includes removing (e.g., continuously or periodically removing) from a perfusion bioreactor a volume of the liquid culture medium (e.g., a volume of the second liquid culture medium in the perfusion bioreactor that is substantially free of cells), and adding to the perfusion bioreactor at about the same time or substantially the same time a volume of replacement culture medium. Removal and adding can be performed simultaneously or sequentially, or a combination of the two. Further, removal and adding can be performed continuously (e.g., at a rate that removes and replaces a volume of between 0.1% to 800% (e.g., between 1% and 700%, between 1% and 600%, between 1% and 500%, between 1% and 400%, between 1% and 350%, between 1% and 300%, between 1% and 250%, between 1% and 100%, between 100% and 200%, between 5% and 150%, between 10% and 50%, between 15% and 40%, between 8% and 80%, and between 4% and 30%) of the volume of the perfusion bioreactor or the initial volume of the liquid culture medium at the start of the culturing (e.g., the volume of the second liquid culture medium volume) over any given time period (e.g., over a 24-hour period, over an incremental time period of about 1 hour to about 24 hours, or over an incremental time period of greater than 24 hours)) or periodically (e.g., once every third day, once every other day, once a day, twice a day, three times a day, four times a day, or five times a day), or any combination thereof. Where performed periodically, the volume that is removed or replaced (e.g., within about a 24-hour period, within an incremental time period of about 1 hour to about 24 hours, or within an incremental time period of greater than 24 hours) can be, e.g., between 0.1% to 800% (e.g., between 1% and 700%, between 1% and 600%, between 1% and 500%, between 1% and 400%, between 1% and 300%, between 1% and 200%, between 1% and 100%, between 100% and 200%, between 5% and 150%, between 10% and 50%, between 15% and 40%, between 8% and 80%, and between 4% and 30%) of the volume of the perfusion bioreactor or the volume of culture medium in the bioreactor at the start of the culturing (e.g., the second liquid culture medium volume). The volume of the liquid culture medium removed and the volume of the replacement liquid culture medium (e.g., fresh liquid culture medium) added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the volume of the liquid culture medium is removed (volume/unit of time) and the rate at which the volume of the replacement liquid culture medium (e.g., fresh second liquid culture medium) is added (volume/unit of time) can be varied. The rate at which the volume of the liquid culture medium is removed (volume/unit of time) and the rate at which the volume of the replacement liquid culture medium (e.g., fresh liquid culture medium) is added (volume/unit of time) can be about the same or can be different.

Alternatively, the volume removed and added can change (e.g., gradually increase) over each 24-hour period (or alternatively, an incremental time period of between 1 hour and about 24 hours or an incremental time period of greater than 24 hours) during the culturing period. For example, the volume of the liquid culture medium removed and the volume of the replacement liquid culture medium added (e.g., fresh liquid culture medium added) within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the bioreactor volume or the volume of liquid culture medium present at the start of culturing (e.g., the second culture medium volume) to about 25% to about 300% of the bioreactor volume or the volume of liquid culture medium present at the start of culturing (e.g., the second liquid culture medium volume).

Skilled practitioners will appreciate that the liquid culture medium removed and the replacement liquid culture medium added (e.g., fresh liquid culture medium added) can be the same type of media (e.g., serum-free or serum-free, protein-free chemically-defined medium). In other instances, the liquid culture medium removed and the replacement liquid culture medium added (e.g., fresh liquid culture medium added) can be different.

The volume of the liquid culture medium can be removed, e.g., using a mechanical system and/or by seeping or gravity flow of the volume through a sterile membrane with a molecular weight cut-off that excludes mammalian cells present in the volume.

The volume of the replacement liquid culture medium (e.g., fresh second liquid culture medium) can be added to the bioreactor in an automated fashion, e.g., by perfusion pump. In some instances, removing the volume of the liquid culture medium (e.g., a volume of the second liquid culture medium that is substantially free of mammalian cells) and adding the volume of replacement liquid culture medium (e.g., fresh liquid culture medium) does not occur within at least 1 hour (e.g., within 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours) of the seeding of the perfusion bioreactor with a mammalian cell.

As one of skill in the art would appreciate, the length of time of perfusion culturing the second cell culture to achieve the target cell density of between about $5\times10^6$ cells/mL to about $140\times10^6$ cells/mL (or any of the other cell densities or ranges of cell densities described herein) will depend on the growth rate of the recombinant mammalian cells and the initial cell density of the second cell culture. For example, the second culture may be perfusion cultured for a period of between about 1 day and about 9 days (e.g., any of the exemplary ranges of time periods listed for batch culturing above). Other exemplary parameters of perfusion culturing that can be used in the present methods are described herein.

Providing a Production Cell Culture

The seed train processes described herein further include a step of (e) disposing a volume of the second cell culture of step (d) into a third culture medium included within a production bioreactor to provide a production cell culture with an initial cell density in a range of about $0.25\times10^6$ cells/mL to about $10\times10^6$ cells/mL (e.g., between about $0.25\times10^6$ cells/mL and about $9.0\times10^6$ cells/mL, $0.25\times10^6$ cells/mL and about $8.0\times10^6$ cells/mL, between about $0.25\times10^6$ cells/mL and about $7.0\times10^6$ cells/mL, between about $0.25\times10^6$ cells/mL and about $6.0\times10^6$ cells/mL, between about $0.25\times10^6$ cells/mL and about $5.0\times10^6$ cells/mL, between about $0.25\times10^6$ cells/mL and about $4.0\times10^6$ cells/mL, between about $0.25\times10^6$ cells/mL and about $3.0\times10^6$ cells/mL, between about $0.25\times10^6$ cells/mL and about $2.0\times10^6$ cells/mL, between about $0.25\times10^6$ cells/mL and about $1.0\times10^6$ cells/mL, between about $0.25\times10^6$ cells/mL and about $0.75\times10^6$ cells/mL, between about $0.50\times10^6$ cells/mL and about $10\times10^6$ cells/mL, between about $0.50\times10^6$ cells/mL and about $9.0\times10^6$ cells/mL, $0.50\times10^6$ cells/mL and about $8.0\times10^6$ cells/mL, between about $0.50\times10^6$ cells/mL and about $7.0\times10^6$ cells/mL, between about $0.50\times10^6$ cells/mL and about $6.0\times10^6$ cells/mL, between about $0.50\times10^6$ cells/mL and about $5.0\times10^6$ cells/mL, between about $0.50\times10^6$ cells/mL and about $4.0\times10^6$ cells/mL, between about $0.50\times10^6$ cells/mL and about $3.0\times10^6$ cells/mL, between about $0.50\times10^6$ cells/mL and about $2.0\times10^6$ cells/mL, between about $0.50\times10^6$ cells/mL and about $1.0\times10^6$ cells/mL, between about $0.75\times10^6$ cells/mL and about $10\times10^6$ cells/mL, between about $0.75\times10^6$ cells/mL and about $9.0\times10^6$ cells/mL, between about $0.75\times10^6$ cells/mL and about $8.0\times10^6$ cells/mL, between about $0.75\times10^6$ cells/mL and about $7.0\times10^6$ cells/mL, between about $0.75\times10^6$ cells/mL and about $6.0\times10^6$ cells/mL, between about $0.75\times10^6$ cells/mL and about $5.0\times10^6$ cells/mL, between about $0.75\times10^6$ cells/mL and about $4.0\times10^6$ cells/mL, between about $0.75\times10^6$ cells/mL and about $3.0\times10^6$ cells/mL, between about $0.75\times10^6$ cells/mL and about $2.0\times10^6$ cells/mL, between about $0.75\times10^6$ cells/mL and about $1.0\times10^6$ cells/mL, between about $1.0\times10^6$ cells/mL and about $10\times10^6$ cells/mL, between about $1.0\times10^6$ cells/mL and about $9.0\times10^6$ cells/mL, between about $1.0\times10^6$ cells/mL and about $8.0\times10^6$ cells/mL, between about $1.0\times10^6$ cells/mL and about $7.0\times10^6$ cells/mL, between about $1.0\times10^6$ cells/mL and about $6.0\times10^6$ cells/mL, between about $1.0\times10^6$ cells/mL and about $5.0\times10^6$ cells/mL, between about $1.0\times10^6$ cells/mL and about $4.0\times10^6$ cells/mL, between about $1.0\times10^6$ cells/ mL and about $3.0 \times 10^6$ cells/mL, between about $1.0 \times 10^6$ cells/mL and about $2.0 \times 10^6$ cells/mL, between about $2.0 \times 10^6$ cells/mL and about $10 \times 10^6$ cells/mL, between about $2.0 \times 10^6$ cells/mL and about $9.0 \times 10^6$ cells/mL, between about $2.0 \times 10^6$ cells/mL and about $8.0 \times 10^6$ cells/mL, between about $2.0 \times 10^6$ cells/mL and about $7.0 \times 10^6$ cells/mL, between about $2.0 \times 10^6$ cells/mL and about $6.0 \times 10^6$ cells/mL, between about $2.0 \times 10^6$ cells/mL and about $5.0 \times 10^6$ cells/mL, between about $2.0 \times 10^6$ cells/mL and about $4.0 \times 10^6$ cells/mL, between about $2.0 \times 10^6$ cells/mL to about $3.0 \times 10^6$ cells/mL, between about $2.5 \times 10^6$ cells/mL and about $10 \times 10^6$ cells/mL, between about $2.5 \times 10^6$ cells/mL and about $9.0 \times 10^6$ cells/mL, between about $2.5 \times 10^6$ cells/mL and about $8.0 \times 10^6$ cells/mL, between about $2.5 \times 10^6$ cells/mL and about $7.0 \times 10^6$ cells/mL, between about $2.5 \times 10^6$ cells/mL and about $6.0 \times 10^6$ cells/mL, between about $2.5 \times 10^6$ cells/mL and about $5.0 \times 10^6$ cells/mL, between about $2.5 \times 10^6$ cells/mL and about $4.0 \times 10^6$ cells/mL, between about $2.5 \times 10^6$ cells/mL and about $3.0 \times 10^6$ cells/mL, between about $3.0 \times 10^6$ cells/mL and about $10 \times 10^6$ cells/mL, between about $3.0 \times 10^6$ cells/mL and about $9.0 \times 10^6$ cells/mL, between about $3.0 \times 10^6$ cells/mL and about $8.0 \times 10^6$ cells/mL, between about $3.0 \times 10^6$ cells/mL and about $7.0 \times 10^6$ cells/mL, between about $3.0 \times 10^6$ cells/mL and about $6.0 \times 10^6$ cells/mL, between about $3.0 \times 10^6$ cells/mL and about $5.0 \times 10^6$ cells/mL, between about $3.0 \times 10^6$ cells/mL and about $4.0 \times 10^6$ cells/mL, between about $4.0 \times 10^6$ cells/mL and about $10 \times 10^6$ cells/mL, between about $4.0 \times 10^6$ cells/mL and about $9.0 \times 10^6$ cells/mL, between about $4.0 \times 10^6$ cells/mL and about $8.0 \times 10^6$ cells/mL, between about $4.0 \times 10^6$ cells/mL and about $7.0 \times 10^6$ cells/mL, between about $4.0 \times 10^6$ cells/mL and about $6.0 \times 10^6$ cells/mL, between about $4.0 \times 10^6$ cells/mL and about $5.0 \times 10^6$ cells/mL, between about $5.0 \times 10^6$ cells/mL and about $10 \times 10^6$ cells/mL, between about $5.0 \times 10^6$ cells/mL and about $9.0 \times 10^6$ cells/mL, between about $5.0 \times 10^6$ cells/mL and about $8.0 \times 10^6$ cells/mL, between about $5.0 \times 10^6$ cells/mL and about $7.0 \times 10^6$ cells/mL, between about $5.0 \times 10^6$ cells/mL and about $6.0 \times 10^6$ cells/mL, between about $6.0 \times 10^6$ cells/mL and about $10 \times 10^6$ cells/mL, between about $6.0 \times 10^6$ cells/mL and about $9.0 \times 10^6$ cells/mL, between about $6.0 \times 10^6$ cells/mL and about $8.0 \times 10^6$ cells/mL, between about $6.0 \times 10^6$ cells/mL and about $7.0 \times 10^6$ cells/mL, between about $7.0 \times 10^6$ cells/mL and about $10 \times 10^6$ cells/mL, between about $7.0 \times 10^6$ cells/mL and about $9.0 \times 10^6$ cells/mL, between about $7.0 \times 10^6$ cells/mL and about $8.0 \times 10^6$ cells/mL, between about $8.0 \times 10^6$ cells/mL and about $10 \times 10^6$ cells/mL, between about $8.0 \times 10^6$ cells/mL and about $9.0 \times 10^6$ cells/mL, or between about $9.0 \times 10^6$ cells/mL and about $10 \times 10^6$ cells/mL). In some embodiments, the initial cell density of the production cell culture is at least about 8% (e.g., at least about 10%, at least about 12%, at least about 14%, at least about 16%, at least about 18%, at least about 20%, at least about 22%, at least about 24%, at least about 26%, at least about 28%, at least about 30%, at least about 32%, at least about 34%, at least about 36%, at least about 38%, at least about 40%, or at least about 50%) of the steady state production cell density. For example, the initial cell density of the production cell culture can be between about 4.0% and about 30% (e.g., between about 4.0% and about 28%, between about 4.0% and about 26%, between about 4.0% and about 24%, between about 4.0% and about 22%, between about 4.0% and about 20%, between about 4.0% and about 18%, between about 4.0% and about 16%, between about 4.0% and about 14%, between about 4.0% and about 12%, between about 4.0% and about 10%, between about 4.0% and about 8.0%, between about 4.0% and about 6.0%, between about 5.0% and about 30%, between about 5.0% and about 28%, between about 5.0% and about 26%, between about 5.0% and about 24%, between about 5.0% and about 22%, between about 5.0% and about 20%, between about 5.0% and about 18%, between about 5.0% and about 16%, between about 5.0% and about 14%, between about 5.0% and about 12%, between about 5.0% and about 10%, between about 5.0% and about 8.0%, between about 10% and about 30%, between about 10% and about 28%, between about 10% and about 26%, between about 10% and about 24%, between about 10% and about 22%, between about 10% and about 20%, between about 10% and about 18%, between about 10% and about 16%, between about 10% and about 14%, between about 10% and about 12%, between about 15% and about 30%, between about 15% and about 28%, between about 15% and about 26%, between about 15% and about 24%, between about 15% and about 22%, between about 15% and about 20%, between about 15% and about 18%, between about 20% and about 30%, between about 20% and about 28%, between about 20% and about 26%, between about 20% and about 24%, between about 20% and about 22%, between about 25% and about 30%, or between about 25% and about 28%) of the steady state production cell density. As one skilled in the art can appreciate, the appropriate volume of second cell culture to dispose into the third culture medium to arrive at an initial cell density in the range of about $0.25 \times 10^6$ cells/mL to about $10 \times 10^6$ cells/mL for the production cell culture can be determined from the cell density of the second cell culture and the volume of third culture medium in the production bioreactor. For example, the volume of the second cell culture disposed into the third culture medium can be, e.g., between 2.0 L and 800 L (e.g., any of the exemplary ranges of volumes of second cell culture described herein).

The production cell culture can have a volume, e.g., between about 50 L to about 20,000 L (e.g., between about 50 L and about 17,500 L, between about 50 L and about 15,000 L, between about 50 L and about 12,500 L, between about 50 L and about 10,000 L, between about 50 L and about 7,500 L, between about 50 L and about 5,000 L, between about 50 L and about 2,500 L, between about 50 L and about 1,000 L, between about 50 L and about 750 L, between about 50 L and about 500 L, between about 50 L and about 200 L, between about 50 L and about 100 L, between about 100 L and about 20,000 L, between about 100 L and about 17,500 L, between about 100 L and about 15,000 L, between about 100 L and about 12,500 L, between about 100 L and about 10,000 L, between about 100 L and about 7,500 L, between about 100 L and about 5,000 L, between about 100 L and about 2,500 L, between about 100 L and about 1,000 L, between about 100 L and about 750 L, between about 100 L and about 500 L, between about 100 L and about 250 L, between about 200 L and about 20,000 L, between about 200 L and about 17,500 L, between about 200 L and about 15,000 L, between about 200 L and about 12,500 L, between about 200 L and about 10,000 L, between about 200 L and about 7,500 L, between about 200 L and about 5,000 L, between about 200 L and about 2,500 L, between about 200 L and about 1,000 L, between about 200 L and about 750 L, between about 200 L and about 500 L, between about 200 L and about 250 L, between about 500 L and about 20,000 L, between about 500 L and about 17,500 L, between about 500 L and about 15,000 L, between about 500 L and about 12,500 L, between about 500 L and about 10,000 L, between about 500 L and about 7,500 L, between about 500 L and about 5,000 L, between about 500

L and about 2,500 L, between about 500 L and about 1,000 L, between about 500 L and about 750 L, between about 750 L and about 20,000 L, between about 750 L and about 17,500 L, between about 750 L and about 15,000 L, between about 750 L and about 12,500 L, between about 750 L and about 10,000 L, between about 750 L and about 7,500 L, between about 750 L and about 5,000 L, between about 750 L and about 2,500 L, between about 750 L and about 1,000 L, between about 1,000 L and about 20,000 L, between about 1,000 L and about 17,500 L, between about 1,000 L and about 15,000 L, between about 1,000 L and about 12,500 L, between about 1,000 L and about 10,000 L, between about 1,000 L and about 7,500 L, between about 1,000 L and about 5,000 L, between about 1,000 L and about 2,500 L, between about 2,500 L and about 20,000 L, between about 2,500 L and about 17,500 L, between about 2,500 L and about 15,000 L, between about 2,500 L and about 12,500 L, between about 2,500 L and about 10,000 L, between about 2,500 L and about 7,500 L, between about 2,500 L and about 5,000 L, between about 5,000 L and about 20,000 L, between about 5,000 L and about 17,500 L, between about 5,000 L and about 15,000 L, between about 5,000 L and about 12,500 L, between about 5,000 L and about 10,000 L, between about 5,000 L and about 7,500 L, between about 7,500 L and about 20,000 L, between about 7,500 L and about 17,500 L, between about 7,500 L and about 15,000 L, between about 7,500 L and about 12,500 L, between about 7,500 L and about 10,000 L, between about 10,000 L and about 20,000 L, between about 10,000 L and about 17,500 L, between about 10,000 L and about 15,000 L, between about 10,000 L and about 12,500 L, between about 12,500 L and about 20,000 L, between about 12,500 L and about 17,500 L, between about 12,500 L and about 15,000 L, between about 15,000 L and about 20,000 L, between about 15,000 L and about 17,500 L, or between about 17,500 L and about 20,000 L).

The production bioreactor used in these methods can have an internal volume, e.g., of between 100 L and about 25,000 L (e.g., between about 100 L and about 22,500 L, between about 100 L and about 20,000 L, between about 100 L and about 17,500 L, between about 100 L and about 15,000 L, between about 100 L and about 12,500 L, between about 100 L and about 10,000 L, between about 100 L and about 7,500 L, between about 100 L and about 5,000 L, between about 100 L and about 2,500 L, between about 100 L and about 1,000 L, between about 100 L and about 500 L, between about 100 L and about 250 L, between about 200 L and about 25,000 L, between about 200 L and about 22,500 L, between about 200 L and about 20,000 L, between about 200 L and about 17,500 L, between about 200 L and about 15,000 L, between about 200 L and about 12,500 L, between about 200 L and about 10,000 L, between about 200 L and about 7,500 L, between about 200 L and about 5,000 L, between about 200 L and about 2,500 L, between about 200 L and about 1,000 L, between about 200 L and about 750 L, between about 200 L and about 500 L, between about 200 L and about 250 L, between about 500 L and about 25,000 L, between about 500 L and about 22,500 L, between about 500 L and about 20,000 L, between about 500 L and about 17,500 L, between about 500 L and about 15,000 L, between about 500 L and about 12,500 L, between about 500 L and about 10,000 L, between about 500 L and about 7,500 L, between about 500 L and about 5,000 L, between about 500 L and about 2,500 L, between about 500 L and about 1,000 L, between about 500 L and about 750 L, between about 1,000 L and about 25,000 L, between about 1,000 L and about 22,500 L, between about 1,000 L and about 20,000 L, between about 1,000 L and about 17,500 L, between about 1,000 L and about 15,000 L, between about 1,000 L and about 12,500 L, between about 1,000 L and about 10,000 L, between about 1,000 L and about 7,500 L, between about 1,000 L and about 5,000 L, between about 1,000 L and about 2,500 L, between about 5,000 L and about 25,000 L, between about 5,000 L and about 22,500 L, between about 5,000 L and about 20,000 L, between about 5,000 L and about 17,500 L, between about 5,000 L and about 15,000 L, between about 5,000 L and about 12,500 L, between about 5,000 L and about 10,000 L, between about 5,000 L and about 7,500 L, between about 7,500 L and about 25,000 L, between about 7,500 L and about 22,500 L, between about 7,500 L and about 20,000 L, between about 7,500 L and about 17,500 L, between about 7,500 L and about 15,000 L, between about 7,500 L and about 12,500 L, between about 7,500 L and about 10,000 L, between about 10,000 L and about 25,000 L, between about 10,000 L and about 22,500 L, between about 10,000 L and about 20,000 L, between about 10,000 L and about 17,500 L, between about 10,000 L and about 15,000 L, between about 10,000 L and about 12,500 L, between about 12,500 L and about 25,000 L, between about 12,500 L and about 22,500 L, between about 12,500 L and about 20,000 L, between about 12,500 L and about 17,500 L, between about 12,500 L and about 15,000 L, between about 15,000 L and about 25,000 L, between about 15,000 L and about 22,500 L, between about 15,000 L and about 20,000 L, between about 15,000 L and about 17,500 L, between about 17,500 L and about 25,000 L, between about 17,500 L and about 22,500 L, between about 17,500 L and about 20,000 L, between about 20,000 L and about 25,000 L, between about 20,000 L and about 22,500 L, or between about 22,500 L and about 25,000 L).

A production bioreactor can be any suitable bioreactor (e.g., large scale perfusion bioreactor, a batch bioreactor, or a fed-batch bioreactor) known in the art. For example, suitable production bioreactors are available from Xcellerex, Thermo Fisher, and GE Healthcare. For example, large scale production bioreactors (e.g., perfusion, batch, or fed-batch bioreactors) are manufactured by Holloway American (Springfield, Mo.) and assembled onto a bioreactor skid at Cotter Brothers Corporation (Danvers, Mass.).

Mammalian Cells

A recombinant mammalian cell can be a human, mouse, hamster, or monkey cell. For example, a recombinant mammalian cell can be a cell line, e.g., Chinese hamster ovary (CHO) cells (e.g., CHO DG44 cells, CHO-Kls cells, CO2.31 clonal cells, A14.13 clonal cells, C02.57 clonal cells, and F05.43 clonal cells), Sp2.0, myeloma cells (e.g., NS/0), B-cells, hybridoma cells, T-cells, human embryonic kidney (HEK) cells (e.g, HEK 293E and HEK 293F), African green monkey kidney epithelial cells (Vero) cells, or Madin-Darby Canine (Cocker Spaniel) kidney epithelial cells (MDCK) cells.

A nucleic acid encoding a recombinant protein can be introduced into a mammalian cell to produce a recombinant mammalian cell using a wide variety of methods known in molecular biology and molecular genetics. Non-limiting examples include transfection (e.g., lipofection), transduction (e.g., lentivirus, adenovirus, or retrovirus infection), and electroporation. In some instances, the nucleic acid that encodes a recombinant protein is not stably integrated into a chromosome of the recombinant mammalian cell (transient transfection), while in other recombinant mammalian cells the nucleic acid is integrated. Alternatively or in addition, the nucleic acid encoding a recombinant protein can be present in a plasmid and/or in a mammalian artificial chromosome (e.g., a human artificial chromosome). Alternatively or in addition, the nucleic acid can be introduced into the mammalian cell using a viral vector (e.g., a lentivirus, retrovirus, or adenovirus vector). The nucleic acid can be operably linked to a promoter sequence (e.g., a strong promoter, such as a β-actin promoter and CMV promoter, or an inducible promoter). A vector including the nucleic acid can, if desired, also include a selectable marker (e.g., a gene that confers hygromycin, puromycin, or neomycin resistance to the mammalian cell).

Liquid Culture Medium

Liquid culture media (culture media) are known in the art. A liquid culture media can be supplemented with a mammalian serum (e.g., fetal calf serum and bovine serum), and/or a growth hormone or growth factor (e.g., insulin, transferrin, and epidermal growth factor). Any of the liquid culture media described herein can be selected from the group of: animal-derived component free liquid culture medium, serum-free liquid culture medium, serum-containing liquid culture medium, chemically-defined liquid culture medium, and protein-free liquid culture medium. Non-limiting examples of chemically-defined liquid culture media, animal-derived component free liquid culture media, serum-free liquid culture media, and serum-containing liquid culture media are commercially available.

A liquid culture medium typically includes an energy source (e.g., a carbohydrate, such as glucose), essential amino acids (e.g., the basic set of twenty amino acids plus cysteine), vitamins and/or other organic compounds required at low concentrations, free fatty acids, and/or trace elements. The liquid culture media (e.g., a first and/or second liquid culture medium) can, if desired, be supplemented with, e.g., a mammalian hormone or growth factor (e.g., insulin, transferrin, or epidermal growth factor), salts and buffers (e.g., calcium, magnesium, and phosphate salts), nucleosides and bases (e.g., adenosine, thymidine, and hypoxanthine), protein and tissue hydrolysates, and/or any combination of these additives.

A wide variety of different liquid culture media that can be used to culture cells (e.g., mammalian cells) in any steps of any of the methods described herein are known in the art. Medium components that also may be useful in the present processes include, but are not limited to, chemically-defined (CD) hydrolysates, e.g., CD peptone, CD polypeptides (two or more amino acids), and CD growth factors. Additional examples of liquid tissue culture medium and medium components are known in the art.

Liquid culture medium obtained from a recombinant mammalian cell culture can be filtered or clarified to obtain a liquid culture medium that is substantially free of cells and/or viruses. Methods for filtering or clarifying a liquid culture medium in order to remove cells are known in the art (e.g., 0.2-μm filtration, filtration using an Alternating Tangential Flow (ATF™) system, a tangential flow filtration (TFF) system, or any of the systems described in U.S. Provisional Patent Application No. 61/878,502). Recombinant cells can also be removed from liquid culture medium using centrifugation and removing the supernatant that is liquid culture medium that is substantially free of cells, or by allowing the cells to settle to the gravitational bottom of a container (e.g., vessel) containing the liquid culture medium, and removing the liquid culture medium (the liquid culture medium that is substantially free of cells) that is distant from the settled recombinant mammalian cells. In some embodiments, the one or more (e.g., two, three, or all) of the first culture medium, the second culture medium, the third culture medium, and the fourth culture medium are identical.

The liquid culture medium used in any of the steps in any of the methods described herein can be any of the types of liquid culture medium described herein or known in the art. In any of the exemplary methods for isolating a recombinant protein described herein, a liquid culture medium obtained from a production cell culture can be diluted by addition of a second fluid (e.g., a buffer) before it is fed into the first MCCS (e.g., first PCCS).

The liquid culture medium containing a recombinant protein (e.g., a recombinant therapeutic protein) that is substantially free of cells can be stored (e.g., at a temperature below about 15° C. (e.g., below about 10° C., below about 4° C., below about 0° C., below about −20° C., below about −50° C., below about −70 C°, or below about −80° C.) for at least 1 day (e.g., at least about 2 days, at least about 5 days, at least about 10 days, at least about 15 days, at least about 20 days, or at least about 30 days) prior to isolating the recombinant protein (e.g., prior to feeding the liquid culture medium into the first MCCS (e.g., first PCCS)). Alternatively, in some examples the liquid culture medium containing a recombinant protein that is substantially free of cells is fed into a system used to isolate the recombinant protein (e.g., fed into the first MCCS (e.g., first PCCS) directly from the production bioreactor (e.g., fed into the first MCCS (e.g., first PCCS) directly from the production bioreactor after a filtering or clarification step).

Recombinant Proteins

A recombinant protein can be a recombinant therapeutic protein. Non-limiting examples of recombinant therapeutic proteins that can be produced by the methods provided herein include immunoglobulins (including light and heavy chain immunoglobulins, antibodies, or antibody fragments (e.g., any of the antibody fragments described herein), enzymes (e.g., a galactosidase (e.g., an alpha-galactosidase), Myozyme®, or Cerezyme®), proteins (e.g., human erythropoietin, tumor necrosis factor (TNF), or an interferon alpha or beta), or immunogenic or antigenic proteins or protein fragments (e.g., proteins for use in a vaccine). The recombinant therapeutic protein can be an engineered antigen-binding polypeptide that contains at least one multifunctional recombinant protein scaffold (see, e.g., the recombinant antigen-binding proteins described in Gebauer et al., *Current Opin. Chem. Biol.* 13:245-255, 2009; and U.S. Patent Application Publication No. 2012/0164066 (herein incorporated by reference in its entirety)). Non-limiting examples of recombinant therapeutic proteins that are antibodies include: panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, amatuximab, anatumomab, anrukinzumab, apolizumab, arcitumomab, atinumab, tocilizumab, basilizimab, bectumomab, belimumab, bevacizumab, besilesomab, bezlotoxumab, biciromab, canakinumab, certolizumab, cetuximab, cixutumumab, daclizumab, denosumab, densumab, eculizumab, edrecolomab, efalizumab, efungumab, epratuzumab, ertumaxomab, etaracizumab, figitumumab, golimumab, ibritumomab tiuxetan, igovomab, imgatuzumab, infliximab, inolimomab, inotuzumab, labetuzumab, lebrikizumab, moxetumomab, natalizumab, obinutuzumab, oregovomab, palivizumab, panitumumab, pertuzumab, ranibizumab, rituximab, tocilizumab, tositumomab, tralokinumab, tucotuzumab, trastuzumab, veltuzumab, zalutumumab, and zatuximab. Additional examples of recombinant therapeutic antibodies that can be produced by the methods described herein are known in the art. Additional non-limiting examples of recombinant therapeutic proteins that can be produced by the present methods include: alglucosidase alfa, laronidase, abatacept, galsulfase, lutropin alfa, antihemophilic factor, agalsidase beta, interferon beta-la, darbepoetin alfa, tenecteplase, etanercept, coagulation factor IX, follicle stimulating hormone, interferon beta-la, imiglucerase, dornase alfa, epoetin alfa, insulin or insulin analogs, mecasermin, factov VIII, factor VIIa, anti-thrombin III, protein C, human albumin, erythropoietin, granulocute colony stimulating factor, granulocyte macrophage colony stimulating factor, interleukin-11, laronidase, idursuphase, galsulphase, α-1-proteinase inhibitor, lactase, adenosine deaminase, tissue plasminogen activator, thyrotropin alpha (e.g., Thyrogen®) and alteplase. Additional examples of recombinant proteins that can be produced by the present methods include acid α-glucosidase, alglucosidase alpha (e.g., Myozyme® and Lumizyme®), α-L-iduronidase (e.g., Aldurazyme®), iduronate sulfatase, heparan N-sulfatase, galactose-6-sulfatase, acid β-galactosidase, β-glucoronidase, N-acetylglucosamine-1-phosphotransferase, α-N-acetylgalactosaminidase, acid lipase, lysosomal acid ceramidase, acid sphingomyelinase, β-glucosidase (e.g., Cerezyme® and Ceredase®), galactosylceramidase, α-galactosidase-A (e.g., Fabrazyme®), acid β-galactosidase, β-galactosidase, neuraminidase, hexosaminidase A, and hexosaminidase B.

A secreted, soluble recombinant protein can be recovered from the liquid culture medium by removing or otherwise physically separating the liquid culture medium from the cells (e.g., mammalian cells). A variety of different methods for removing liquid culture medium from cells (e.g., mammalian cells) are known in the art, including, for example, centrifugation, filtration, pipetting, and/or aspiration. The secreted recombinant therapeutic protein can then be recovered and isolated from the liquid culture medium using a variety of biochemical techniques including various types of chromatography (e.g., affinity chromatography, molecular sieve chromatography, cation exchange chromatography, hydrophobic interaction chromatography, or anion exchange chromatography) and/or filtration (e.g., molecular weight cut-off filtration).

Culturing Parameters

Any of the batch or perfusion culturing steps described herein can be performed at a temperature of about 31° C. to about 40° C. Skilled practitioners will appreciate that the temperature can be changed at specific time point(s) in during the culturing step, e.g., on an hourly or daily basis. For example, the temperature can be changed or shifted (e.g., increased or decreased) at about one day, two days, three days, four days, five days, six days, seven days, eight days, nine days, ten days, eleven days, twelve days, fourteen days, fifteen days, sixteen days, seventeen days, eighteen days, nineteen days, or about twenty days or more after the initial seeding of the vessel (e.g., bioreactor) with the cells (e.g., recombinant mammalian cells). For example, the temperature can be shifted upwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.). For example, the temperature can be shifted downwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.).

The perfusion and batch culturing steps described herein can further include exposing the liquid culture medium in the vessel, perfusion bioreactor, or production bioreactor to an atmosphere containing at most or about 15% $CO_2$ (e.g., at most or about 14% $CO_2$, 12% $CO_2$, 10% $CO_2$, 8% $CO_2$, 6% $CO_2$, 5% $CO_2$, 4% $CO_2$, 3% $CO_2$, 2% $CO_2$, or at most or about 1% $CO_2$). The vessel, perfusion bioreactor, or production bioreactor can incubate the cell culture in a controlled humidified atmosphere (e.g., at a humidity of greater than 20%, 30%, 40%, 50%, 60%, 70%, 75%, 80%, 85%, 90%, or 95%, or a humidity of 100%). The perfusion and production bioreactor can also be equipped with a mechanical device that is capable of removing a volume of liquid culture medium from the bioreactor and optionally, a filter within the mechanical device that removes the cells from the liquid culture medium during the process of transfer of the liquid culture medium out of the bioreactor (e.g., an ATF system).

The interior surface of any of the vessels, perfusion bioreactors, or production bioreactors described herein may have at least one coating (e.g., at least one coating of gelatin, collagen, poly-L-ornithine, polystyrene, and laminin), and as is known in the art, one or more ports for the sparging of $O_2$, $CO_2$, and $N_2$ into the liquid culture medium, a stir mechanism for agitating the liquid culture medium, and one or more sensors (e.g., dissolved $O_2$ and dissolved $CO_2$ sensors).

Methods for Making a Recombinant Protein

Also provided are methods of producing a recombinant protein that include any of the exemplary seed train processes described above and the additional steps of (f) perfusion culturing the production cell culture under conditions that allow the recombinant mammalian cells to secrete a recombinant protein, and harvesting the recombinant protein from the production cell culture.

Other methods of producing a recombinant protein include any of the exemplary seed train processes provided herein and the additional steps of (f) batch or feed-batch culturing the production cell culture under conditions that allow the recombinant cells to secrete a recombinant protein, and harvesting the recombinant protein from the production cell culture.

Perfusion culturing of the production cell culture can be performed using any of the exemplary perfusion culturing methods described herein or known in the art. For example, the period of time between the generation of the production cell culture (after disposing the second cell culture into the third culture medium) to the time that the production cell culture reaches the steady state production cell density is between about 1.5 days and about 5.0 days (e.g., between about 1.5 days and about 4.0 days, between about 1.5 days and about 3.5 days, between about 1.5 days and about 3.0 days, about 1.5 days and about 2.5 days, about 1.5 days and 2.0 days, between about 2.0 days and about 5.0 days, between about 2.0 days and about 4.5 days, between about 2.0 days and about 4.0 days, between about 2.0 days and about 3.5 days, between about 2.0 days and about 3.0 days, between about 2.0 days and about 2.5 days, between about 2.5 days and about 5 days, between about 2.5 days and about 4.5 days, between about 2.5 days and about 4.0 days, between about 2.5 days and about 3.5 days, between about 2.5 days and about 3.0 days, between about 3.0 days and about 5.0 days, between about 3.0 days and about 4.5 days, between about 3.0 days and about 4.0 days, between about 3.0 days and about 3.5 days, between about 3.5 days and about 5.0 days, between about 3.5 days and about 4.5 days, between about 3.5 days and about 4.0 days, between about 4.0 days and about 5.0 days, between about 4.0 days and about 4.5 days, or between about 4.5 days and about 5.0 days). The perfusion culturing of the production cell culture can be continued for, e.g., a period of, e.g., between 5.0 days and 200 days (e.g., between 5.0 days and 190 days, between 5.0 days and 180 days, between 5.0 days and 170 days, between 5.0 days and 160 days, between 5.0 days and 150 days, between 5.0 days and 140 days, between 5.0 days and 130 days, between 5.0 days and 120 days, between 5.0 days and 110 days, between 5.0 days and 110 days, between 5.0 days and 100 days, between 5.0 days and 90 days, between 5.0 days and 80 days, between 5.0 days and 70 days, between 5.0 days and 60 days, between 5.0 days and 50 days, between 5.0 days and 40 days, between 5.0 days and 30 days, between 5.0 days and 20 days, between 5.0 days and 10 days, between 10 days and 200 days, between 10 days and 190 days, between 10 days and 180 days, between 10 days and 170 days, between 10 days and 160 days, between 10 days and 150 days, between 10 days and 140 days, between 10 days and 130 days, between 10 days and 120 days, between 10 days and 110 days, between 10 days and 100 days, between 10 days and 90 days, between 10 days and 80 days, between 10 days and 70 days, between 10 days and 60 days, between 10 days and 50 days, between 10 days and 40 days, between 10 days and 30 days, between 10 days and 20 days, between 20 days and 200 days, between 20 days and 190 days, between 20 days and 180 days, between 20 days and 170 days, between 20 days and 160 days, between 20 days and 150 days, between 20 days and 140 days, between 20 days and 130 days, between 20 days and 120 days, between 20 days and 110 days, between 20 days and 100 days, between 20 days and 90 days, between 20 days and 80 days, between 20 days and 70 days, between 20 days and 60 days, between 20 days and 50 days, between 20 days and 40 days, between 30 days and 200 days, between 30 days and 190 days, between 30 days and 180 days, between 30 days and 170 days, between 30 days and 160 days, between 30 days and 150 days, between 30 days and 140 days, between 30 days and 130 days, between 30 days and 120 days, between 30 days and 110 days, between 30 days and 100 days, between 30 days and 90 days, between 30 days and 80 days, between 30 days and 70 days, between 30 days and 60 days, between 30 days and 50 days, between 30 days and 40 days, between 40 days and 200 days, between 40 days and 190 days, between 40 days and 180 days, between 40 days and 170 days, between 40 days and 160 days, between 40 days and 150 days, between 40 days and 140 days, between 40 days and 130 days, between 40 days and 120 days, between 40 days and 110 days, between 40 days and 100 days, between 40 days and 90 days, between 40 days and 80 days, between 40 days and 70 days, between 40 days and 60 days, between 40 days and 50 days, between 50 days and 200 days, between 50 days and 190 days, between 50 days and 180 days, between 50 days and 170 days, between 50 days and 160 days, between 50 days and 150 days, between 50 days and 140 days, between 50 days and 130 days, between 50 days and 120 days, between 50 days and 110 days, between 50 days and 100 days, between 50 days and 90 days, between 50 days and 80 days, between 50 days and 70 days, between 50 days and 60 days, between 75 days and 200 days, between 75 days and 175 days, between 75 days and 150 days, between 50 days and 125 days, between 50 days and 100 days, between 50 days and 75 days, between 75 days and 200 days, between 75 days and 175 days, between 75 days and 200 days, between 75 days and 175 days, between 75 days and 150 days, between 75 days and 125 days, between 75 days and 100 days, between 100 days and 200 days, between 100 days and 175 days, between 100 days and 150 days, between 100 days and 125 days, between 125 days and 200 days, between 125 days and 175 days, between 125 days and 150 days, between 150 days and 200 days, between 150 days and 175 days, or between 175 days and 200 days).

The culture medium can be removed from the production bioreactor by continuous or periodic removal (e.g., at the same or varying frequencies during the perfusion culturing). The culture medium can be removed manually (e.g., by pipetting) or by a pump system (e.g., an alternating tangential flow (ATF) filtration system or tangential fluid filtration).

Isolating the Recombinant Protein

The methods of producing a recombinant protein described herein can further include a step of isolating the recombinant protein from the culture medium removed from the production bioreactor (during perfusion culturing). The step of isolating the recombinant protein from the culture medium removed from the production bioreactor can include the performance of one or more (e.g., two, three, four, five, six, or seven) unit operations selected from the group of: capturing, purifying, polishing, inactivating viruses, adjusting the ionic concentration and/or pH of a fluid including the recombinant protein, and filtering. For example, one or more unit operations to isolate a recombinant protein can be performed by passing a fluid containing the recombinant protein through one or more (e.g., two, three, four, or five) multi-column chromatography systems (MCCSs). The step of isolating the recombinant protein from the culture medium can be performed using an integrated and continuous process (e.g., exemplary processes are described in U.S. Provisional Patent Application No. 61/775,060, U.S. Provisional Patent Application No. 61/856,390, U.S. patent application Ser. No. 14/195,481, International Patent Application No. PCT/US2014/019909, and U.S. Provisional Patent Application No. 61/928,906, the entire contents of each of the following applications are herein incorporated by reference). Exemplary processes can include providing a liquid culture medium including a recombinant protein (e.g., a recombinant therapeutic protein) that is substantially free of cells (e.g., liquid culture medium removed from the production bioreactor and filtered through an ATF system). Some processes include continuously feeding the liquid culture medium (e.g., the liquid culture medium removed from the production bioreactor and filtered through an ATF system) into a multi-column chromatography system (MCCS) that includes at least one chromatography column, where these processes are integrated and run continuously from the liquid culture medium to an eluate from the MCCS that is the isolated recombinant protein. Some processes include continuously feeding the liquid culture medium (e.g., the liquid culture medium removed from the production bioreactor and filtered through an ATF system) into a first MCCS (MCCS1), capturing the recombinant protein from the liquid culture medium using the MCCS1, producing an eluate from the MCCS1 that includes the recombinant protein and continuously feeding the eluate into a second MCCS (MCCS2), and subsequently eluting the recombinant protein (from the MCCS2) to thereby produce the isolated recombinant protein, where the processes are integrated and run continuously from the liquid culture medium to the isolated recombinant protein. Some embodiments further include a step of formulating the isolated recombinant protein into a pharmaceutical agent.

Non-limiting aspects of the MCCSs that can be used in any of these processes (MCCS, MCCS1, and/or MCCS2) are described in U.S. Provisional Patent Application No. 61/775,060, U.S. Provisional Patent Application No. 61/856,390, U.S. patent application Ser. No. 14/195,481, International Patent Application No. PCT/US2014/019909, and U.S. Provisional Patent Application No. 61/928,906 (each incorporated herein by reference). Various additional aspects of these exemplary processes are described in below and can be used in any combination in the processes provided herein without limitation. Exemplary aspects of the provided processes are described below; however, one skilled in the art will appreciate that additional steps can be added to the processes described herein and other materials can be used to perform any of the steps of the processes described herein.

The exemplary processes described herein can include the use of a MCCS or two or more (e.g., two, three, four, five, or six) multi-column chromatography systems (MCCSs) (e.g., an MCCS1 and MCCS2). A MCCS can include two or more chromatography columns, two or more chromatographic membranes, or a combination of at least one chromatography column and at least one chromatographic membrane. In non-limiting examples, a MCCS (e.g., MCCS, MCCS1, and/or MCCS2 in any of the processes herein) can include four chromatographic columns, three chromatographic columns and a chromatographic membrane, three chromatographic columns, two chromatographic columns, two chromatographic membranes, and two chromatographic columns and one chromatographic membrane. Additional examples of combinations of chromatography columns and/or chromatographic membranes can be envisioned for use in an MCCS (e.g., MCCS, MCCS1, and/or MCCS2 in any of the processes described herein) by one skilled in the art without limitation. The individual chromatography columns and/or chromatographic membranes present in a MCCS can be identical (e.g., have the same shape, volume, resin, capture mechanism, and unit operation), or can be different (e.g., have one or more of a different shape, volume, resin, capture mechanism, and/or unit operation). The individual chromatography column(s) and/or chromatographic membrane(s) present in a MCCS (e.g., MCCS, MCCS1, and/or MCCS2 in any of the processes described herein) can perform the same unit operation (e.g., the unit operation of capturing, purifying, or polishing) or different unit operations (e.g., different unit operations selected from, e.g., the group of capturing, purifying, polishing, inactivating viruses, adjusting the ionic concentration and/or pH of a fluid including the recombinant protein, and filtering). For example, in examples of the processes described herein, at least one chromatography column and/or chromatographic membrane in the MCCS or MCCS1 performs the unit operation of capturing the recombinant protein.

The one or more chromatography column(s) in an MCCS (e.g., the MCCS, MCCS1, and/or MCCS2) used in any of the processes described herein can have the substantially the same resin volume or can have different resin volumes. One or more (e.g., three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) different types of buffer can be employed during the use of the MCCS, MCCS1, and/or MCCS2 in any of the processes described herein. As is known in the art, the one or more types of buffer used in the MCCS, MCCS1, and/or MCCS2 in the processes described herein will depend on the resin present in the chromatography column(s) and/or the chromatographic membrane(s) of the MCCS, MCCS1, and/or MCCS2, the biophysical properties of the recombinant protein, and unit operation (e.g., any of the exemplary unit operations described herein) performed by the specific chromatography column(s) and/or chromatography membranes of the MCCS, MCCS1, and/or MCCS2. The volume and type of buffer employed during the use of the MCCS, MCCS1, and/or MCCS2 in any of the processes described herein can also be determined by one skilled in the art (e.g., discussed in more detail below). For example, the volume and type(s) of buffer employed during the use of the MCCS, MCCS1, and/or MCCS2 in any of the processes described herein can be chosen in order to optimize one or more of the following in the isolated recombinant protein: the overall yield of recombinant protein, the activity of the recombinant protein, the level of purity of the recombinant protein, and the removal of biological contaminants from a fluid including the recombinant protein (e.g., liquid culture medium) (e.g., absence of active viruses, mycobacteria, yeast, bacteria, or mammalian cells).

The MCCS, MCCS1, and/or MCCS2 can be a periodic counter current chromatography system (PCCS). A PCCS can, e.g., include two or more chromatography columns (e.g., three columns or four columns) that are switched in order to allow for the continuous elution of recombinant protein from the two or more chromatography columns. A PCCS can include two or more chromatography columns, two or more chromatographic membranes, or at least one chromatographic column and at least one chromatographic membrane. A column operation (cycle) generally consists of the load, wash, eluate, and regeneration steps. In PCCSs, multiple columns are used to run the same steps discretely and continuously in a cyclic fashion. Since the columns are operated in series, the flow through and wash from one column is captured by another column. This unique feature of PCCSs allows for loading of the resin close to its static binding capacity instead of to the dynamic binding capacity, as is typical during batch mode chromatography. As a result of the continuous cycling and elution, fluid entering a PCCS is processed continuously, and the eluate including recombinant protein is continuously produced.

Column-switching strategy is employed to advance from one step to another in a PCCS cycle. Examples of column switching that can be used in a PCCS are described in U.S. Provisional Patent Application No. 61/775,060, U.S. Provisional Patent Application No. 61/856,390, U.S. patent application Ser. No. 14/195,481, International Patent Application No. PCT/US2014/019909, and U.S. Provisional Patent Application No. 61/928,906. In PCCSs, the residence time (RT) of the recombinant protein on the each chromatography column and/or chromatographic membrane present in the PCCS can be decreased without increasing the column/membrane size because the breakthrough from the first column/membrane can be captured on another column/membrane in the PCCS. A continuous process system can be designed to process liquid culture medium at any perfusion rate (D) by varying the column/membrane volume (V) and RT using the equation of: $V = D * RT$.

The one or more unit operations that can be performed by the MCCS or the MCC1 and/or MCCS2 used in the presently described processes include, for example, capturing the recombinant protein, inactivating viruses present in a fluid including the recombinant protein, purifying the recombinant protein, polishing the recombinant protein, holding a fluid including the recombinant protein (e.g., using any of the exemplary break tank(s) described herein), filtering or removing particulate material and/or cells from a fluid including the recombinant protein, and adjusting the ionic concentration and/or pH of a fluid including the recombinant protein. In some embodiments, the MCCS or the MCCS1 includes at least one chromatographic column and/or chromatographic membrane that performs the unit operation of capturing the recombinant protein. The unit operation of capturing can be performed using at least one chromatography column and/or chromatography resin, e.g., that utilizes a capture mechanism. Non-limiting examples of capturing mechanisms include a protein A-binding capture mechanism, an antibody- or antibody fragment-binding capture mechanism, a substrate-binding capture mechanism, an aptamer-binding capture mechanism, a tag-binding capture mechanism (e.g., poly-His tag-based capture mechanism), and a cofactor-binding capture mechanism. Capturing can also be performed using a resin that can be used to perform cation exchange or anion exchange chromatography, molecular sieve chromatography, or hydrophobic interaction chromatography. Non-limiting resins that can be used to capture a recombinant protein are described herein. Additional examples of resins that can be used to capture a recombinant protein are known in the art.

The unit operation of inactivating viruses present in a fluid including the recombinant protein can be performed using a MCCS, MCCS1, and/or MCCS2 (e.g., that include(s), e.g., a chromatography column, a chromatography membrane, or a holding tank that is capable of incubating a fluid including the recombinant protein at a pH of between about 3.0 to 5.0 (e.g., between about 3.5 to about 4.5, between about 3.5 to about 4.25, between about 3.5 to about 4.0, between about 3.5 to about 3.8, or about 3.75) for a period of at least 30 minutes (e.g., a period of between about 30 minutes to 1.5 hours, a period of between about 30 minutes to 1.25 hours, a period of between about 0.75 hours to 1.25 hours, or a period of about 1 hour)).

The unit operation of purifying a recombinant protein can be performed using one or more MCCSs (e.g., a MCCS, MCCS1, and/or MCCS2) that include(s), e.g., a chromatography column or chromatographic membrane that includes a resin, e.g., that utilizes a capture system. Non-limiting examples of capturing mechanisms include a protein A-binding capture mechanism, an antibody- or antibody fragment-binding capture mechanism, a substrate-binding capture mechanism, an aptamer-binding capture mechanism, a tag-binding capture mechanism (e.g., poly-His tag-based capture mechanism), and a cofactor-binding capture mechanism. Purifying can also be performed using a resin that can be used to perform cation exchange or anion exchange chromatography, molecular sieve chromatography, or hydrophobic interaction chromatography. Non-limiting resins that can be used to purify a recombinant protein are described herein. Additional examples of resins that can be used to purify a recombinant protein are known in the art.

The unit operation of polishing a recombinant protein can be performed using one or more MCCSs (e.g., a MCCS, MCCS1, and/or MCCS) that include(s), e.g., a chromatography column or chromatographic membrane that includes a resin, e.g., that can be used to perform cation exchange, anion exchange, molecular sieve chromatography, or hydrophobic interaction chromatography. Non-limiting resins that can be used to polish a recombinant protein are described herein. Additional examples of resins that can be used to polish a recombinant protein are known in the art.

The unit operation of filtering a fluid including the recombinant protein can be performed using an MCCS (e.g., the MCCS, MCCS1, and/or MCCS2) that includes, e.g., a filter, or a chromatography column or chromatographic membrane that includes a molecular sieve resin. As is known in the art, a wide variety of submicron filters (e.g., a filter with a pore size of less than 1 µm, less than 0.5 µm, less than 0.3 µm, about 0.2 µm, less than 0.2 µm, less than 100 nm, less than 80 nm, less than 60 nm, less than 40 nm, less than 20 nm, or less than 10 nm) are available in the art that are capable of removing any precipitated material and/or cells (e.g., precipitated, unfolded protein; precipitated, unwanted host cell proteins; precipitated lipids; bacteria; yeast cells; fungal cells; mycobacteria; and/or mammalian cells). Filters having a pore size of about 0.2 µm or less than 0.2 µm are known to effectively remove bacteria from the fluid including the recombinant protein. As is known in the art, a chromatography column or a chromatographic membrane including a molecular sieve resin can also be used in an MCCS (e.g., the MCCS, MCCS1, and/or MCCS2) to perform the unit operation of filtering a fluid including a recombinant protein.

The unit operations of adjusting the ionic concentration and/or pH of a fluid including the recombinant protein can be performed using a MCCS (e.g., a MCCS, a MCCS1, and/or a MCCS2) that includes and utilizes a buffer adjustment reservoir (e.g., an in-line buffer adjustment reservoir) that adds a new buffer solution into a fluid that includes the recombinant protein (e.g., between columns within the MCCS, MCCS1, and/or MCCS2, or after the last column in a penultimate MCCS (e.g., the MCCS1) and before the fluid including the recombinant protein is fed into the first column of the next MCCS (e.g., the MCCS2)).

In the exemplary processes described herein, the MCCS, MCCS1, and/or MCCS2 can perform two or more unit operations. For example, the MCCS, MCCS1, and/or MCCS2 can each perform at least the following unit operations: capturing the recombinant protein and inactivating viruses present in the fluid including the recombinant protein; capturing the recombinant protein, inactivating viruses present in the fluid including the recombinant protein, and adjusting the ionic concentration and/or pH of a liquid including the recombinant protein; purifying the recombinant protein and polishing the recombinant protein; purifying the recombinant protein, polishing the recombinant protein, and filtering a fluid including the recombinant protein or removing precipitates and/or particular matter from a fluid including the recombinant protein; and purifying the recombinant protein, polishing the recombinant protein, filtering a fluid including the recombinant protein or removing precipitates and/or particulate matter from a fluid including the recombinant protein, and adjusting the ionic concentration and/or pH of a liquid including the recombinant protein.

In the exemplary processes described herein, the capturing of the recombinant protein from the liquid culture medium is performed using the MCCS or MCCS1. As can be appreciated in the art, in order to achieve the capture of the recombinant protein, at least one chromatographic column or at least one chromatographic membrane in the MCCS or MCCS1 must include a resin that utilizes a capturing mechanism (e.g., any of the exemplary capturing mechanisms described herein), or includes a resin capable of performing cation exchange, anion exchange, molecular sieve, or hydrophobic interaction chromatography. For example, if the recombinant protein is an antibody or an antibody fragment, the capturing system can be a protein A-binding capturing mechanism or an antigen-binding capturing mechanism (where the capturing antigen is specifically recognized by the recombinant antibody or antibody fragment). If the recombinant protein is an enzyme, the capturing mechanism can use an antibody or antibody fragment that specifically binds to the enzyme to capture the recombinant enzyme, a substrate of the enzyme to capture the recombinant enzyme, a cofactor of the enzyme to capture the recombinant enzyme, or, if the recombinant enzyme includes a tag, a protein, metal chelate, or antibody (or antibody fragment) that specifically binds to the tag present in the recombinant enzyme. Non-limiting resins that can be used to capture a recombinant protein are described herein and additional resins that can be used to capture a recombinant protein are known in the art. One non-limiting example of resin that utilizes a protein A-binding capture mechanism is MabSelect SuRe resin (GE Healthcare, Piscataway, N.J.), JSR LifeSciences Amsphere ProA JWT203 (Sunnyvale, Calif.), and Kaneka KanCap A (Osaka, Japan).

In some of the exemplary processes described herein, the MCCS or MCCS1 can include a reservoir that holds a fluid including the recombinant protein at low pH (e.g., a pH below 4.6, below 4.4, below 4.2, below 4.0, below 3.8, below 3.6, below 3.4, below 3.2, or below 3.0) for, e.g., about 1 minute to 1.5 hours (e.g., about 1 hour), and inactivates the viruses present in a fluid including the recombinant protein. As can be appreciated by those skilled in the art, a variety of other means can be used to perform the unit operation of inactivating viruses. For example, UV irradiation of a fluid including the recombinant protein can also be used to perform the unit operation of inactivating viruses.

The MCCS or MCCS1 can include a PCCS including four chromatography columns, where at least three of the four chromatography columns perform the unit operation of capturing the recombinant protein from the liquid culture medium (e.g., using an MCCS that includes any of the at least one chromatography columns that include a resin that is capable of performing the unit operation of capturing (e.g., any of those described herein)). In these examples, the fourth-column of the PCC can perform the unit operation of inactivating viruses in a fluid that includes the recombinant protein (e.g., any of the exemplary columns described herein that can be used to achieve viral inactivation of a fluid including the recombinant protein).

The MCCS, MCCS1, and/or MCCS2 in the exemplary processes described herein can be used to perform the unit operation of purifying and polishing the recombinant protein. For example, the MCCS2 can be used to perform the operation of purifying and polishing the recombinant protein and the eluate from the MCCS2 is an isolated recombinant protein. The MCCS, MCCS1, and/or MCCS2 can include at least one (e.g., two, three, or four) chromatography column or chromatographic membrane that can be used to perform the unit operation of purifying a recombinant protein, and at least one (e.g., two, three, or four) chromatography column or chromatographic membrane that can be used to perform the unit operation of polishing the recombinant protein.

The at least one chromatography column or chromatographic membrane that can be used to perform the unit operation of purifying the recombinant protein can include a resin that utilizes a capture mechanism (e.g., any of the capture mechanisms described herein or known in the art), or a resin that can be used to perform anion exchange, cation exchange, molecular sieve, or hydrophobic interaction chromatography. The at least one chromatography column or chromatographic membrane that can be used to perform the unit of operation of polishing the recombinant protein can include a resin that can be used to perform anion exchange, cation exchange, molecular sieve, or hydrophobic interaction chromatography (e.g., any of the exemplary resins for performing anion exchange, cation exchange, molecular sieve, or hydrophobic interaction chromatography described herein or known in the art). The one or more chromatography column(s) and/or chromatographic membranes used to perform the unit operation of polishing can include a resin that selectively binds or retains the impurities present in a fluid including the recombinant protein.

In some examples of the exemplary processes described herein, the MCCS2 includes a PCCS including three chromatography columns and one chromatographic membrane, e.g., where the three chromatography columns in the PCCS perform the unit operation of purifying the recombinant protein (e.g., using at least one chromatography column(s) that can be used to perform the unit of operation of purifying the protein) and the chromatographic membrane in the PCCS performs the unit operation of polishing the recombinant protein. In these examples, the chromatographic membrane in the PCCS that can be used to perform the unit operation of polishing the recombinant protein can be any of the exemplary chromatographic membranes described herein that can be used to perform the unit operation of polishing the recombinant protein. Any of the column switching methods described herein can be used to determine when the first three chromatography columns and the chromatographic membrane in the PCCS in this example can be switched.

Exemplary Recombinant Protein Isolation Systems

Examples of biological manufacturing systems useful for performing the processes described herein and that include a MCCS or a MCCS1 and MCCS2 are described in U.S. Provisional Patent Application Ser. Nos. U.S. Provisional Patent Application No. 61/775,060, U.S. Provisional Patent Application No. 61/856,390, U.S. patent application Ser. No. 14/195,481, International Patent Application No. PCT/US2014/019909, and U.S. Provisional Patent Application No. 61/928,906 (incorporated by reference). The entire system can include, e.g., a total of four, five, six, seven, eight, nine, ten, eleven, twelve, thirteen, fourteen, fifteen, sixteen, seventeen, eighteen, nineteen, or twenty chromatography columns. For example, the MCCS, MCCS1, and/or MCCS2 can include (or can each include) two, three, four, five, six, seven, eight, nine, or ten of chromatography columns.

For example, useful systems can include a MCCS1 that includes an inlet and a MCCS2 that includes an outlet, or an MCCS that includes an inlet and an outlet. In some embodiments, the MCCS1 and MCCS2 are in fluid communication with each other. These systems can also be configured such that fluid can be passed into the inlet, through the MCCS1 and MCCS2, and exit the manufacturing system through the outlet.

In these exemplary systems, the MCCS or MCCS1 can include an inlet through which fluid (e.g., liquid culture medium from the production bioreactor that is substantially free of cells) can be passed into the MCCS or MCCS1, respectively. The inlet can be any structure known in the art for such purposes. It can include, e.g., a threading, ribbing, or a seal that allows for a fluid conduit to be inserted, such that after insertion of the fluid conduit into the inlet, fluid will enter the MCCS or MCCS1 through the inlet without significant seepage of fluid out of the inlet. Non-limiting inlets that can be used in the present systems are known and would be understood by those in the art.

The MCCS or MCCS1 can include at least two chromatography columns, at least two chromatographic membranes, or at least one chromatography column and at least one chromatographic membrane, and an inlet. The MCCS or MCCS1 can be any of the exemplary MCCSs described herein, or have one or more of any of the exemplary features of an MCCS (in any combination) described herein. The chromatography column(s) and/or the chromatographic membrane(s) present in the MCCS or MCCS1 can have one or more of any of the exemplary shapes, sizes, volumes (bed volumes), and/or unit operation(s) described herein or known in the art.

The chromatography column(s) and/or the chromatographic membrane(s) present in the MCCS or MCCS1 can include one or more of any of the exemplary resins described herein or known in the art. For example, the resin included in one or more of the chromatography column(s) and/or chromatographic membrane(s) present in the MCCS or MCCS1 can be a resin that utilizes a capture mechanism (e.g., protein A-binding capture mechanism, protein G-binding capture mechanism, antibody- or antibody fragment-binding capture mechanism, substrate-binding capture mechanism, cofactor-binding capture mechanism, an aptamer-binding capture mechanism, and/or a tag-binding capture mechanism). The resin included in one or more of the chromatography column(s) and/or chromatographic membrane(s) of the MCCS or MCCS1 can be a cation exchange resin, an anion exchange resin, a molecular sieve resin, or a hydrophobic interaction resin, or any combination thereof. Additional examples of resins that can be used to purify a recombinant protein are known in the art, and can be included in one or more of the chromatography column(s) and/or chromatographic membrane(s) present in the MCCS or MCCS1. The chromatography column(s) and/or chromatography membranes present in the MCCS or MCCS1 can include the same and/or different resins (e.g., any of the resins described herein or known in the art for use in recombinant protein purification).

The two or more chromatography column(s) and/or chromatographic resin(s) present in the MCCS or MCCS1 can perform one or more unit operations (e.g., capturing a recombinant protein, purifying a recombinant protein, polishing a recombinant protein, inactivating viruses, adjusting the ionic concentration and/or pH of a fluid including the recombinant protein, or filtering a fluid including a recombinant protein). In non-limiting examples, the MCCS or MCCS1 can perform the unit operations of capturing a recombinant protein from a fluid (e.g., a liquid culture medium) and inactivating viruses present in the fluid including the recombinant protein. The MCCS or MCCS1 can perform any combinations of two of more unit operations described herein or known in the art.

The chromatography column(s) and/or chromatographic membrane(s) present in the MCCS or MCCS1 can be connected or moved with respect to each other by a switching mechanism (e.g., a column-switching mechanism). The MCCS or MCCS1 can also include one or more (e.g., two, three, four, or five) pumps (e.g., automated, e.g., automated peristaltic pumps). The column-switching events can be triggered by the detection of a level of recombinant protein detected by UV absorbance corresponding to a certain level of recombinant protein in the fluid passing through the MCCS or MCCS1 (e.g., the input into and/or eluate from one or more of the chromatography column(s) and/or chromatographic membranes in the MCCS or MCCS1), a specific volume of liquid (e.g., buffer), or specific time elapsed. Column switching generally means a mechanism by which at least two different chromatography columns and/or chromatographic membranes in an MCCS or MCCS1 (e.g., two or more different chromatography columns and/or chromatographic membranes present in the MCCS1 or MCCS2) are allowed to pass through a different step (e.g., equilibration, loading, eluting, or washing) at substantially the same time during at least part of the process.

The MCCS or MCCS1 can be a Periodic Counter-Current Chromatography system (PCCS). For example, the PCCS that is the MCCS or MCCS1 (i.e., PCCS or PCCS1, respectively) can include four chromatography columns, where the first three columns perform the unit operation of capturing a recombinant protein from a fluid (e.g., a liquid culture medium), and the fourth column of the PCCS performs the unit operation of inactivating viruses in the fluid including the recombinant protein. A PCCS that is the MCCS or MCCS1 can utilize a column-switching mechanism. The PCC system can utilize a modified AKTA system (GE Healthcare, Piscataway, N.J.) capable of running up to, e.g., four, five, six, seven, or eight columns, or more.

The second MCCS (MCCS2) in the exemplary systems described herein can include at least two chromatography columns, at least two chromatographic membranes, or at least one chromatography column(s) and at least one chromatographic membrane(s), and an outlet. The MCCS2 can any of the exemplary MCCSs described herein, or can have one or more of any of the exemplary features of an MCCS (in any combination) described herein. The chromatography column(s) and/or the chromatographic membrane(s) present in the MCCS2 can have one or more of: any of the shapes, sizes, volumes (bed volumes), and/or unit operations described herein. The chromatography column(s) and/or the chromatographic membrane(s) can include any of the exemplary resins described herein or known in the art. For example, the resin included in one or more of the chromatography column(s) and/or chromatographic membrane(s) present in the MCCS2 can be a resin that utilizes a capture mechanism (e.g., protein A-binding capture mechanism, protein G-binding capture mechanism, antibody- or antibody fragment-binding capture mechanism, substrate-binding capture mechanism, cofactor-binding capture mechanism, tag-binding capture mechanism, and/or aptamer-binding capture mechanism). Useful resins include, e.g., a cation exchange resin, an anion exchange resin, a molecular sieve resin, and a hydrophobic interaction resin. Additional examples of resins are known in the art. The chromatography column(s) and/or chromatography membranes present in the MCCS2 can include the same and/or different resins (e.g., any of the resins described herein or known in the art for use in recombinant protein purification).

The chromatography column(s) and/or chromatographic membrane(s) present in the MCCS2 can perform one or more unit operations (e.g., any of the unit operations described herein or any combination of the unit operations described herein). In non-limiting examples, the MCCS2 can perform the unit operations of purifying a recombinant protein from a fluid and polishing the recombinant protein present in the fluid including the recombinant protein. In other non-limiting examples, the MCCS2 can perform the unit operations of purifying a recombinant protein present in a fluid, polishing a recombinant protein present in a fluid, and filtering a fluid including a recombinant protein. In another example, the MCCS2 can perform the unit operations of purifying a recombinant protein present in a fluid, polishing a recombinant protein present in a fluid, filtering a fluid including a recombinant protein, and adjusting the ionic concentration and/or pH of a fluid including a recombinant protein. The MCCS2 can perform any combination of two of more unit operations described herein or known in the art.

The chromatography column(s) and/or chromatographic membrane(s) present in the MCCS2 can be connected or moved with respect to each other by a switching mechanism (e.g., a column-switching mechanism). The MCCS2 can also include one or more (e.g., two, three, four, or five) pumps (e.g., automated, e.g., automated peristaltic pumps). The column-switching events can be triggered by the detection of a level of recombinant protein detected by UV absorbance corresponding to a certain level of recombinant protein in the fluid passing through the MCCS2 (e.g., the input into and/or eluate from one or more of the chromatography column(s) and/or chromatographic membranes in the MCCS2), a specific volume of liquid (e.g., buffer), or specific time elapsed.

The MCCS2 can be a Periodic Counter-Current Chromatography system (i.e., PCCS2). For example, the PCCS2 can include three columns that perform the unit operation of purifying a recombinant protein from a fluid, and a chromatographic membrane that performs the unit operation of polishing a recombinant protein present in a fluid. For example, the three columns that perform the unit operation of purifying a recombinant protein from a fluid can include, e.g., a cationic exchange resin, and the chromatographic membrane that performs the unit operation of polishing can include a cationic exchange resin. A PCCS2 can utilize a column-switching mechanism. The PCCS2 can utilize a modified AKTA system (GE Healthcare, Piscataway, N.J.) capable of running up to, e.g., four, five, six, seven, or eight columns, or more.

The MCCS2 can include an outlet through which the isolated recombinant protein can exit the system. The outlet can include, e.g., a threading, ribbing, or a seal that allows for a fluid conduit to be inserted or a vial designed to hold or store the isolated recombinant protein. An outlet can include a surface that can be used to seal a reduced bioburden vial or other such storage container onto the outlet in order to allow the isolated recombinant protein to flow directly into the reduced bioburden vial or storage container. Non-limiting outlets that can be used in the present systems are known and would be understood by those in the art.

Formulating an Isolated Recombinant Protein

The isolated recombinant protein can further be formulated into a pharmaceutical agent using methods known in the art. Pharmaceutical agents are formulated to be compatible with their intended route of administration (e.g., intravenous, intraarterial, intramuscular, intradermal, subcutaneous, or intraperitoneal). The pharmaceutical agents can include a sterile diluent (e.g., sterile water or saline), a fixed oil, polyethylene glycol, glycerin, propylene glycol, or other synthetic solvents, antibacterial or antifungal agents, such as benzyl alcohol or methyl parabens, chlorobutanol, phenol, ascorbic acid, thimerosal, and the like, antioxidants, such as ascorbic acid or sodium bisulfite, chelating agents, such as ethylenediaminetetraacetic acid, buffers, such as acetates, citrates, or phosphates, and isotonic agents, such as sugars (e.g., dextrose), polyalcohols (e.g., mannitol or sorbitol), or salts (e.g., sodium chloride), or any combination thereof. Liposomal suspensions can also be used as pharmaceutically acceptable carriers (see, e.g., U.S. Pat. No. 4,522,811). Preparations of the pharmaceutical agents can be formulated and enclosed in ampules, disposable syringes, or multiple dose vials. Where required (as in, for example, injectable formulations), proper fluidity can be maintained by, for example, the use of a coating, such as lecithin, or a surfactant. Absorption of the isolated recombinant protein can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Pharmaceutical agents that include one or more of any of the isolated recombinant proteins can be formulated for parenteral (e.g., intravenous, intraarterial, intramuscular, intradermal, subcutaneous, or intraperitoneal) administration in dosage unit form (i.e., physically discrete units containing a predetermined quantity of active protein for ease of administration and uniformity of dosage).

Toxicity and therapeutic efficacy of the pharmaceutical agents can be determined by standard pharmaceutical procedures in cell cultures or experimental animals (e.g., monkeys). One can, for example, determine the LD50 (the dose lethal to 50% of the population) and the ED50 (the dose therapeutically effective in 50% of the population): the therapeutic index being the ratio of LD50:ED50. Pharmaceutical agents that exhibit high therapeutic indices are preferred. Where a pharmaceutical agent exhibits an undesirable side effect, care should be taken to minimize potential damage (i.e., reduce unwanted side effects). Toxicity and therapeutic efficacy can be determined by other standard pharmaceutical procedures.

Data obtained from cell culture assays and animal studies can be used in formulating an appropriate dosage of any given isolated recombinant protein for use in a subject (e.g., a human). The effectiveness and dosing of any of the pharmaceutical agents described herein can be determined by a health care professional or veterinary professional using methods known in the art. Certain factors may influence the dosage and timing required to effectively treat a subject (e.g., the severity of the disease or disorder, previous treatments, the general health and/or age of the subject, and the presence of other diseases).

The invention is further described in the following examples, which do not limit the scope of the invention described in the claims.

EXAMPLES

Example 1. Two-Step Exemplary Seed Train Processes

Figure 2:
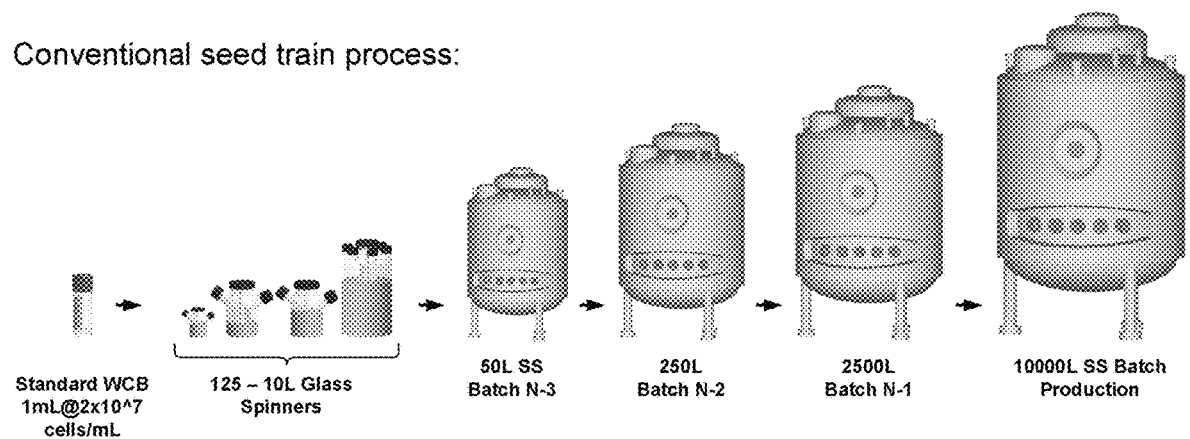
FIG. 2 is a schematic diagram showing a conventional seed train process that ends in the inoculation of a 10,000-L production batch or fed-batch bioreactor (top) and a schematic diagram of an exemplary seed train process provided herein that ends in the inoculation of a 10,000-L production batch or fed-batch bioreactor (bottom).
Figure 2:
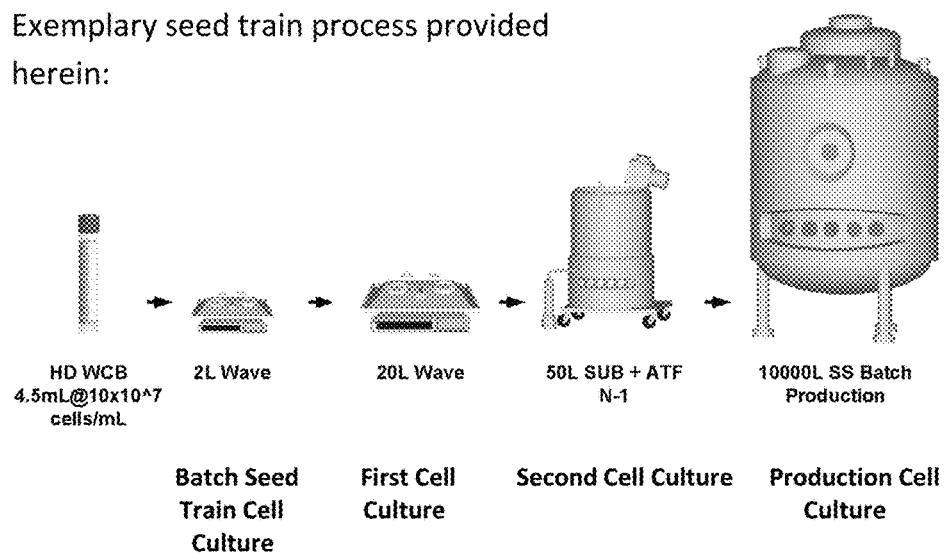

Experiments were performed to develop improved seed train processes. Exemplary seed train processes provided herein are shown in FIGS. 1 and 2. Compared to conventional seed train processes, the exemplary seed train processes provided herein eliminate two intermediate spinner culturing steps. The exemplary seed train processes shown in FIGS. 1 and 2 replace the spinner cultures (e.g., 125-mL to 10-L spinner cultures in FIGS. 1 and 2) with Wave bioreactors (2-L and 20-L) in FIGS. 1 and 2). The replacement of the multiple spinner cultures with Wave bioreactors in FIGS. 1 and 2 reduces the number of required manipulations in a laminar flow hood, and thus improves the operational success by allowing operation under a closed system. Use of perfusion culturing at the N−1 perfusion culture step (e.g., a 50-L perfusion bioreactor with an ATF filtration device in FIGS. 1 and 2) also allows for culture cell densities of $\geq 50 \times 10^6$ viable cells/mL to be reached. The high viable cell densities achieved in the N−1 perfusion culturing step allows for an inoculation density of $5 \times 10^6$ viable cells/mL in a 500-L production bioreactor, which is significantly higher than the initial cell density in the production bioreactor achieved by conventional seed train processes (FIG. 1). The higher production bioreactor seeding density provided by the present seed train processes helps to reduce the production bioreactor growth phase by about 5 days saving in manufacturing plant time for a production bioreactor operating for 50 days. The materials and methods used to test the productivity of the exemplary seed train processes shown in FIGS. 1 and 2 are described below.

Materials and Methods

Cell Line and Media

All experiments were performed using a commercially available, chemically-defined cell culture medium (Life Technologies, Grand Island, N.Y.) supplemented with 4 mM glutamine (Sigma-Aldrich, St. Louis, Mo.) and a CHO cell line producing a recombinant human enzyme.

Batch Seed Train Culture in 2-L and 20-L Wave Bioreactors

A high density (HD) cell bank vial ($10 \times 10^7$ viable cells/mL, 4.5 mL/vial) was thawed into a 2-L Wave cell bag (GE Healthcare, Piscataway, N.J.) at a 1-L working volume. When the viable cell density in the 2-L Wave cell bag reached $3.0 \times 10^6$ viable cells/mL, the culture was expanded into a 20-L Wave cell bag at a 7.5-L working volume. A Wave bioreactor system (Model 20/50 EHTD) (GE Healthcare) was used as the rocking platform for both 2-L and 20-L Wave cell bags. Cultures were maintained at a temperature of 37° C., 16 RPM rocking speed, and 7° rocking angle. A gas mixture of 20% $O_2$ and 5% $CO_2$ was added to the headspace at a flow rate of 0.25 slpm.

Seed Train N−1 Perfusion Culture

A 15-L glass perfusion bioreactor (Broadley-James Corporation, Irvine, Calif.) equipped with an ATF4 perfusion device (Refine Technology, Pine Brook, N.J.) was used to mimic the seed train N−1 stage (50-L bioreactor as shown in FIG. 1). Oxygen was added through a 20-μm sintered sparger to control dissolved oxygen at 40% and nitrogen was added through a 1-mm drilled hole sparger to control dissolved $CO_2$ level below 120 mmHg. The bioreactor culture pH was maintained above 6.85 through addition of 0.5 M sodium carbonate. A 10% antifoam solution (FoamAway, Life Technologies, Grand Island, N.Y.) was added to control the foam level as needed.

The 15-L bioreactor at 10-L working volume was seeded at $0.5 \times 10^6$ viable cells/mL and the culture was operated in batch mode until day 2 when perfusion was started. The perfusion rate was initially controlled at a cell-specific perfusion rate (CSPR) of 0.2 nL/cell/day using an online capacitance sensor (Aber Instruments, Aberystwyth, UK) and a programmable logic controller (DeltaV). The perfusion rate was capped at 4 bioreactor volumes per day (RV/day) after the viable cell density reached $20 \times 10^6$ cells/mL.

50-mL Spin Tube Batch Re-Feed Model for Inoculation Density Evaluation

An aliquot of the culture was removed from the seed train N−1 bioreactor when its cell density reached $25 \times 10^6$ viable cells/mL, $50 \times 10^6$ viable cells/mL, and $100 \times 10^6$ viable cells/mL and subsequently inoculated into 50-mL spin tubes (TPP Techno Plastic Products AG, Trasadingen, Switzerland) at three different inoculation densities in triplicate: $0.5 \times 10^6$ viable cells/mL, $2.5 \times 10^6$ viable cells/mL, or $5.0 \times 10^6$ viable cells/mL in a working volume of 10 mL. Re-feeds were done once daily since continuous perfusion could not be performed at this scale. The re-feeds were performed starting on day 1 by removing the spin tubes from the incubator, spinning cells down at 1100 RPM for 5 minutes, removing the supernatant, and then adding fresh media to re-suspend the cells. The re-feed strategy was designed to provide the same CSPR across different inoculation density conditions. All spin tubes were maintained in a Multitron II shaking incubator (HT Infors, Bottmingen, Switzerland) at a temperature of 37° C., rocking rate of 160 RPM, rocking angle of 45 degrees relative to the benchtop, relative humidity of 80%, and $CO_2$ concentration of 5%.

Production Bioreactor

To mimic the 500-L production bioreactor shown in FIG. 1, 15-L bioreactors (Broadley-James Corporation, Irvine, Calif.) with a working volume of 10 L were operated in perfusion mode using an ATF4 perfusion device (Refine Technology, Pine Brook, N.J.) with 20-μm sintered sparger to control dissolved oxygen at 40% and nitrogen was added through a 1-mm drilled hole sparger to maintain dissolved $CO_2$ level below 120 mmHg. The pH was maintained above 6.85 through addition of 0.5 M sodium carbonate. A 10% antifoam solution (FoamAway, Life Technologies, Grand Island, N.Y.) was added through a peristaltic pump to control the foam level.

One set of production bioreactors was inoculated at a low density ($0.5 \times 10^6$ viable cells/mL) from a seed vessel that was operated in batch mode. Perfusion was started on day 1 at 0.5 RV/day and increased daily by 0.5 RV/day until a 2 RV/day perfusion rate was reached. Another set of production reactors was inoculated at a high density ($5.0 \times 10^6$ viable cells/mL) from an N−1 15-L perfusion seed vessel when the density reached $50 \times 10^6$ viable cells/mL. Due to the high inoculation density, perfusion was started at 2 RV/day immediately after inoculation. For all production bioreactors, the viable cell density was controlled at $40 \times 10^6$ viable cells/mL using an online capacitance sensor and bleed pump. All production bioreactors were operated for 50 days.

Analytical Methods

Viable cell density was determined using a ViCell XR Cell Viability Analyzer (Beckman Coulter, Brea, Calif.). Offline pH and $pCO_2$ were measured using a RAPIDLab Blood Gas Analyzer (Siemans, Tarrytown, N.Y.). Protein productivity was measured by a proprietary photometric enzymatic activity assay.

Results and Discussion

Figure 3:
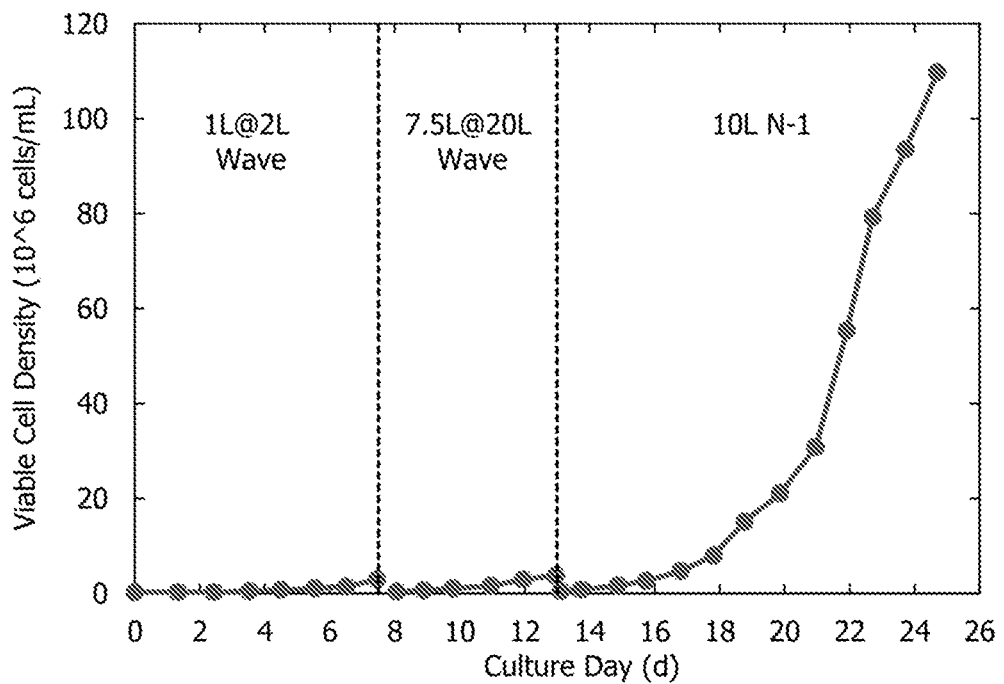
FIG. 3 is a graph showing the viable cell density throughout the steps of an exemplary seed train process described herein: batch culturing a 1-L third cell culture in a 2-L disposable single-use bioreactor, batch culturing a 7.5-L first cell culture in a 20-L disposable single-use bioreactor, and perfusion culturing a 10-L second cell culture in a 15-L perfusion bioreactor.

FIG. 3 shows the viable cell density growth profile of the exemplary seed train process described in these examples, including batch Wave cultures and an N−1 perfusion culture. The durations of the batch 2-L and 20-L Wave cultures were 8 days and 5 days, respectively. The N−1 perfusion bioreactor was operated for 12 days and reached a final viable cell density of $110 \times 10^6$ viable cells/mL and ≥98% cell viability. The viable cell density reached $50 \times 10^6$ cells/mL on day 9, which is the cell density required to inoculate a 500-L bioreactor at $5 \times 10^6$ viable cells/mL (from a 50-L N−1 bioreactor).

Figure 4:
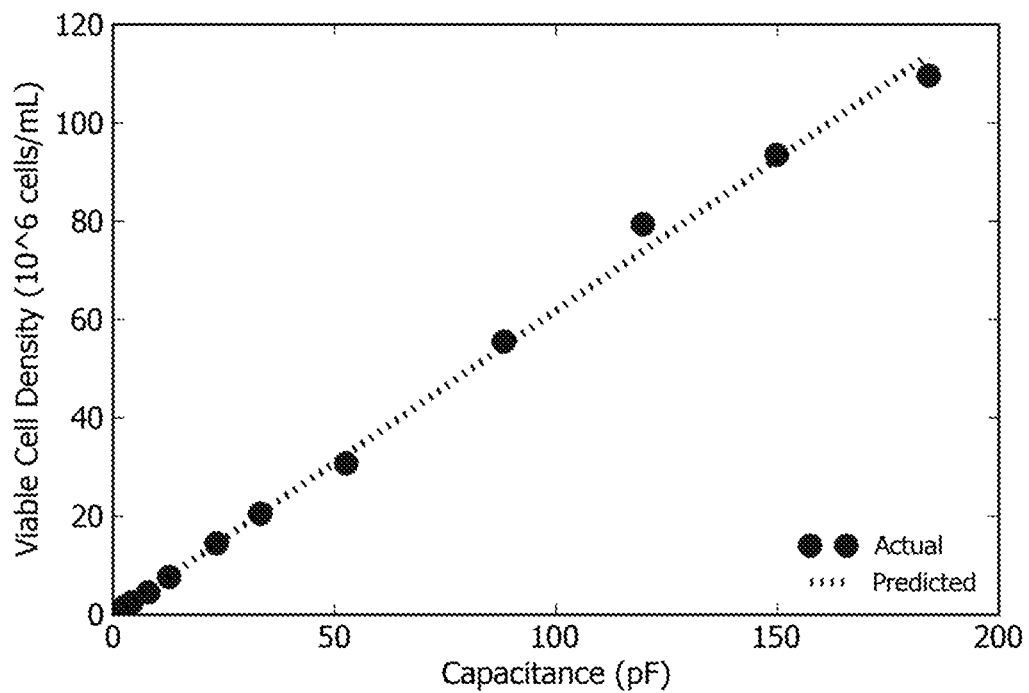
FIG. 4 is a graph of the viable cell density as a function of capacitance of N–1 perfusion cell culture in an exemplary seed train process described herein.

For the N−1 bioreactor, perfusion was initiated on day 2 and controlled to maintain a CSPR of 0.2 nL/cell/day using an online capacitance probe to automatically increase feed rate as the cell density increased. The success of this perfusion rate control strategy depends on the ability of the capacitance probe to accurately estimate the viable cell density. This strategy was used only to day 7 because the perfusion rate was capped at 4 RV/day, but the probe was able to accurately estimate the density throughout the run to day 12 when $110 \times 10^6$ viable cells/mL was reached (FIG. 4).

A small-scale spin tube model was used to evaluate the impact of the N−1 cell density on cell growth in the production bioreactor. Samples of the culture were removed from an N−1 bioreactor when cell densities were at $25 \times 10^6$ viable cells/mL, $50 \times 10^6$ viable cells/mL, or $100 \times 10^6$ viable cells/mL, respectively. These were split into three aliquots, diluted to $0.5 \times 10^6$ viable cells/mL, $2.5 \times 10^6$ viable cells/mL, or $5 \times 10^6$ viable cells/mL with fresh media, and then inoculated in triplicate into spin tubes (modeling the perfusion production bioreactor). Daily re-feeds were not performed until day 1 due to the dilutions achieved when the cultures were split to their respective inoculation densities. The re-feed rate was adjusted based on the inoculation density of the spin tubes allowing each inoculation density condition to experience the same CSPR at corresponding cell densities.

Figure 5:
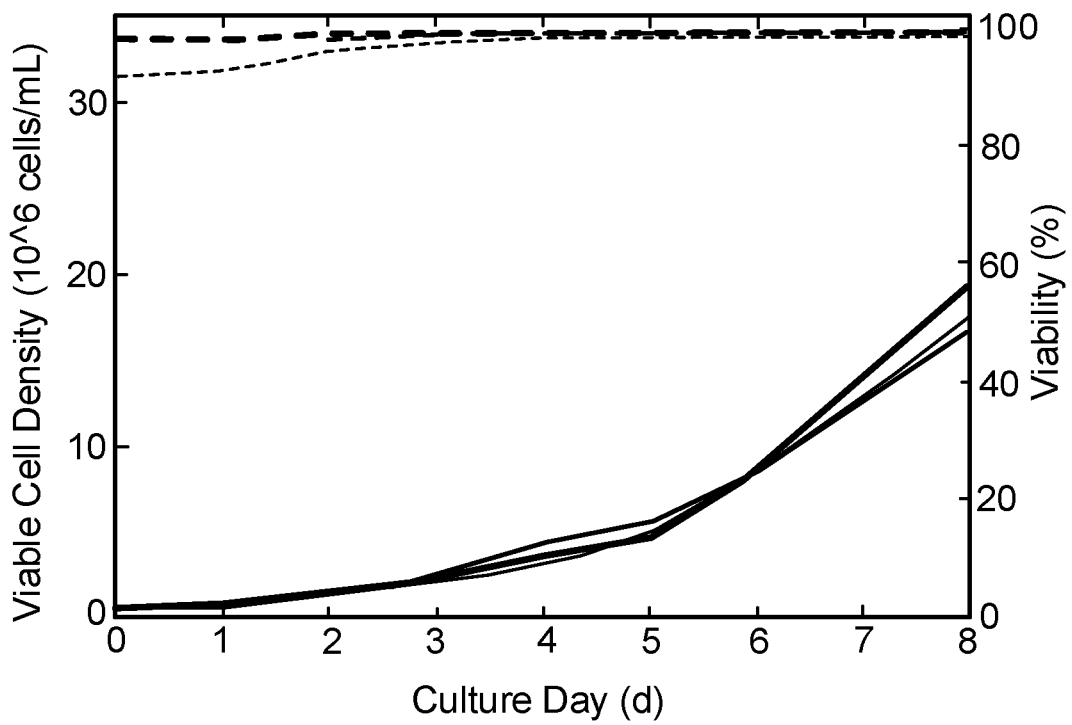
FIG. 5 is a graph of the viable cell density (solid lines) and percentage cell viability (dashed lines) over time for spin tubes inoculated with a volume of N–1 cell culture having a viable cell density of $25 \times 10^6$ cells/mL (heavy weight solid and dashed lines), $50 \times 10^6$ cells/mL (medium weight solid and dashed lines), or $100 \times 10^6$ cells/mL (light weight solid and dashed lines) to yield a starting viable cell density of $0.5 \times 10^6$ cells/mL in spin tubes (representing a production bioreactor). The solid and dashed lines represent the mean of the data (n=3). The shaded areas represent ±2 standard deviations.
Figure 6:
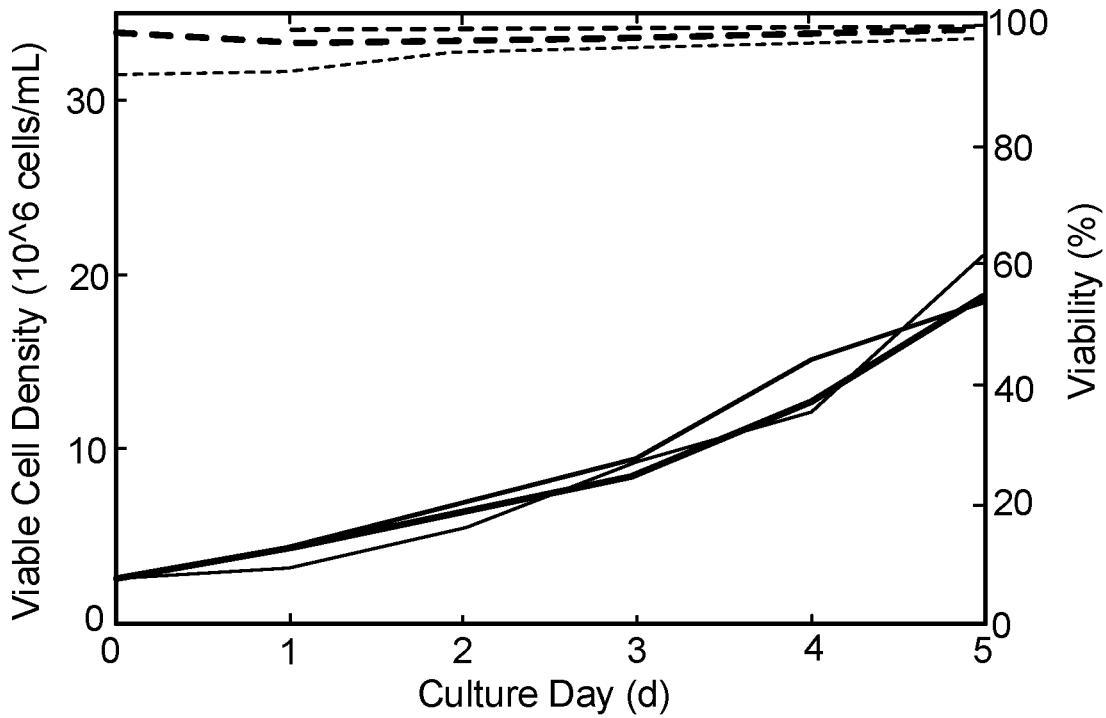
FIG. 6 is a graph of the viable cell density (solid lines) and percentage cell viability (dashed lines) over time for spin tubes inoculated with a volume of N–1 cell culture having a viable cell density of $25 \times 10^6$ cells/mL (medium weight solid and dashed lines), 50×10⁶ cells/mL (heavy weight solid and dashed lines), or 100×10⁶ cells/mL (light weight solid and dashed lines) to yield a starting viable cell density of 2.5×10⁶ cells/mL in spin tubes (representing a production bioreactor). The solid and dashed lines represent the mean of the data (n=3). The shaded areas represent ±2 standard deviations.
Figure 7:
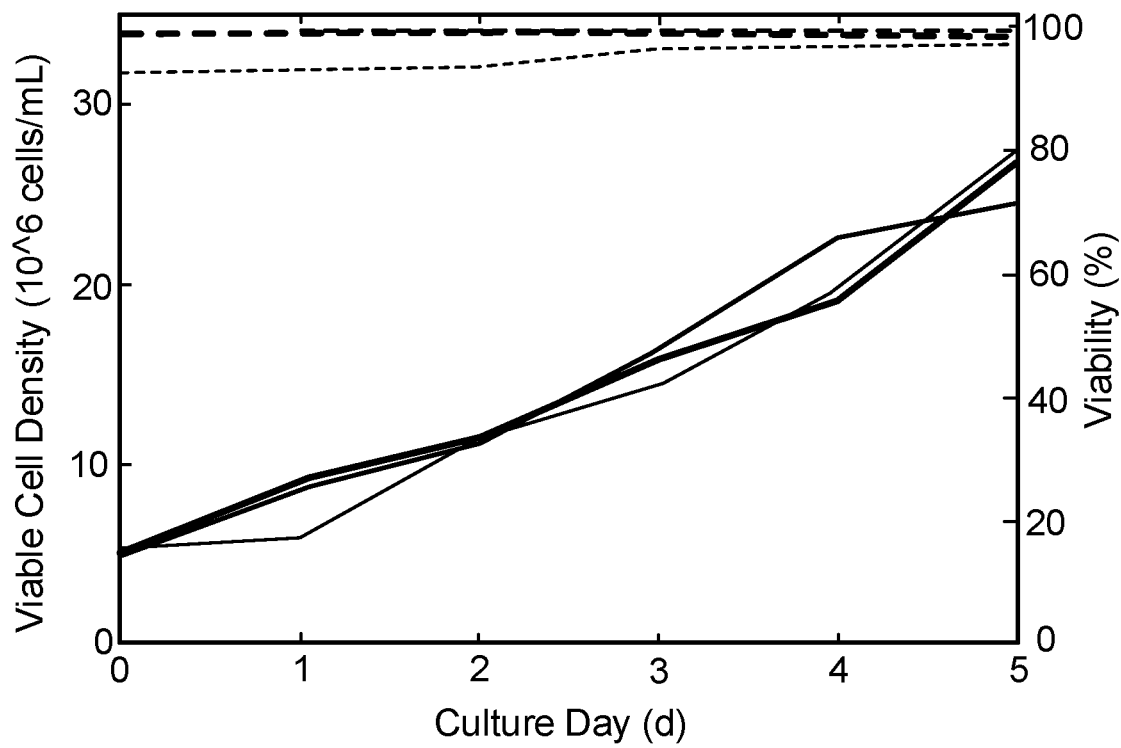
FIG. 7 is a graph of the viable cell density (solid lines) and percentage cell viability (dashed lines) over time for spin tubes inoculated with a volume of N-1 cell culture having a viable cell density of 25×10⁶ cells/mL (medium weight solid and dashed lines), 50×10⁶ cells/mL (heavy weight solid and dashed lines), or 100×10⁶ cells/mL (light weight solid and dashed lines) to yield a starting viable cell density of 5.0×10⁶ cells/mL in spin tubes (representing a production bioreactor). The solid and dashed lines represent the mean of the data (n=3). The shaded areas represent ±2 standard deviations.

Cell count and viability profiles are shown in FIGS. 5-7 and are plotted so that comparisons can be made between the N−1 density conditions at each inoculation density. Because the maximum perfusion rate in the spin tube model is 1 RV/day, there cultures were grown up only to $20 \times 10^6$ viable cells/mL to match CSPR to the perfusion bioreactor model. There were no observable growth differences between the different N−1 density conditions for all three inoculation densities tested.

Figure 8:
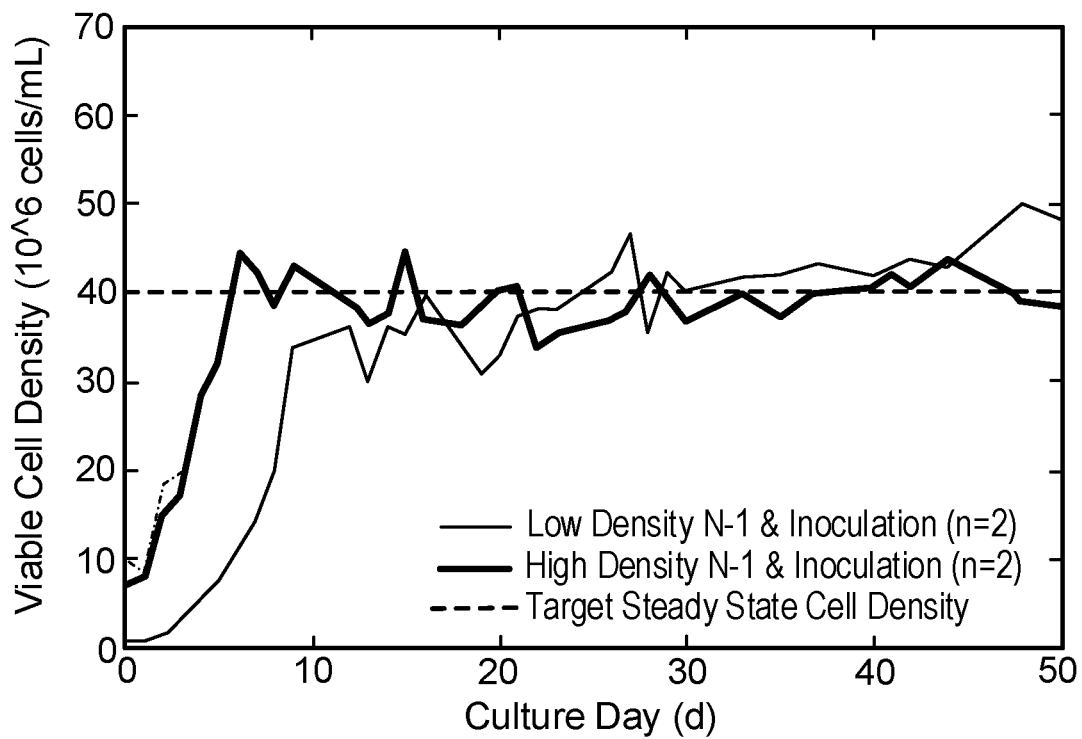
FIG. 8 is a graph of the viable cell density over time for 10-L production bioreactors inoculated at 0.5×10⁶ cells/mL from an N-1 perfusion bioreactor at 2.5×10⁶ viable cells/mL (n=2) (light weight line) compared to 10-L production bioreactors inoculated at 5.0×10⁶ viable cells/mL from an N-1 perfusion bioreactor at 50×10⁶ viable cells/mL (n=2) (heavy weight line). The dashed line represents the target viable cell density for steady state operation of the production bioreactor. The solid lines represent the mean of the data (n=2).
Figure 9:
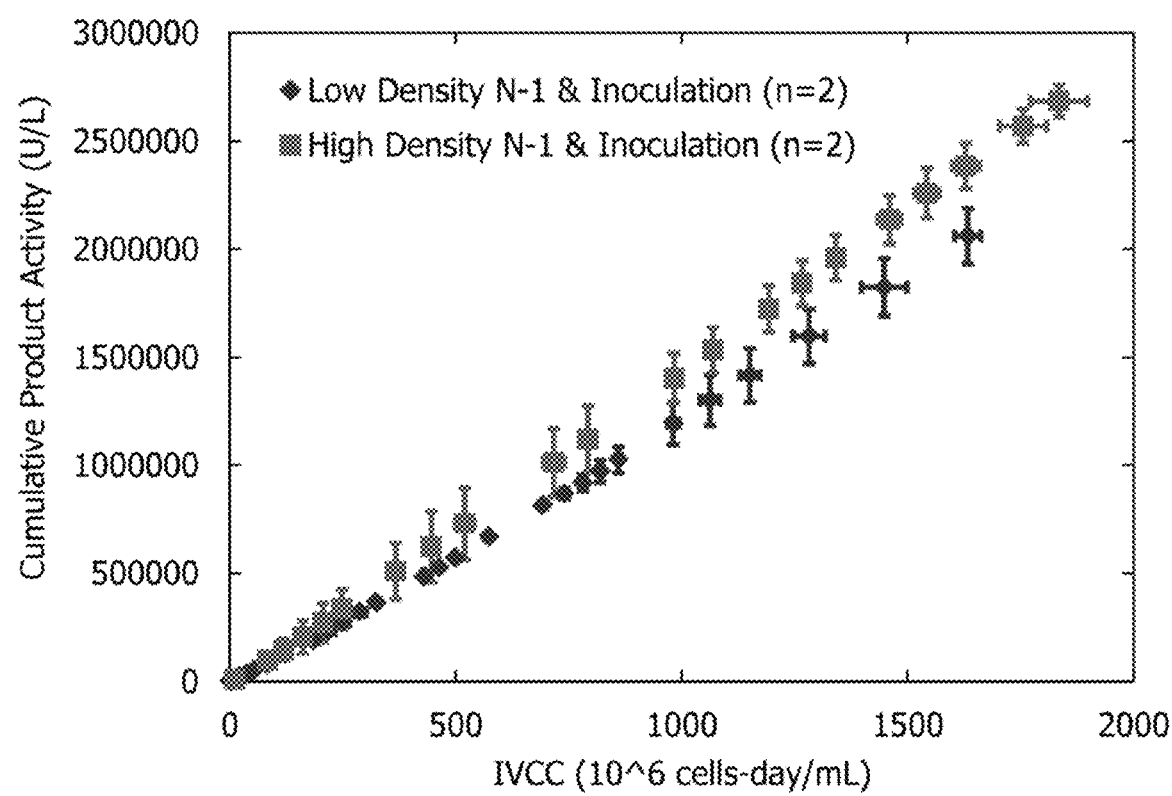
FIG. 9 is a graph showing the cumulative product activity (units/L) as a function of the integral viable cell concentration for 10-L production bioreactors inoculated at 0.5×10⁶ viable cells/mL from an N-1 perfusion bioreactor at 2.5×10⁶ viable cells/mL (diamonds) compared to 10-L production bioreactors inoculated at 5.0×10⁶ viable cells/mL from an N-1 bioreactor at 50×10⁶ cells/mL (squares). The data represent the mean of the data (n=2) and the error bars represent ±2 standard deviations.

To study the effects on N−1 density and inoculation density on production bioreactor cell growth and productivity, bioreactors were inoculated at $5.0 \times 10^6$ viable cells/mL from an N−1 bioreactor at $50 \times 10^6$ viable cells/mL and compared with bioreactors inoculated at $0.5 \times 10^6$ viable cells/mL from an N−1 bioreactor at $2.5 \times 10^6$ viable cells/mL. Cell growth for both conditions was comparable as shown in FIG. 8. The cell viability remained above 90% for both inoculation conditions throughout the 50-day run. FIG. 9 shows cumulative productivity versus integrated viable cell density and indicates a similar specific production rate between conditions. Most notably, the steady-state cell density of $40 \times 10^6$ viable cells/mL (FIG. 8) and the required titer for purification were reached 4-5 days earlier for the high inoculation density condition.

The exemplary seed train processes described herein have both economic and operational advantages. For example, inoculating a 500-L perfusion production bioreactor at $5.0 \times 10^6$ cells/mL reduces the growth phase duration by 4-5 days, increasing productivity by 10% for a 50-day run. Additionally, the N−1 perfusion bioreactors were able to reach $100 \times 10^6$ viable cells/mL, and could theoretically inoculate a 500-L bioreactor at $10 \times 10^6$ viable cells/mL, further reducing the growth phase duration (e.g., by a total of 5-6 days).

The exemplary seed train processes described herein can also be used to inoculate a production bioreactor that is operated in batch or fed-batch mode. For a 21-day fed-batch cell culture process using a 500-L bioreactor, an inoculation density of $5.0 \times 10^6$ viable cells/mL could reduce the production bioreactor duration by 25%. Overall, this could allow for an additional 5-6 batches per year, increasing manufacturing productivity by 25%-30%.

In most cases, batch and fed-batch processes typically use production bioreactors that are much larger than those used for perfusion processes, thus requiring several seed train stages in large-scale stainless steel bioreactors. FIG. 2 shows an example of a conventional seed train process used to inoculate a 10,000-L bioreactor compared to a seed train process using a 50-L N−1 bioreactor with an ATF perfusion device. Using the exemplary seed train processes described herein, the 50-L N−1 bioreactor at $50\text{-}100 \times 10^6$ viable cells/mL is able to inoculate a 10,000-L bioreactor at $0.25 \times 10^6$ viable cells/mL to $0.50 \times 10^6$ viable cells/mL, thus eliminating two intermediate seed train cell culturing stages.

The data described in this example demonstrate an exemplary seed train process involving HD cell banking, disposable single-use bioreactor technology, and perfusion culturing at the N−1 bioreactor stage. The seed train processes provided herein reduce the complexity of conventional seed train processes by decreasing the number of small-scale culturing stages. The data described in this example show that the use of perfusion culture at the N−1 stage can achieve viable cell densities up to $100 \times 10^6$ viable cells/mL in 12 days without compromising culture growth characteristics after further expansion steps. Based on these data, the exemplary seed train processes described herein can be used to inoculate at a 500-L production bioreactor at a cell density of $5 \times 10^6$ viable cells/mL to reduce the time to steady state cell density by 4-5 days and provide a 10% increase in the overall productivity of a 50-day run. For batch or batch processes that require larger production bioreactors, such as 10,000-L, the seed train processes provided herein can eliminate 1-2 stages from the expansion process by using a single 50-L perfusion bioreactor at the N−1 stage.

What is claimed is:

1. A method of producing a recombinant protein, wherein the method consists of:
    (a) disposing a plurality of recombinant mammalian cells into a first culture medium within a vessel to provide a first cell culture;
    (b) batch culturing the first cell culture to a cell density range of about $1.0 \times 10^6$ cells/mL to about $5.0 \times 10^6$ cells/mL;
    (c) disposing a volume of the first cell culture of step (b) into a second culture medium within a perfusion bioreactor to provide a second cell culture with an initial cell density in a range of about $0.25 \times 10^6$ cells/mL to about $0.5 \times 10^6$ cells/mL;
    (d) perfusion culturing the second cell culture to a cell density range of about $5 \times 10^6$ cells/mL to about $120 \times 10^6$ cells/mL;
    (e) disposing a volume of the second cell culture of step (d) into a third culture medium within a production bioreactor to provide a production cell culture with an initial cell density in a range of about $0.25 \times 10^6$ cells/mL to about $8 \times 10^6$ cells/mL;
    (f) perfusion culturing the production cell culture under conditions that allow the recombinant mammalian cells to secrete a recombinant protein; and
    (g) harvesting the recombinant protein from the production cell culture.

2. The method of claim 1, wherein the step of disposing the plurality of recombinant mammalian cells in (a) to provide a first cell culture consists of:
    thawing a frozen cell bank; and
    disposing a volume of the thawed cell bank into the first culture medium.

3. The method of claim 1, wherein the step of disposing the plurality of recombinant mammalian cells in (a) to provide a first cell culture consists of disposing a volume of cultured recombinant mammalian cells into the first culture medium.

4. The method of claim 1, wherein:
    the first cell culture in (a) has a volume range of about 1.0 L to about 50 L;
    the second cell culture in (c) has a volume range of about 5 L to about 600 L; and/or
    the production cell culture in (e) has a volume range of about 50 L to about 20,000 L.

5. The method of claim 1, wherein:
    the vessel in (a) has an internal volume range of about 1.5 L to about 100 L;
    the perfusion bioreactor in (c) has an internal volume range of about 7.5 L to about 1,000 L; and/or
    the production bioreactor in (e) has an internal volume range of about 150 L to about 25,000 L.

6. The method of claim 1, wherein:
    the initial cell density in the production cell culture is in a range of about $2.0 \times 10^6$ cells/mL to about $8 \times 10^6$ cells/mL; and/or
    the initial cell density in the production cell culture is at least 10% of a steady state production cell density.

7. A method of producing a recombinant protein, wherein the method consists of:
(a) disposing a plurality of recombinant mammalian cells into a fourth culture medium within a vessel to provide a third cell culture;
(b) batch culturing the third cell culture of (a) to a cell density range of about $1.0 \times 10^6$ cells/mL to about $5.0 \times 10^6$ cells/mL;
(c) disposing a volume of the third cell culture of (b) into a first culture medium within a vessel to provide a first cell culture;
(d) batch culturing the first cell culture to a cell density range of about $1.0 \times 10^6$ cells/mL to about $5.0 \times 10^6$ cells/mL;
(e) disposing a volume of the first cell culture of step (d) into a second culture medium within a perfusion bioreactor to provide a second cell culture with an initial cell density in a range of about $0.25 \times 10^6$ cells/mL to about $0.5 \times 10^6$ cells/mL;
(f) perfusion culturing the second cell culture to a cell density range of about $5 \times 10^6$ cells/mL to about $120 \times 10^6$ cells/mL;
(g) disposing a volume of the second cell culture of step (f) into a third culture medium within a production bioreactor to provide a production cell culture with an initial cell density in a range of about $0.25 \times 10^6$ cells/mL to about $8 \times 10^6$ cells/mL;
(h) perfusion culturing the production cell culture under conditions that allow the recombinant mammalian cells to secrete a recombinant protein; and
(i) harvesting the recombinant protein from the production cell culture.

8. The method of claim 7, wherein the step of disposing the plurality of the recombinant mammalian cells in (a) to provide the third cell culture consists of:
thawing a frozen cell bank; and
disposing a volume of the thawed cell bank into the fourth culture medium.

9. A method of producing a recombinant protein, wherein the method consists of:
(a) disposing a plurality of recombinant mammalian cells into a first culture medium within a vessel to provide a first cell culture;
(b) batch culturing the first cell culture to a cell density range of about $1.0 \times 10^6$ cells/mL to about $5.0 \times 10^6$ cells/mL;
(c) disposing a volume of the first cell culture medium of (b) into a second culture medium within a perfusion bioreactor to provide a second cell culture with an initial cell density in a range of about $0.25 \times 10^6$ cells/mL to about $0.5 \times 10^6$ cells/mL;
(d) perfusion culturing the second cell culture to a cell density range of about $5 \times 10^6$ cells/mL to about $60 \times 10^6$ cells/mL;
(e) disposing a volume of the second cell culture of (d) into a third culture medium within a production bioreactor to provide a production cell culture with an initial cell density in a range of about $0.5 \times 10^6$ cells/mL to about $10 \times 10^6$ cells/mL;
(f) perfusion culturing the production cell culture under conditions that allow the recombinant mammalian cells to secrete a recombinant protein; and
(g) harvesting the recombinant protein from the production cell culture.

10. The method of claim 9, wherein the step of disposing the plurality of recombinant mammalian cells in (a) to provide the first cell culture consists of:
thawing a frozen cell bank; and
disposing a volume of the thawed cell bank into the first culture medium.

11. The method of claim 9, wherein the step of disposing the plurality of recombinant mammalian cells in (a) to provide the first cell culture consists of disposing a volume of a third cell culture consisting of the plurality of recombinant mammalian cells in a fourth cell culture medium into the first culture medium.

12. The method of claim 9, wherein:
the first cell culture in (a) has a volume range of about 1.0 L to about 50 L;
the second cell culture in (c) has a volume range of about 5 L to about 600 L; and/or
the production cell culture in (e) has a volume range of about 50 L to about 20,000 L.

13. The method of claim 9, wherein:
the vessel in (a) has an internal volume range of about 1.5 L to about 100 L;
the perfusion bioreactor in (c) has an internal volume range of about 7.5 L to about 1,000 L; and/or
the production bioreactor in (e) has an internal volume range of about 150 L to about 25,000 L.

14. The method of claim 9, wherein:
the initial cell density in the production cell culture is in a range of about $2.0 \times 10^6$ cells/mL to about $8 \times 10^6$ cells/mL; and/or
the initial cell density in the production cell culture is at least 10% of a steady state production cell density.

15. The method of claim 9, wherein the perfusion culturing in (f) results in the production cell culture reaching a steady state production cell density in a period of about 1 day to about 10 days.

16. The method of claim 9, wherein the step of harvesting in (g) consists of removing culture medium and recombinant protein of (f) from the production bioreactor.

17. A method of producing a recombinant protein, wherein the method consists of:
(a) disposing a plurality of recombinant mammalian cells into a fourth culture medium within a vessel to provide a third cell culture;
(b) batch culturing the third cell culture in (a) to a cell density range of about $1.0 \times 10^6$ cells/mL to about $5.0 \times 10^6$ cells/mL,
(c) disposing a volume of the third cell culture into a first culture medium within a vessel to provide a first cell culture;
(d) batch culturing the first cell culture to a cell density range of about $1.0 \times 10^6$ cells/mL to about $5.0 \times 10^6$ cells/mL;
(e) disposing a volume of the first cell culture medium of (b) (d) into a second culture medium within a perfusion bioreactor to provide a second cell culture with an initial cell density in a range of about $0.25 \times 10^6$ cells/mL to about $0.5 \times 10^6$ cells/mL;
(f) perfusion culturing the second cell culture to a cell density range of about $5 \times 10^6$ cells/mL to about $60 \times 10^6$ cells/mL;
(g) disposing a volume of the second cell culture of (f) into a third culture medium within a production bioreactor to provide a production cell culture with an initial cell density in a range of about $0.5 \times 10^6$ cells/mL to about $10 \times 10^6$ cells/mL;
(h) perfusion culturing the production cell culture under conditions that allow the recombinant mammalian cells to secrete a recombinant protein; and (i) harvesting the recombinant protein from the production cell culture.

18. The method of claim 17, wherein the step of disposing the plurality of the recombinant mammalian cells in (a) to provide the third cell culture consists of:
   thawing a frozen cell bank; and
   disposing a volume of the thawed cell bank into the fourth culture medium.

* * * * *